(12) United States Patent
Bava et al.

(10) Patent No.: US 12,209,273 B2
(45) Date of Patent: Jan. 28, 2025

(54) NUCLEIC ACID ASSAYS USING CLICK CHEMISTRY BIOCONJUGATION

(71) Applicant: 10x Genomics, Inc., Pleasanton, CA (US)

(72) Inventors: Felice Alessio Bava, Pleasanton, CA (US); David M. Patterson, Oakland, CA (US); Meiliana Tjandra, Dublin, CA (US); Yi Luo, Pleasanton, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 867 days.

(21) Appl. No.: 17/346,077

(22) Filed: Jun. 11, 2021

(65) Prior Publication Data

US 2021/0388423 A1    Dec. 16, 2021

Related U.S. Application Data

(60) Provisional application No. 63/038,616, filed on Jun. 12, 2020.

(51) Int. Cl.
    *C12Q 1/6816*    (2018.01)
(52) U.S. Cl.
    CPC .................. *C12Q 1/6816* (2013.01)
(58) Field of Classification Search
    None
    See application file for complete search history.

(56) References Cited

U.S. PATENT DOCUMENTS

| 4,318,846 A | 3/1982 | Khanna et al. |
| 4,757,141 A | 7/1988 | Fung et al. |
| 5,066,580 A | 11/1991 | Lee |

(Continued)

FOREIGN PATENT DOCUMENTS

| WO | 2017143155 A2 | 8/2017 |
| WO | 2019199579 A1 | 10/2019 |

(Continued)

OTHER PUBLICATIONS

Bibikova et al., "Quantitative gene expression profiling in formalin-fixed, paraffin-embedded tissues using universal bead arrays," Am J Pathol. Nov. 2004;165(5):1799-807.

(Continued)

*Primary Examiner* — Samuel C Woolwine
(74) *Attorney, Agent, or Firm* — MORRISON & FOERSTER LLP

(57) ABSTRACT

Provided herein are methods of sequencing comprising click chemistry bioconjugation. In some embodiments, target polynucleotide sequences on the same or different molecules are contacted with and hybridize to probes comprising click functional groups. Probes (e.g., reading probes) hybridizing to adaptor sequences adjacent to different sequences of interest (e.g., barcodes to be sequenced) can be hybridized simultaneously in large pools. In some embodiments, the provided methods achieve multiplexing without requiring separate hybridization of probes (e.g., reading probes) for each sequencing-by-ligation cycle, thereby reducing total hybridization time which is typically a most time-consuming step in in situ technologies. In some aspects, the hybridized probes (e.g., reading probes) are clicked onto detectable probes to analyze a sequence of a target polynucleotide in a sequencing-by-ligation fashion.

22 Claims, 13 Drawing Sheets

(56) References Cited

U.S. PATENT DOCUMENTS

| | | |
|---|---|---|
| 5,091,519 A | 2/1992 | Cruickshank |
| 5,151,507 A | 9/1992 | Hobbs, Jr. et al. |
| 5,188,934 A | 2/1993 | Menchen et al. |
| 5,366,860 A | 11/1994 | Bergot et al. |
| 5,599,675 A | 2/1997 | Brenner et al. |
| 5,635,352 A | 6/1997 | Urdea et al. |
| 5,688,648 A | 11/1997 | Mathies et al. |
| 5,695,940 A | 12/1997 | Drmanac et al. |
| 5,750,341 A | 5/1998 | Macevicz |
| 5,800,996 A | 9/1998 | Lee et al. |
| 5,847,162 A | 12/1998 | Lee et al. |
| 5,990,479 A | 11/1999 | Weiss et al. |
| 6,054,274 A | 4/2000 | Sampson et al. |
| 6,172,218 B1 | 1/2001 | Brenner |
| 6,207,392 B1 | 3/2001 | Weiss et al. |
| 6,251,303 B1 | 6/2001 | Bawendi et al. |
| 6,265,552 B1 | 7/2001 | Schatz |
| 6,291,187 B1 | 9/2001 | Kingsmore et al. |
| 6,306,597 B1 | 10/2001 | Macevicz |
| 6,319,426 B1 | 11/2001 | Bawendi et al. |
| 6,322,901 B1 | 11/2001 | Bawendi et al. |
| 6,323,009 B1 | 11/2001 | Lasken et al. |
| 6,344,329 B1 | 2/2002 | Lizardi |
| 6,368,801 B1 | 4/2002 | Faruqi |
| 6,391,937 B1 | 5/2002 | Beuhler et al. |
| 6,423,551 B1 | 7/2002 | Weiss et al. |
| 6,426,513 B1 | 7/2002 | Bawendi et al. |
| 6,444,143 B2 | 9/2002 | Bawendi et al. |
| 6,534,266 B1 | 3/2003 | Singer |
| 6,576,291 B2 | 6/2003 | Bawendi et al. |
| 6,969,488 B2 | 11/2005 | Bridgham et al. |
| 7,255,994 B2 | 8/2007 | Lao |
| 7,345,159 B2 | 3/2008 | Ju et al. |
| 7,473,767 B2 | 1/2009 | Dimitrov |
| 7,534,991 B2 | 5/2009 | Miller et al. |
| 7,544,794 B1 | 6/2009 | Benner |
| 7,555,155 B2 | 6/2009 | Levenson et al. |
| 7,566,537 B2 | 7/2009 | Balasubramanian et al. |
| 7,655,898 B2 | 2/2010 | Miller |
| 7,893,227 B2 | 2/2011 | Wu et al. |
| 7,906,285 B2 | 3/2011 | Drmanac |
| 7,910,304 B2 | 3/2011 | Drmanac |
| 7,941,279 B2 | 5/2011 | Hwang et al. |
| 7,989,166 B2 | 8/2011 | Koch et al. |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,330,087 B2 | 12/2012 | Domenicali |
| 8,415,102 B2 | 4/2013 | Geiss et al. |
| 8,431,691 B2 | 4/2013 | Mckernan et al. |
| 8,460,865 B2 | 6/2013 | Chee et al. |
| 8,462,981 B2 | 6/2013 | Determan et al. |
| 8,481,258 B2 | 7/2013 | Church et al. |
| 8,519,115 B2 | 8/2013 | Webster et al. |
| 8,551,710 B2 | 10/2013 | Bernitz et al. |
| 8,632,975 B2 | 1/2014 | Vander Horn et al. |
| 8,658,361 B2 | 2/2014 | Wu et al. |
| 8,771,950 B2 | 7/2014 | Church et al. |
| 8,986,926 B2 | 3/2015 | Ferree et al. |
| 9,201,063 B2 | 12/2015 | Sood et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,404,155 B2 | 8/2016 | Bortner |
| 9,512,422 B2 | 12/2016 | Barnard et al. |
| 9,541,504 B2 | 1/2017 | Hoyt |
| 9,551,032 B2 | 1/2017 | Landegren et al. |
| 9,624,538 B2 | 4/2017 | Church et al. |
| 9,650,406 B2 | 5/2017 | Zhou et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,889,422 B2 | 2/2018 | Smith et al. |
| 9,909,167 B2 | 3/2018 | Samusik et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,138,509 B2 | 11/2018 | Church et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,550,429 B2 | 2/2020 | Harada et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,174,281 B1 | 11/2021 | Graham et al. |
| 11,287,422 B2 | 3/2022 | Previte et al. |
| 11,434,525 B2 | 9/2022 | Glezer |
| 11,459,603 B2 | 10/2022 | Tyagi et al. |
| 11,499,185 B2 | 11/2022 | Vijayan et al. |
| 11,643,679 B2 | 5/2023 | Glezer et al. |
| 11,999,999 B2 | 6/2024 | Ju et al. |
| 2002/0045045 A1 | 4/2002 | Adams et al. |
| 2003/0013091 A1 | 1/2003 | Dimitrov |
| 2003/0017264 A1 | 1/2003 | Treadway et al. |
| 2007/0166708 A1 | 7/2007 | Dimitrov et al. |
| 2010/0015607 A1 | 1/2010 | Geiss et al. |
| 2010/0047924 A1 | 2/2010 | Webster et al. |
| 2010/0055733 A1 | 3/2010 | Lutolf et al. |
| 2010/0112710 A1 | 5/2010 | Geiss et al. |
| 2010/0261026 A1 | 10/2010 | Ferree et al. |
| 2010/0262374 A1 | 10/2010 | Hwang et al. |
| 2011/0223585 A1 | 9/2011 | Gullberg et al. |
| 2013/0288249 A1 | 10/2013 | Gullbert |
| 2013/0323729 A1 | 12/2013 | Landegren et al. |
| 2014/0371088 A1 | 12/2014 | Webster |
| 2016/0024555 A1 | 1/2016 | Church et al. |
| 2016/0108458 A1 | 4/2016 | Frei et al. |
| 2016/0305856 A1 | 10/2016 | Boyden et al. |
| 2016/0376642 A1 | 12/2016 | Landegren et al. |
| 2017/0009278 A1 | 1/2017 | Söderberg et al. |
| 2017/0029872 A1 | 2/2017 | Bhattacharyya et al. |
| 2017/0081489 A1 | 3/2017 | Rodriques et al. |
| 2017/0101672 A1 | 4/2017 | Luo et al. |
| 2017/0220733 A1 | 8/2017 | Zhuang et al. |
| 2017/0253918 A1 | 9/2017 | Kohman |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0320226 A1 | 11/2018 | Church et al. |
| 2019/0017106 A1 | 1/2019 | Frisen et al. |
| 2019/0032121 A1 | 1/2019 | Daugharthy et al. |

(56) References Cited

U.S. PATENT DOCUMENTS

| | | |
|---|---|---|
| 2019/0032128 A1 | 1/2019 | Chen et al. |
| 2019/0055594 A1 | 2/2019 | Samusik et al. |
| 2019/0112599 A1 | 4/2019 | Church et al. |
| 2019/0119735 A1 | 4/2019 | Deisseroth et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0177800 A1 | 6/2019 | Boutet et al. |
| 2019/0194709 A1 | 6/2019 | Church et al. |
| 2019/0218608 A1 | 7/2019 | Daugharthy et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0339203 A1 | 11/2019 | Miller et al. |
| 2019/0367969 A1 | 12/2019 | Belhocine et al. |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |
| 2020/0239946 A1 | 7/2020 | Dewal |
| 2020/0332368 A1 | 10/2020 | Ferree et al. |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-Darling et al. |
| 2021/0017587 A1 | 1/2021 | Cai et al. |
| 2021/0115504 A1 | 4/2021 | Cai et al. |
| 2021/0238662 A1 | 8/2021 | Bava |
| 2021/0238674 A1 | 8/2021 | Bava |
| 2021/0254140 A1 | 8/2021 | Stahl et al. |
| 2021/0262018 A1 | 8/2021 | Bava et al. |
| 2021/0277460 A1 | 9/2021 | Bava |
| 2021/0340621 A1 | 11/2021 | Daugharthy et al. |
| 2021/0388423 A1 | 12/2021 | Bava et al. |
| 2021/0388424 A1 | 12/2021 | Bava |
| 2022/0049302 A1 | 2/2022 | Daugharthy et al. |
| 2022/0049303 A1 | 2/2022 | Busby et al. |
| 2022/0083832 A1 | 3/2022 | Shah |
| 2022/0084628 A1 | 3/2022 | Shah |
| 2022/0084629 A1 | 3/2022 | Shah |
| 2022/0136049 A1 | 5/2022 | Bava et al. |
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |
| 2022/0235403 A1 | 7/2022 | Costa |
| 2022/0282306 A1 | 9/2022 | Bava et al. |
| 2022/0282316 A1 | 9/2022 | Bava et al. |
| 2022/0282319 A1 | 9/2022 | Verheyen et al. |
| 2022/0372570 A1 | 11/2022 | Costa |
| 2022/0380838 A1 | 12/2022 | Kuhnemund et al. |
| 2022/0403458 A1 | 12/2022 | Bava et al. |
| 2023/0012607 A1 | 1/2023 | Kuhnemund et al. |
| 2023/0013775 A1 | 1/2023 | Chen |
| 2023/0015226 A1 | 1/2023 | Chen |
| 2023/0026886 A1 | 1/2023 | Chen |
| 2023/0031305 A1 | 2/2023 | Hernandez Neuta et al. |
| 2023/0031996 A1 | 2/2023 | Hernandez Neuta et al. |
| 2023/0035685 A1 | 2/2023 | Hernandez Neuta et al. |
| 2023/0037182 A1 | 2/2023 | Bava et al. |
| 2023/0039148 A1 | 2/2023 | Verheyen et al. |
| 2023/0041485 A1 | 2/2023 | Hernandez Neuta et al. |
| 2023/0044650 A1 | 2/2023 | Dockter |
| 2023/0057571 A1 | 2/2023 | Costa et al. |
| 2023/0061438 A1 | 3/2023 | Astier et al. |
| 2023/0061542 A1 | 3/2023 | Kuhnemund et al. |
| 2023/0084407 A1 | 3/2023 | Neuta et al. |
| 2023/0159997 A1 | 5/2023 | Belhocine et al. |
| 2023/0160794 A1 | 5/2023 | Dockter et al. |
| 2023/0183787 A1 | 6/2023 | Bava et al. |
| 2023/0242974 A1 | 8/2023 | Costa et al. |
| 2023/0279465 A1 | 9/2023 | He et al. |
| 2023/0279475 A1 | 9/2023 | Kuhnemund et al. |
| 2023/0279480 A1 | 9/2023 | Kuhnemund et al. |
| 2023/0287478 A1 | 9/2023 | Bava |
| 2023/0314327 A1 | 10/2023 | Hoffman |
| 2023/0314328 A1 | 10/2023 | Costa |
| 2023/0323427 A1 | 10/2023 | Levin |
| 2023/0323430 A1 | 10/2023 | Shastry |
| 2023/0323437 A1 | 10/2023 | Chen |
| 2023/0374573 A1 | 11/2023 | Qian et al. |
| 2023/0374580 A1 | 11/2023 | Costa |
| 2023/0416821 A1 | 12/2023 | Bava et al. |
| 2024/0002902 A1 | 1/2024 | Jakobsen et al. |
| 2024/0026426 A1 | 1/2024 | Costa |
| 2024/0026427 A1 | 1/2024 | Kuhnemund et al. |
| 2024/0026439 A1 | 1/2024 | Sasaki et al. |
| 2024/0026448 A1 | 1/2024 | Costa |
| 2024/0035070 A1 | 2/2024 | Christopherson |
| 2024/0035071 A1 | 2/2024 | Delaney et al. |
| 2024/0035072 A1 | 2/2024 | Christopherson |
| 2024/0043910 A1 | 2/2024 | Shastry |
| 2024/0043914 A1 | 2/2024 | Chen |
| 2024/0060119 A1 | 2/2024 | Bava et al. |
| 2024/0084373 A1 | 3/2024 | Shastry |
| 2024/0084378 A1 | 3/2024 | Marks et al. |
| 2024/0101978 A1 | 3/2024 | Boghospor |
| 2024/0132938 A1 | 4/2024 | Kuhnemund et al. |
| 2024/0141418 A1 | 5/2024 | Mielinis |
| 2024/0150816 A1 | 5/2024 | Feng et al. |
| 2024/0158852 A1 | 5/2024 | Belhocine et al. |
| 2024/0167081 A1 | 5/2024 | Bava et al. |
| 2024/0175082 A1 | 5/2024 | Costa |
| 2024/0175083 A1 | 5/2024 | Bava et al. |
| 2024/0191297 A1 | 6/2024 | Christopherson et al. |
| 2024/0209330 A1 | 6/2024 | Shastry et al. |
| 2024/0218424 A1 | 7/2024 | Costa et al. |
| 2024/0218437 A1 | 7/2024 | Belhocine et al. |

FOREIGN PATENT DOCUMENTS

| | | |
|---|---|---|
| WO | 2020056381 A1 | 3/2020 |
| WO | 2020076976 A1 | 4/2020 |
| WO | 2020076979 A1 | 4/2020 |
| WO | 2020096687 A1 | 5/2020 |
| WO | 2020099640 A1 | 5/2020 |
| WO | 2020117914 A1 | 6/2020 |
| WO | 2020123742 A1 | 6/2020 |
| WO | WO 2020/123316 | 6/2020 |
| WO | 2020142490 A1 | 7/2020 |
| WO | 2020240025 A1 | 12/2020 |
| WO | 2020254519 A1 | 12/2020 |
| WO | WO 2021/123282 | 6/2021 |
| WO | WO 2021/123286 | 6/2021 |
| WO | WO 2021/138676 | 7/2021 |
| WO | WO 2021/155063 | 8/2021 |
| WO | WO 2021/168326 | 8/2021 |
| WO | WO 2023/108139 | 6/2023 |
| WO | WO 2023/141476 | 7/2023 |
| WO | WO 2023/172915 | 9/2023 |
| WO | WO 2023/192302 | 10/2023 |
| WO | WO 2024/148300 | 7/2024 |

OTHER PUBLICATIONS

Capodieci et al., "Gene expression profiling in single cells within tissue," Nat Methods. (2005) 2(9): 663-5.

Conze et al., "Single molecule analysis of combinatorial splicing," Nucleic Acids Res. (2010) 38(16): e163.

Femino et al., "Visualization of single RNA transcripts in situ," Science. (1998) 280(5363): 585-90.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Gunderson et al. "Decoding randomly ordered DNA arrays." Genome research 14.5 (2004): 870-877.

(56) References Cited

OTHER PUBLICATIONS

Han et al., "Quantum-dot-tagged microbeads for multiplexed optical coding of biomolecules," Nat Biotechnol. (2001) 19(7): 631-5.
Itzkovitz et al., "Single-molecule transcript counting of stem-cell markers in the mouse intestine," Nat Cell Biol. (2011) 14(1): 106-14.
Itzkovitz et al., "Validating Transcripts with Probes and Imaging Technology," Nat Methods. (2011) 8(4 Suppl): S12-S19.
Lagunavicius et al., "Novel application of Phi29 DNA polymerase: RNA detection and analysis in vitro and in situ by target RNA-primed RCA," RNA. (2009) 15(5):765-71.
Larsson et al. "In situ detection and genotyping of individual mRNA molecules," Nat Methods. (2010) 7(5):395-397.
Levsky et al., "Fluorescence in situ hybridization: past, present and future," J Cell Sci. (2003) 116(Pt 14): 2833-8.
Levsky et al., "Single-cell gene expression profiling," Science. (2002) 297(5582): 836-40.
Maierhorfer et al., "Multicolor deconvolution microscopy of thick biological specimens," Am J Pathol. (2003) 162(2): 373-9.
Meade et al. "Multiplexed DNA detection using spectrally encoded porous SiO2 photonic crystal particles," Anal Chem. (2009) 81(7): 2618-25.
Raj et al., "Imaging individual mRNA molecules using multiple singly labeled probes," Nat Methods. (2008) 5(10): 877-879.
Sun et al., "Composite organic-inorganic nanoparticles as Raman labels for tissue analysis," Nano Lett. (2007) 7(2): 351-6.
Wählby et al., "Sequential immunofluorescence staining and image analysis for detection of large numbers of antigens in individual cell nuclei," Cytometry. (2002) 47(1): 32-41.
Weibrecht et al., "Simultaneous visualization of both signaling cascade activity and end-point gene expression in single cells," PLoS One. (2011) 6(5): e20148.
Wilson et al., "Encoded microcarriers for high-throughput multiplexed detection," Angew Chem Int Ed Engl. (2006) 18;45(37): 6104-17.
Zhao et al., "Advances of multiplex and high throughput biomolecular detection technologies based on encoding microparticles," Sci China Chem. (2011) 54(8):1185.
Allawi et al., "Thermodynamics and NMR of internal G.T mismatches in DNA," Biochemistry, (1997) 36:10581-94.
Archer et al., "Selective and flexible depletion of problematic sequences from RNA-seq libraries at the cDNA stage," BMC Genomics. (2014) 15(1):401.
Baner et al., "Signal amplification of padlock probes by rolling circle replication," Nucleic Acids Res. (1998) 26 (22):5073-5078.
Berger et al., "Universal bases for hybridization, replication and chain termination," Nucleic Acid Res. (2000) 28(15): 2911-2914.
Bio et al., "Click and photo-unclick chemistry of aminoacrylate for visible light-triggered drug release," Chem. Commun. (2012) 48(52); 6517-6519.
Bolognesi et al., "Multiplex Staining by Sequential Immunostaining and Antibody Removal on Routine Tissue Sections," J. Histochem. Cytochem. (2017); 65(8): 431-444.
Chen et al., "Nanoscale imaging of RNA with expansion microscopy," Nat Methods. (2016) 13:679-684.
Chen, F. et al. "Expansion Microscopy," Science (2015) 347(6221):543-548.
Dean et al., "Rapid Amplification Of Plasmid And Phage DNA Using Phi29 DNA Polymerase And Multiply-Primed Rolling Circle Amplification," Genome Research (2001) 11:1095-1099.
Fang et al., "Fluoride-Cleavable Biotinylation Phosphoramidite for 5'-end-Labelling and Affinity Purification of Synthetic Oligonucleotides," Nucleic Acids Res. (2003) 31(2): 708-715.
Faruqi et al., "High-throughput genotyping of single nucleotide polymorphisms with rolling circle amplification," BMC Genomics. (2001) 2:4.
Gartner et al., "The Generality of DNA-Templated Synthesis as a Basis for Evolving Non-Natural Small Molecules," J. Am. Chem. Soc. (2001), 123(28); 6961-6963.

Glass et al., "SIMPLE: a sequential immunoperoxidase labeling and erasing method," J Histochem Cytochem. (2009) 57(10); 899-905.
Goh, J.J.L. et al. (Jul. 2020, e-pub. Jun. 15, 2020). "Highly Specific Multiplexed RNA Imaging In Tissues With Split-FISH," Nat Methods 17(7):689-693.
Goransson, J. et al. (Jan. 2009, e-pub. Nov. 25, 2008). "A Single Molecule Array For Digital Targeted Molecular Analyses," Nucleic Acids Res 37(1):e7, 9 pages.
Guo et al., "Four-color DNA sequencing with 3'-O-modified nucleotide reversible terminators and chemically cleavable fluorescent dideoxynucleotides," Proc Natl Acad Sci U S A. (2008) 105(27): 9145-50.
Gyllborg et al., "Hybridization-based in situ sequencing (HybISS) for spatially resolved transcriptomics in human and mouse brain tissue," Nucleic Acids Res. (2020) 48(19): e112.
Henegariu et al., "Custom fluorescent-nucleotide synthesis as an alternative method for nucleic acid labeling," Nature Biotechnol. (2000) 18:345.
Jamur et al., "Permeabilization of cell membranes," Method Mol. Biol. (2010) 588: 63-66 (abstract only).
Ju et al., "Four-color DNA sequencing by synthesis using cleavable fluorescent nucleotide reversible terminators," Proc Natl Acad Sci U S A. (2006) 103(52): 19635-40.
Kanehisa, "Use of statistical criteria for screening potential homologies in nucleic acid sequences," Nucleic Acids Res. (1984) 12:203-213.
Lakowicz et al., "Silver particles enhance emission of fluorescent DNA oligomers," Bio Techniques (2003) 34(1); 62-66.
Lee, J.H. et al. (Mar. 21, 2014, e-pub. Sep. 21, 2014). "Highly Multiplexed Subcellular RNA Sequencing In Situ", Science 343(6177):1360-1363.
Lin et al., "Highly multiplexed imaging of single cells using a high-throughput cyclic immunofluorescence method," Nat Commun. (2015) 6:8390.
Liu, S. et al. (2021, e-pub. Mar. 8, 2021). "Barcoded Oligonucleotides Ligated On RNA Amplified For Multiplexed And Parallel In Situ Analyses," Nucleic Acids Res. 49(10):e58, 15 pages.
Lizardi et al., "Mutation detection and single-molecule counting using isothermal rolling-circle amplification," Nat Genet. (1998) 19(3): 225-232.
McGinn et al., "New technologies for DNA analysis—a review of the READNA Project," N Biotechnol. (2016) 33(3): 311-30. doi: 10.1016/j.nbt.2015.10.003.
Mitra et al., "Fluorescent in situ sequencing on polymerase colonies," Anal. Biochem. (2003) 320; 55-65.
Moffitt et al., "RNA Imaging with Multiplexed Error-Robust Fluorescence In Situ Hybridization (MERFISH)," Methods in Enzymology, (2016) 572; 1-49.
Nallur et al., "Signal amplification by rolling circle amplification on DNA microarrays," Nucleic Acids Res. (2001) 29 (23): e118.
Patterson et al., "Finding the right (bioorthogonal) chemistry," ACS Chem. Biol. (2014) 9(3): 592-605.
Payne, A.C. et al. (Feb. 26, 2021, e-pub Dec. 31, 2020). "In Situ Genome Sequencing Resolves DNA Sequence And Structure In Intact Biological Samples," Science 371(6532):1-19, 20 pages.
Pirici et al., "Antibody elution method for multiple immunohistochemistry on primary antibodies raised in the same species and of the same subtype," J Histochem Cytochem. (2009) 57(6); 567-75.
Rouhanifard, S.H. et al. (Nov. 12, 2018, e-pub. May 13, 2019). "Clampfish Detects Individual Nucleic Acid Molecules Using Click Chemistry-Based Amplification," Nat Biotechnol, 17 pages.
Schweitzer et al. "Immunoassays with rolling circle DNA amplification: A versatile platform for ultrasensitive antigen detection," Proc. Natl Acad. Sci. USA (2000) 97:10113-119.
Schweitzer et al., "Multiplexed protein profiling on microarrays by rolling-circle amplification," Nature Biotech, (2002) 20:359-365.
Seckute et al., "Rapid oligonucleotide-templated fluorogenic tetrazine ligations," Nucleic Acids Res. (2013) 41(15); e148.
Seo et al., "Four-color DNA sequencing by synthesis on a chip using photocleavable fluorescent nucleotides," PNAS (2005) 102(17); 5926-5931.

(56) References Cited

OTHER PUBLICATIONS

Shendure et al., "Accurate multiplex polony sequencing of an evolved bacterial genome," Science (2005) 309 (5741); 1728-1732.
Takei, Y. et al. (Feb. 2021, e-pub Jan. 27, 2021). "Integrated Spatial Genomics Reveals Global Architecture Of Single Nuclei," Nature 590(7845):344-350, 53 pages.
Vandernoot et al., "cDNA normalization by hydroxyapatite chromatography to enrich transcriptome diversity in RNA-seq applications," Biotechniques, (2012) 53(6) 373-80.
Wang et al., "Three-dimensional intact-tissue sequencing of single-cell transcriptional states," Science. (2018) 361 (6400): eaat5691.
Wetmur, "DNA Probes: Applications of the Principles of Nucleic Acid Hybridization," Critical Reviews in Biochemistry and Molecular Biology, (1991) 26(91); 227-259.
Wu, C. et al. (Nov. 28, 2018). "RollFISh Achieves Robust Quantification Of Single-Molecule RNA Biomarkers In Paraffin-Embedded Tumor Tissue Samples," Commun Biol. 1:(209):1-8.
Xiong et al., "Stepwise "Click" Chemistry for the Template Independent Construction of a Broad Variety of Cross-Linked Oligonucleotides: Influence of Linker Length, Position, and Linking Number on DNA Duplex Stability," J. Org. Chem. (2011) 76(14): 5584-5597.

FIG. 7

Readout chemistry: *in situ* sequencing - click chemistry
Scalability and acquisition-time Example: Click. 1,000 genes

| Step | Chemistry | Time (minutes) |
|---|---|---|
| 1 | Hybridization Reading probes | 20 |
| 2 | Click-chem 1 Fluo-oligo | 5 |
| 3 | Wash excess | 1 |
| 4 | IMAGE | 5 |
| 5 | Wash/un-click/Fluorophore release | 5 |
| 6 | Go back to Step 2 (until Click "n") | |
| TOTAL TIME | | 20+ (16 x 6)= 116 |

For 1000 genes = 2 hours of acquisition

NUCLEIC ACID ASSAYS USING CLICK CHEMISTRY BIOCONJUGATION

CROSS-REFERENCE TO RELATED APPLICATION

This application claims priority to U.S. Provisional Application No. 63/038,616, filed Jun. 12, 2020, entitled "NUCLEIC ACID ASSAYS USING CLICK CHEMISTRY BIOCONJUGATION," which is incorporated by reference in its entirety for all purposes.

FIELD

The present disclosure in some aspects provides devices, methods, and systems for sequence analysis of a target nucleic acid molecule, such as in in situ gene analysis of a target nucleic acid in a tissue.

BACKGROUND

Transcription profiling of cells are essential for many purposes. Microscopy imaging which can resolve multiple mRNAs in single cells can provide valuable information regarding transcript abundance and localization in situ, which are important for understanding the molecular basis of cell identify and developing treatment for diseases.

The bottle neck of in situ technologies with microscopy readout is imaging time. Sequencing approaches rely on enzymatic activities (often that of ligases) that require long incubation times (for example, four hours) to complete each readout cycle. To render 1,000 genes by in situ sequencing approaches, acquisition times of 24 hours may be required. When gene throughput increases to 10,000, sequential hybridization-based approaches require imaging times in the scale of days. Therefore, there is a need for new and improved methods for profiling transcripts in situ.

BRIEF SUMMARY

The present disclosure in some aspects provides devices, methods, and systems for sequence analysis of a target nucleic acid molecule, such as in in situ gene analysis of a target nucleic acid in a tissue, including in situ sequencing or in situ hybridization based assays. In some aspects, the present disclosure addresses limitations of existing sequence analysis techniques due to the low efficiency of enzymatic ligation, e.g., leading to increased sequencing output and/or accuracy. The present disclosure may be applied in any sequence analysis that currently uses enzymatic ligation and may be combined with enzymatic ligation.

In some aspects, provided herein are methods of nucleic acid sequencing using click chemistry bioconjugation. In some embodiments, templates comprising target polynucleotide sequences on the same or different molecules are contacted with and hybridize to probes comprising click functional groups. Probes for analyzing different sequences of interest can be hybridized simultaneously in large pools. In this manner, the provided methods achieve multiplexing without increasing hybridization time, typically one of the longest step in in situ technologies.

Provided herein are methods comprising (a) contacting a first nucleic acid sequence, a second nucleic acid sequence, a first probe (e.g., first reading probe) comprising click functional group C1, and a second probe (e.g., second reading probe) comprising click functional group C2, to form a hybridization mix, wherein the first nucleic acid sequence comprises a first adaptor and a first target polynucleotide sequence adjacent to the first adaptor, the second nucleic acid sequence comprises a second adaptor and a second target polynucleotide sequence adjacent to the second adaptor, and wherein the first probe (e.g., first reading probe) hybridizes to the first adaptor, and the second probe (e.g., second reading probe) hybridizes to the second adaptor; (b) contacting the hybridization mix with a first detectable probe comprising click functional group C1' and a first detectable label, wherein the first probe hybridizes to the first target polynucleotide adjacent to the first adaptor, thereby juxtaposing click functional groups C1 and C1'; (c) reacting click functional group C1 with click functional group C1', thereby ligating the first probe (e.g., first reading probe) to the first detectable probe to form a first ligated product hybridized on the first nucleic acid sequence, wherein the first ligated product comprises the first detectable label; and (d) detecting a first signal from the first detectable label, wherein the first signal is indicative of a sequence of the first target polynucleotide.

Also provided herein are methods comprising contacting a first nucleic acid sequence, a second nucleic acid sequence, a first probe (e.g., first reading probe) comprising click functional group C1, and a second probe (e.g., second reading probe) comprising click functional group C2, to form a hybridization mix, wherein the first nucleic acid sequence comprises a first adaptor and a first target polynucleotide adjacent to the first adaptor, the second nucleic acid sequence comprises a second adaptor and a second target polynucleotide sequence adjacent to the second adaptor, and wherein the first probe (e.g., first reading probe) hybridizes to the first adaptor, and the second probe (e.g., second reading probe) hybridizes to the second adaptor; the hybridization mix is contacted with a first detectable probe comprising click functional group C1' and a first detectable label, wherein the first probe hybridizes to the first target polynucleotide sequence adjacent to the first adaptor, thereby juxtaposing click functional groups C1 and C1'; click functional group C1 reacts with click functional group C1', thereby ligating the first probe (e.g., first reading probe) to the first detectable probe to form a first ligated product hybridized on the first nucleic acid sequence, wherein the first ligated product comprises the first detectable label; and a first signal from the first detectable label is detected, wherein the first signal is indicative of a sequence of the first target polynucleotide.

Also provided herein are methods comprising contacting a hybridization mix with a first detectable probe, wherein the hybridization mix comprises a first nucleic acid sequence, a second nucleic acid sequence, a first probe (e.g., first reading probe) comprising click functional group C1, and a second probe (e.g., second reading probe) comprising click functional group C2, wherein the first nucleic acid sequence comprises a first adaptor and a first target polynucleotide adjacent to the first adaptor, the second nucleic acid sequence comprises a second adaptor and a second target polynucleotide adjacent to the second adaptor, the first probe (e.g., first reading probe) hybridizes to the first adaptor, and the second probe (e.g., second reading probe) hybridizes to the second adaptor; the first detectable probe comprises click functional group C1' and a first detectable label, wherein the first probe hybridizes to the first target polynucleotide adjacent to the first adaptor, thereby juxtaposing click functional groups C1 and C1'; click functional group C1 reacts with click functional group C1', thereby ligating the first probe (e.g., first reading probe) to the first detectable probe to form a first ligated product hybridized on the first nucleic acid sequence, wherein the first ligated product comprises the first detectable label; and a first signal from the first detectable label is detected, wherein the first signal is indicative of a sequence of the first target polynucleotide.

Also provided herein are methods wherein a hybridization mix is contacted with a first detectable probe, the hybridization mix comprising a first nucleic acid sequence, a second nucleic acid sequence, a first probe (e.g., first reading probe) comprising click functional group C1, and a second probe (e.g., second reading probe) comprising click functional group C2, wherein the first nucleic acid sequence comprises a first adaptor and a first target polynucleotide adjacent to the first adaptor, the second nucleic acid sequence comprises a second adaptor and a second target polynucleotide adjacent to the second adaptor, the first probe (e.g., first reading probe) hybridizes to the first adaptor, and the second probe (e.g., second reading probe) hybridizes to the second adaptor, wherein the first detectable probe comprises click functional group C1' and a first detectable label, wherein the first probe hybridizes to the first target polynucleotide adjacent to the first adaptor, thereby juxtaposing click functional groups C1 and C1', the method comprising reacting click functional group C1 with click functional group C1', thereby ligating the first probe (e.g., first reading probe) to the first detectable probe to form a first ligated product hybridized on the first nucleic acid sequence, wherein the first ligated product comprises the first detectable label, wherein a first signal from the first detectable label is detected, wherein the first signal is indicative of a sequence of the first target polynucleotide.

Also provided herein are methods wherein a hybridization mix is contacted with a first detectable probe, the hybridization mix comprising a first nucleic acid sequence, a second nucleic acid sequence, a first probe (e.g., first reading probe) comprising click functional group C1, and a second probe (e.g., second reading probe) comprising click functional group C2, wherein the first nucleic acid sequence comprises a first adaptor and a first target polynucleotide adjacent to the first adaptor, the second nucleic acid sequence comprises a second adaptor and a second target polynucleotide adjacent to the second adaptor, the first probe (e.g., first reading probe) hybridizes to the first adaptor, and the second probe (e.g., second reading probe) hybridizes to the second adaptor, wherein the first detectable probe comprises click functional group C1' and a first detectable label, wherein the first probe hybridizes to the first target polynucleotide adjacent to the first adaptor, thereby juxtaposing click functional groups C1 and C1', wherein click functional group C1 is reacted with click functional group C1', thereby ligating the first probe (e.g., first reading probe) to the first detectable probe to form a first ligated product hybridized on the first nucleic acid sequence, wherein the first ligated product comprises the first detectable label, the method comprising detecting a first signal from the first detectable label is detected, wherein the first signal is indicative of a sequence of the first target polynucleotide.

In any of the preceding embodiments, the hybridization mix can be contacted with a second detectable probe comprising click functional group C2' and a second detectable label, wherein the second detectable probe can hybridize to the second target polynucleotide adjacent to the second adaptor, thereby juxtaposing click functional groups C2 and C2'. In some embodiments, click functional group C2 can be reacted with click functional group C2', thereby ligating the second probe (e.g., second reading probe) to the second detectable probe to form a second ligated product hybridized on the second nucleic acid sequence, wherein the second ligated product can comprise the second detectable label. In some embodiments, a second signal from the second detectable label can be detected, wherein the second signal can be indicative of a sequence of the second target polynucleotide.

In any of the preceding embodiments, the hybridization mix can further comprise a third template and a third probe comprising click functional group C3, wherein the third template can comprise a third adaptor and a third target polynucleotide adjacent to the third adaptor, and wherein the third probe can hybridize to the third adaptor. In some embodiments, the hybridization mix can be contacted with a third detectable probe comprising click functional group C3' and a third detectable label, wherein the third detectable probe can hybridize to the third target polynucleotide adjacent to the third adaptor, thereby juxtaposing click functional groups C3 and C3'. In some embodiments, click functional group C3 can be reacted with click functional group C3', thereby ligating the third probe to the third detectable probe to form a third ligated product hybridized on the third template, wherein the third ligated product can comprise the third detectable label. In some embodiments, a third signal from the third detectable label can be detected, wherein the third signal can be indicative of a sequence of the third target polynucleotide.

In any of the preceding embodiments, the hybridization mix can further comprise a fourth template and a fourth probe comprising click functional group C4, wherein the fourth template can comprise a fourth adaptor and a fourth target polynucleotide adjacent to the fourth adaptor, and wherein the fourth probe can hybridize to the fourth adaptor. In some embodiments, the hybridization mix can be contacted with a fourth detectable probe comprising click functional group C4' and a fourth detectable label, wherein the fourth detectable probe can hybridize to the fourth target polynucleotide adjacent to the fourth adaptor, thereby juxtaposing click functional groups C4 and C4'. In some embodiments, click functional group C4 can be reacted with click functional group C4', thereby ligating the fourth probe to the fourth detectable probe to form a fourth ligated product hybridized on the fourth template, wherein the fourth ligated product can comprise the fourth detectable label. In some embodiments, a fourth signal from the fourth detectable label can be detected, wherein the fourth signal can be indicative of a sequence of the fourth target polynucleotide.

In any of the preceding embodiments, the click reaction between C1/C1', the click reaction between C2/C2', the click reaction between C3/C3', and/or the click reaction between C4/C4' can be different from one another. In any of the preceding embodiments, the click reaction between C1/C1', the click reaction between C2/C2', the click reaction between C3/C3', and/or the click reaction between C4/C4' can be bioorthogonal.

In any of the preceding embodiments, the first adaptor, the second adaptor, the third adaptor, and/or the fourth adaptor can have the same nucleic acid sequence. In any of the preceding embodiments, the first probe (e.g., first reading probe), the second probe (e.g., second reading probe), the third probe, and/or the fourth probe can have the same nucleic acid sequence. In any of the preceding embodiments, the first adaptor, the second adaptor, the third adaptor, and/or the fourth adaptor can have different nucleic acid sequences. In any of the preceding embodiments, the first probe (e.g., first reading probe), the second probe (e.g., second reading probe), the third probe, and/or the fourth probe can have different nucleic acid sequences. In any of the preceding embodiments, the nucleic acid sequences of the first adaptor, the second adaptor, the third adaptor, and/or the fourth adaptor can be known, and/or wherein the nucleic acid sequences of the first probe (e.g., first reading probe), the second probe (e.g., second reading probe), the third probe, and/or the fourth probe can be known.

In any of the preceding embodiments, the click reaction between C1/C1', the click reaction between C2/C2', the click reaction between C3/C3', and/or the click reaction between C4/C4' can be the same reaction, and the first adaptor, the second adaptor, the third adaptor, and/or the fourth adaptor can have different nucleic acid sequences. In some embodiments, the click reaction between C1/C1' and the click reaction between C2/C2' can be the same reaction, and the first adaptor and the second adaptor can have different nucleic acid sequences.

In any of the preceding embodiments, the first nucleic acid sequence, the second nucleic acid sequence, the third template, and/or the fourth template can be in the same nucleic acid molecule. In any of the preceding embodiments, the first nucleic acid sequence, the second nucleic acid sequence, the third template, and/or the fourth template can be in different nucleic acid molecules. In any of the preceding embodiments, the first nucleic acid sequence, the second nucleic acid sequence, the third template, and/or the fourth template can comprise a concatemer comprising a plurality of monomeric units.

In any of the preceding embodiments, the first target polynucleotide, the second target polynucleotide, the third target polynucleotide, and/or the fourth target polynucleotide can comprise a barcode sequence that identifies a nucleic acid sequence. In some embodiments, the nucleic acid sequence can comprise a DNA or an RNA sequence of a gene. In some embodiments, the barcode sequence can uniquely identify the gene.

In any of the preceding embodiments, the first nucleic acid sequence, the second nucleic acid sequence, the third template, and/or the fourth template can be produced through rolling circle amplification (RCA) of a circular construct directly or indirectly hybridized to a target nucleic acid in a sample. In some embodiments, the RCA can comprise a linear RCA, a branched RCA, a dendritic RCA, or any combination thereof. In any of the preceding embodiments, the sample can be a non-homogenized tissue sample. In any of the preceding embodiments, the sample can be an intact tissue sample. In any of the preceding embodiments, the target nucleic acid can be in a cell in the sample. In some embodiments, the methods can further comprise permeabilizing the cell before, during, or after the contacting step. In any of the preceding embodiments, the sample can be fixed. In some embodiments, the methods can further comprise fixing the sample.

In any of the preceding embodiments, the target nucleic acid can comprise a DNA and/or an RNA. In some embodiments, the RNA can be an mRNA. In any of the preceding embodiments, the target polynucleotide in the template can be DNA and the target nucleic acid can be RNA.

In any of the preceding embodiments, the circular construct can directly hybridize to the target nucleic acid in the sample. In some embodiments, the circular construct can be formed from a probe or probe set selected from the group consisting of a padlock probe, a probe or probe set capable of RNA-templated ligation, a SNAIL (specific amplification of nucleic acids via intramolecular ligation) probe set, a probe set capable of proximity ligation, e.g., a PLAYR (proximity ligation assay for RNA) probe set, and any combination thereof. In any of the preceding embodiments, the circular construct can indirectly hybridize to the target nucleic acid in the sample. In some embodiments, the circular construct can be formed from a probe set capable of proximity ligation, e.g., a PLISH (proximity ligation in situ hybridization) probe set. In any of the preceding embodiments, the methods can further comprise forming the circular construct directly or indirectly hybridized to the target nucleic acid. In some embodiments, the forming step can comprise ligation, templated primer extension followed by ligation, providing an insert between two ends to be connected, or any combination thereof. In some embodiments, the ligation can be a DNA-templated ligation or an RNA-templated ligation. In some embodiments, the method can further comprise providing a splint as the template for the ligation.

In any of the preceding embodiments, the click reaction can be selected from the group consisting of a nucleophilic addition reaction, a cyclopropane-tetrazine reaction, a strain-promoted azide-alkyne cycloaddition (SPAAC) reaction, an alkyne hydrothiolation reaction, an alkene hydrothiolation reaction, a strain-promoted alkyne-nitrone cycloaddition (SPANC) reaction, an inverse electron-demand Diels-Alder (IED-DA) reaction, a cyanobenzothiazole condensation reaction, an aldehyde/ketone condensation reaction, and Cu(I)-catalyzed azide-alkyne cycloaddition (CuAAC) reaction. In any of the preceding embodiments, the click reaction can be a template-dependent reaction or a template-independent reaction. In some embodiments, the template-dependent reaction can be a nucleophilic addition template-dependent reaction or a cyclopropane-tetrazine template-dependent reaction. In any of the preceding embodiments, the click reaction can be biocompatible. In any of the preceding embodiments, the click functional group C1 can be on the 5' of the probe and the click functional group C1' can be on the 3' of the detectable probe. In some embodiments, the click functional group C1 and the click functional group C1' can be selected from the following pairs: (i) 3'-azido/5'-alkynyl; (ii) 3'-alkynyl/5'-azido; (iii) 3'-azido/5'-cyclooctynyl; (iv) 3'-cyclooctynyl/5'-azido; (v) 3'-tetrazine/5'-dienophile; (vi) 3'-dienophile/5'-tetrazine; (vii) 3'-thiol/5'-alkynyl; (viii) 3'-alkynyl/5'-thiol; (ix) 3'-cyano/5'-1,2-amino thiol; (x) 3'-1,2-amino thiol/5'-cyano; (xi) 3'-nitrone/5'-cyclooctynyl; or (xii) 3'-cyclooctynyl/5'-nitrone.

In any of the preceding embodiments, the first detectable probe, the second detectable probe, the third detectable probe, and/or the fourth detectable probe can be two or more nucleotides in length. In any of the preceding embodiments, the first detectable probe, the second detectable probe, the third detectable probe, and/or the fourth detectable probe can comprise a plurality of detectable probes of formula $N_xB_yN_z$, wherein N can be a degenerate base and B can be an interrogatory base, x, y, and z can be integers independent of each other, wherein x can be 0 or greater, y can be 1 or greater, and z can be 0 or greater.

In any of the preceding embodiments, the first detectable label, the second detectable label, the third detectable label, and/or the fourth detectable label can be fluorescent. In some embodiments, the first detectable label, the second detectable label, the third detectable label, and/or the fourth detectable label can be on the 5' of the first detectable probe, the second detectable probe, the third detectable probe, and/or the fourth detectable probe, respectively. In any of the preceding embodiments, the first detectable probe, the second detectable probe, the third detectable probe, and/or the fourth detectable probe comprise a plurality of detectable probes can each comprise a different fluorophore.

In any of the preceding embodiments, the first detectable label, the second detectable label, the third detectable label, and/or the fourth detectable label can be linked to the first detectable probe, the second detectable probe, the third detectable probe, and/or the fourth detectable probe, respectively, via a cleavable linker. In some embodiments, the cleavable linker can comprise a photocleavable linker, a Pd-cleavable linker, and/or a phosphine-cleavable linker. In any of the preceding embodiments, the cleavable linker can comprise a nitrobenzyl, an allyl, and/or an azide.

In any of the preceding embodiments, the first probe (e.g., first reading probe), the second probe (e.g., second reading probe), the third probe (e.g., third reading probe), and/or the fourth probe (e.g., fourth reading probe) can hybridize to the first adaptor, the second adaptor, the third adaptor, and/or the fourth adaptor, respectively, in the same contacting step; and/or the first adaptor, the second adaptor, the third adaptor, and/or the fourth adaptor can be universal adaptors or comprise one or more universal adaptor sequences. In some embodiments, the first probe (e.g., first reading probe), the second probe (e.g., second reading probe), the third probe (e.g., third reading probe), and/or the fourth probe (e.g., fourth reading probe) can remain hybridized to the first adaptor, the second adaptor, the third adaptor, and/or the fourth adaptor, respectively, during one or more cycles of the contacting with the detectable probes, click reaction, and/or signal detection. In any of the preceding embodiments, the first ligated product, the second ligated product, the third ligated product, and/or the fourth ligated product can be unhybridized from the corresponding template or cleaved after signal detection.

Also provided herein are methods for analyzing target nucleic acid sequences, comprising (i) contacting a sample with a plurality of probes, wherein the sample comprises a plurality of templates, wherein each template comprises an adaptor and a target polynucleotide adjacent to the adaptor; the plurality of probes comprise at least a first subset and a second subset, wherein each probe of the first subset comprises click functional group C1 capable of a first click reaction with click functional group C1', and each probe of the second subset comprises click functional group C2 capable of a second click reaction with click functional group C2', wherein the first and second click ligation reactions are optionally biorthogonal; and the plurality of probes hybridize to the adaptors in the templates; (ii) contacting the sample with a plurality of first detectable probes), wherein the plurality of first detectable probes are of formula $N_xB_yN_z$, wherein N is a degenerate base and B is an interrogatory base, x, y, and z are integers independent of each other, wherein x is 0 or greater, y is 1 or greater, and z is 0 or greater; each first detectable probe comprises click functional group C1' and a first fluorescent label; and the plurality of first detectable probes hybridize to the target polynucleotides adjacent to the adaptors, thereby juxtaposing click functional groups C1 and C1'; (iii) performing the first click reaction between click functional groups C1 and C1' to form first ligated complexes on the templates, wherein unligated first detectable probes are optionally removed; and (iv) detecting a first fluorescent signal indicative of a first target nucleic acid sequence from the first fluorescent labels in the first ligated complexes.

In some embodiments, the methods can further comprise (v) unclicking the first click reaction between click functional groups C1 and C1'. In any of the preceding embodiments, the methods can further comprise (vi) contacting the sample with a plurality of second detectable probes, wherein the plurality of second detectable probes are of formula $N_xB_yN_z$, wherein N is a degenerate base and B is an interrogatory base, x, y, and z are integers independent of each other, wherein x is 0 or greater, y is 1 or greater, and z is 0 or greater; each second detectable probe comprises click functional group C2' and a second fluorescent label; and the plurality of second detectable probes hybridize to the target polynucleotides adjacent to the adaptors, thereby juxtaposing click functional groups C2 and C2'; (vii) performing the second click reaction between click functional groups C2 and C2' to form second ligated complexes on the templates, wherein unligated second detectable probes are optionally removed; (viii) detecting a second fluorescent signal indicative of a second target nucleic acid sequence from the second fluorescent labels in the second ligated complexes. In some embodiments, the methods can further comprise (ix) unclicking the second click reaction between click functional groups C2 and C2'.

In any of the preceding embodiments, the plurality of probes can comprise at least a third subset, wherein each probe of the third subset can comprise click functional group C3 capable of a third click reaction with click functional group C3', and the third click reaction can be optionally bioorthogonal. In some embodiments, the methods can further comprise performing steps essentially as described in (ii)-(iv) and optionally (v) for the third click ligation reaction. In any of the preceding embodiments, the plurality of probes can comprise at least a fourth subset, wherein each probe of the fourth subset can comprise click functional group C4 capable of a third click reaction with click functional group C4', and the fourth click reaction can be optionally bioorthogonal. In some embodiments, the methods can further comprise performing steps essentially as described in (ii)-(iv) and optionally (v) for the fourth click ligation reaction.

In any of the preceding embodiments, the plurality of first detectable probes, the plurality of second detectable probes, the plurality of third detectable probes, and/or the plurality of fourth detectable probes can be two nucleotides in length. In any of the preceding embodiments, the plurality of first detectable probes, the plurality of second detectable probes, the plurality of third detectable probes, and/or the plurality of fourth detectable probes can be two or more nucleotides in length. In any of the preceding embodiments, the first fluorescent label, the second fluorescent label, the third fluorescent label, and/or the fourth fluorescent label can be the same or different. In some embodiments, the first fluorescent label, the second fluorescent label, the third fluorescent label, and the fourth fluorescent label can be different.

In any of the preceding embodiments, the target polynucleotide can comprise a sequence derived from a target nucleic acid in the sample and/or can comprise a barcode that uniquely identifies the target nucleic acid.

Also provided herein are methods for analyzing target nucleic acid sequences, comprising (i) contacting a sample with a plurality of probes, wherein the sample comprises a plurality of templates, wherein each template comprises an adaptor and a target polynucleotide adjacent to the adaptor, wherein the target polynucleotide comprises a sequence derived from a target nucleic acid in the sample and/or comprises a barcode that uniquely identifies the target nucleic acid; the plurality of probes comprise at least a first subset and a second subset, wherein each probe of the first subset comprises click functional group C1 capable of a first click reaction with click functional group C1', and each probe of the second subset comprises click functional group C2 capable of a second click reaction with click functional group C2', wherein the first and second click ligation reactions are optionally biorthogonal; and the plurality of probes hybridize to the adaptors in the templates; (ii) contacting the sample with a plurality of first detectable probes, wherein the plurality of first detectable probes are of formula $N_xB_yN_z$, wherein N is a degenerate base and B is an interrogatory base, x, y, and z are integers independent of each other, wherein x is 0 or greater, y is 1 or greater, and z is 0 or greater; the plurality of first detectable probes comprise at least a first subset and a second subset, wherein each first detectable probe of the first subset comprises click functional group C1' and fluorescent label Fr, and each first detectable probe of the second subset comprises click functional group C1' and fluorescent label Fg, wherein fluorescent labels Fr and Fg are different; and the plurality of first detectable probes hybridize to the target polynucleotides adjacent to the adaptors, thereby juxtaposing click functional groups C1 and C1'; (iii) performing the first click reaction between click functional groups C1 and C1' to form first ligated complexes on the templates, wherein unligated first detectable probes are optionally removed; (iv) detecting fluorescent signals from fluorescent labels Fr and Fg in the first ligated complexes, indicative of a first target nucleic acid sequence and a second target nucleic acid sequence, respectively.

In some embodiments, the methods can further comprise (v) unclicking the first click reaction between click functional groups C1 and C1'. In any of the preceding embodiments, the methods can further comprise (vi) contacting the sample with a plurality of second detectable probes, wherein the plurality of second detectable probes are of formula $N_xB_yN_z$, wherein N is a degenerate base and B is an interrogatory base, x, y, and z are integers independent of each other, wherein x is 0 or greater, y is 1 or greater, and z is 0 or greater; the plurality of second detectable probes comprise at least a first subset and a second subset, wherein each second detectable probe of the first subset comprises click functional group C2' and fluorescent label Fr, and each second detectable probe of the second subset comprises click functional group C2' and a fluorescent label Fg; and the plurality of second detectable probes hybridize to the target polynucleotides adjacent to the adaptors, thereby juxtaposing click functional groups C2 and C2'; (iii) performing the second click reaction between click functional groups C2 and C2' to form second ligated complexes on the templates, wherein unligated second detectable probes are optionally removed; (iv) detecting fluorescent signals from fluorescent labels Fr and Fg in the second ligated complexes, indicative of a third target nucleic acid sequence and a fourth target nucleic acid sequence, respectively. In some embodiments, the methods can further comprise (ix) unclicking the second click reaction between click functional groups C2 and C2'.

In any of the preceding embodiments, the plurality of probes can comprise at least a third subset, wherein each probe of the third subset can comprise click functional group C3 capable of a third click reaction with click functional group C3', and the third click reaction can be optionally biorthogonal. In some embodiments, the methods can further comprise performing steps essentially as described in (ii)-(iv) and optionally (v) for the third click ligation reaction. In some embodiments, the plurality of first detectable probes, the plurality of second detectable probes, and/or the plurality of third detectable probes can comprise a third subset in which each detectable probe can comprise click functional group C1', C2', or C3' and fluorescent label Fb, wherein Fr, Fg and Fb can be different.

In any of the preceding embodiments, the plurality of probes can comprise at least a fourth subset, wherein each probe of the fourth subset can comprise click functional group C4 capable of a fourth click reaction with click functional group C4', and the fourth click reaction is optionally biorthogonal. In some embodiments, the methods can further comprise performing steps essentially as described in (ii)-(iv) and optionally (v) for the fourth click ligation reaction. In some embodiments, the plurality of first detectable probes, the plurality of second detectable probes, the plurality of third detectable probes, and/or the plurality of fourth detectable probes can comprise a fourth subset in which each detectable probe can comprise click functional group C1', C2', C3', or C4' and fluorescent label Fy, wherein Fr, Fg, Fb and Fy can different.

Also provided herein are methods for analyzing a target nucleic acid in a tissue sample, comprising (a) contacting a tissue sample with a first probe (e.g., first reading probe) comprising click functional group C1 and a second probe (e.g., second reading probe) comprising click functional group C2, wherein the tissue sample comprises a template derived from a target nucleic acid in the tissue sample, the template is embedded in and/or linked to the tissue sample, wherein the template comprises (i) a first adaptor and a first target polynucleotide adjacent to the first adaptor and (ii) a second adaptor and a second target polynucleotide adjacent to the second adaptor, and wherein the first probe (e.g., first reading probe) hybridizes to the first adaptor and the second probe (e.g., second reading probe) hybridizes to the second adaptor; (b) contacting the tissue sample with a first detectable probe comprising click functional group C1' and a first fluorescent label, wherein the first detectable probe hybridizes to the first target polynucleotide adjacent to the first adaptor, thereby juxtaposing click functional groups C1 and C1'; (c) reacting click functional group C1 with click functional group C1', thereby ligating the first probe (e.g., first reading probe) to the first detectable probe to form a first ligated product hybridized on the template, wherein the first ligated product comprises the first fluorescent label; and (d) imaging the tissue sample to detect a first fluorescent signal from the first fluorescent label, wherein the first fluorescent signal is indicative of a sequence of the first target polynucleotide.

In some embodiments, the methods can further comprise contacting the tissue sample with a second detectable probe comprising click functional group C2' and a second fluorescent label, wherein the second detectable probe can hybridize to the second target polynucleotide adjacent to the second adaptor, thereby juxtaposing click functional groups C2 and C2'. In some embodiments, the methods can further comprise reacting click functional group C2 with click functional group C2', thereby ligating the second probe (e.g., second reading probe) to the second detectable probe to form a second ligated product hybridized on the template, wherein the second ligated product can comprise the second fluorescent label. In some embodiments, the methods can further comprise imaging the tissue sample to detect a second fluorescent signal from the second fluorescent label, wherein the second fluorescent signal can be indicative of a sequence of the second target polynucleotide.

In any of the preceding embodiments, the template can comprise a concatemer comprising a plurality of monomeric units. In any of the preceding embodiments, the first target polynucleotide and/or the second target polynucleotide can comprise a barcode sequence that identifies a sequence of the target nucleic acid. In any of the preceding embodiments, the template can be produced through rolling circle amplification (RCA) of a circular construct directly or indirectly hybridized to the target nucleic acid in the tissue sample. In some embodiments, the RCA can comprise a linear RCA, a branched RCA, a dendritic RCA, or any combination thereof.

In any of the preceding embodiments, the tissue sample can be a non-homogenized tissue sample. In any of the preceding embodiments, the tissue sample can be an intact tissue sample. In any of the preceding embodiments, the tissue sample can be permeablized and/or fixed. In any of the preceding embodiments, the target nucleic acid can comprise an RNA sequence, e.g., an mRNA sequence.

Also provided herein are methods for analyzing a target nucleic acid in a tissue sample, comprising (a) contacting a tissue sample with a first probe (e.g., first reading probe) comprising click functional group C1 and a second probe (e.g., second reading probe) comprising click functional group C2, wherein the tissue sample comprises a first nucleic acid sequence and a second nucleic acid sequence derived from a first target nucleic acid and a second target nucleic acid, respectively, in the tissue sample, the first and second nucleic acid sequences are embedded in and/or linked to the tissue sample, wherein the first nucleic acid sequence comprises a first adaptor and a first target polynucleotide adjacent to the first adaptor and the second nucleic acid sequence comprises a second adaptor and a second target polynucleotide adjacent to the second adaptor, and wherein the first probe (e.g., first reading probe) hybridizes to the first adaptor and the second probe (e.g., second reading probe) hybridizes to the second adaptor; (b) contacting the tissue sample with a first detectable probe comprising click functional group C1' and a first fluorescent label, wherein the first detectable probe hybridizes to the first target polynucleotide adjacent to the first adaptor, thereby juxtaposing click functional groups C1 and C1'; (c) reacting click functional group C1 with click functional group C1', thereby ligating the first probe (e.g., first reading probe) to the first detectable probe to form a first ligated product hybridized on the first nucleic acid sequence, wherein the first ligated product comprises the first fluorescent label; and (d) imaging the tissue sample to detect a first fluorescent signal from the first fluorescent label, wherein the first fluorescent signal is indicative of a sequence of the first target polynucleotide.

In some embodiments, the methods can further comprise contacting the tissue sample with a second detectable probe comprising click functional group C2' and a second fluorescent label, wherein the second detectable probe can hybridize to the second target polynucleotide adjacent to the second adaptor, thereby juxtaposing click functional groups C2 and C2'. In some embodiments, the methods can further comprise reacting click functional group C2 with click functional group C2', thereby ligating the second probe (e.g., second reading probe) to the second detectable probe to form a second ligated product hybridized on the second nucleic acid sequence, wherein the second ligated product can comprise the second fluorescent label. In some embodiments, the methods can further comprise imaging the tissue sample to detect a second fluorescent signal from the second fluorescent label, wherein the second fluorescent signal can be indicative of a sequence of the second target polynucleotide.

In any of the preceding embodiments, the first and second nucleic acid sequences can each comprise a concatemer comprising a plurality of monomeric units. In any of the preceding embodiments, the first and second nucleic acid sequences can be produced through rolling circle amplification (RCA) of a circular construct directly or indirectly hybridized to the first and second target nucleic acid, respectively, in the tissue sample.

Also provided herein are compositions comprising a hybridization mix comprising a first nucleic acid sequence, a second nucleic acid sequence, a first probe (e.g., first reading probe) comprising click functional group C1, and a second probe (e.g., second reading probe) comprising click functional group C2, to form a hybridization mix, wherein the first nucleic acid sequence comprises a first adaptor and a first target polynucleotide adjacent to the first adaptor, the second nucleic acid sequence comprises a second adaptor and a second target polynucleotide adjacent to the second adaptor, the first probe (e.g., first reading probe) hybridizes to the first adaptor, and the second probe (e.g., second reading probe) hybridizes to the second adaptor; and a first detectable probe comprising click functional group C1' and a first detectable label, wherein the first detectable probe hybridizes to the first target polynucleotide adjacent to the first adaptor, thereby juxtaposing click functional groups C1 and C1'.

Also provided herein are compositions comprising a hybridization mix comprising a first nucleic acid sequence, a second nucleic acid sequence, a first probe (e.g., first reading probe) comprising click functional group C1, and a second probe (e.g., second reading probe) comprising click functional group C2, to form a hybridization mix, wherein the first nucleic acid sequence comprises a first adaptor and a first target polynucleotide adjacent to the first adaptor, the second nucleic acid sequence comprises a second adaptor and a second target polynucleotide adjacent to the second adaptor, the first probe (e.g., first reading probe) hybridizes to the first adaptor, and the second probe (e.g., second reading probe) hybridizes to the second adaptor; and a plurality of detectable probes of formula $N_xB_yN_z$, wherein N is a degenerate base and B is an interrogatory base, x, y, and z are integers independent of each other, wherein x is 0 or greater, y is 1 or greater, and z is 0 or greater, and wherein each of the plurality of detectable probes comprises click functional group C1' and a fluorescent label, wherein at least one of the plurality of detectable probes hybridizes to the first target polynucleotide adjacent to the first adaptor, thereby juxtaposing click functional groups C1 and C1'. In some embodiments, two or more of the plurality of detectable probes can comprise different fluorescent labels.

In any of the preceding embodiments, the first and second nucleic acid sequences can be in the same nucleic acid molecule. In any of the preceding embodiments, the first and second nucleic acid sequences can be in different nucleic acid molecules.

Also provided herein are methods for analyzing a sample, comprising (a) contacting the sample with a first probe and a second probe, wherein the sample comprises a first nucleic acid sequence and a second nucleic acid sequence, wherein the first nucleic acid sequence comprises a first adaptor sequence and a first target polynucleotide sequence adjacent to the first adaptor sequence, and the second nucleic acid sequence comprises a second adaptor sequence and a second target polynucleotide sequence adjacent to the second adaptor sequence, and the first probe comprises click functional group C1 and hybridizes to the first adaptor sequence, and the second probe comprises click functional group C2 and hybridizes to the second adaptor sequence; (b) contacting the sample with a first detectable probe, wherein the first detectable probe comprises click functional group C1' and hybridizes to the first target polynucleotide sequence, thereby juxtaposing C1 and C1'; (c) reacting C1 with C1' in a click reaction, thereby ligating the first probe to the first detectable probe to form a first ligated product hybridized to the first nucleic acid sequence, wherein the click reaction between C1 and C1' is orthogonal to a click reaction involving C2; and (d) detecting a signal associated with the first ligated product, wherein the signal is indicative of a sequence of interest in the first target polynucleotide sequence.

Also provided herein are methods for analyzing a sample, comprising (a) contacting the sample with a first probe and a second probe, wherein the sample comprises a first nucleic acid sequence and a second nucleic acid sequence, wherein the first nucleic acid sequence comprises a first adaptor sequence and a first target polynucleotide sequence adjacent to the first adaptor sequence, and the second nucleic acid sequence comprises a second adaptor sequence and a second target polynucleotide sequence adjacent to the second adaptor sequence, and the first probe comprises click functional group C1 and hybridizes to the first adaptor sequence, and the second probe comprises click functional group C2 and hybridizes to the second adaptor sequence; (b) contacting the sample with a plurality of first detectable probes of formula $N_xB_yN_z$, wherein N is a degenerate base and B is an interrogatory base, x, y, and z are integers independent of each other, x is 0 or greater, y is 1 or 2, and z is 0 or greater, wherein each of the plurality of first detectable probes comprises: (i) click functional group C1', (ii) interrogatory region $B_y$, and (iii) a detectable label corresponding to one or more different interrogatory regions in the plurality of first detectable probes, and wherein the first detectable probe comprising the interrogatory region complementary to a corresponding sequence of interest in the first target polynucleotide sequence hybridizes to the first nucleic acid sequence, thereby juxtaposing C1 of the first probe and C1' of the first detectable probe; (c) reacting C1 with C1' in a click reaction, thereby ligating the first probe to the first detectable probe to form a first ligated product hybridized to the first nucleic acid sequence; (d) detecting a signal associated with the first ligated product, wherein the signal is indicative of the sequence of interest in the first target polynucleotide sequence; (e) contacting the sample with a plurality of second detectable probes of formula $N_aB_bN_e$, wherein N is a degenerate base and B is an interrogatory base, a, b, and c are integers independent of each other, a is 0 or greater, b is 1 or 2, and c is 0 or greater, wherein each of the plurality of second detectable probes comprises: (i) click functional group C2', (ii) interrogatory region Bb, and (iii) a detectable label corresponding to one or more different interrogatory regions in the plurality of second detectable probes, and wherein the second detectable probe comprising the interrogatory region complementary to a corresponding sequence of interest in the second target polynucleotide sequence hybridizes to the second nucleic acid sequence, thereby juxtaposing C2 of the second probe and C2' of the second detectable probe; (f) reacting C2 with C2' in a click reaction, thereby ligating the second probe to the second detectable probe to form a second ligated product hybridized to the second nucleic acid sequence, wherein the click reaction between C1 and C1' is orthogonal to the click reaction between C2 and C2'; and (g) detecting a signal associated with the second ligated product, wherein the signal is indicative of the sequence of interest in the second target polynucleotide sequence.

BRIEF DESCRIPTION OF THE DRAWINGS

FIG. 7 shows an example of the scalability and acquisition time of click chemistry bioconjugation disclosed herein in polynucleotide sequencing, such as in an in situ assay.

DETAILED DESCRIPTION

Figure 1:
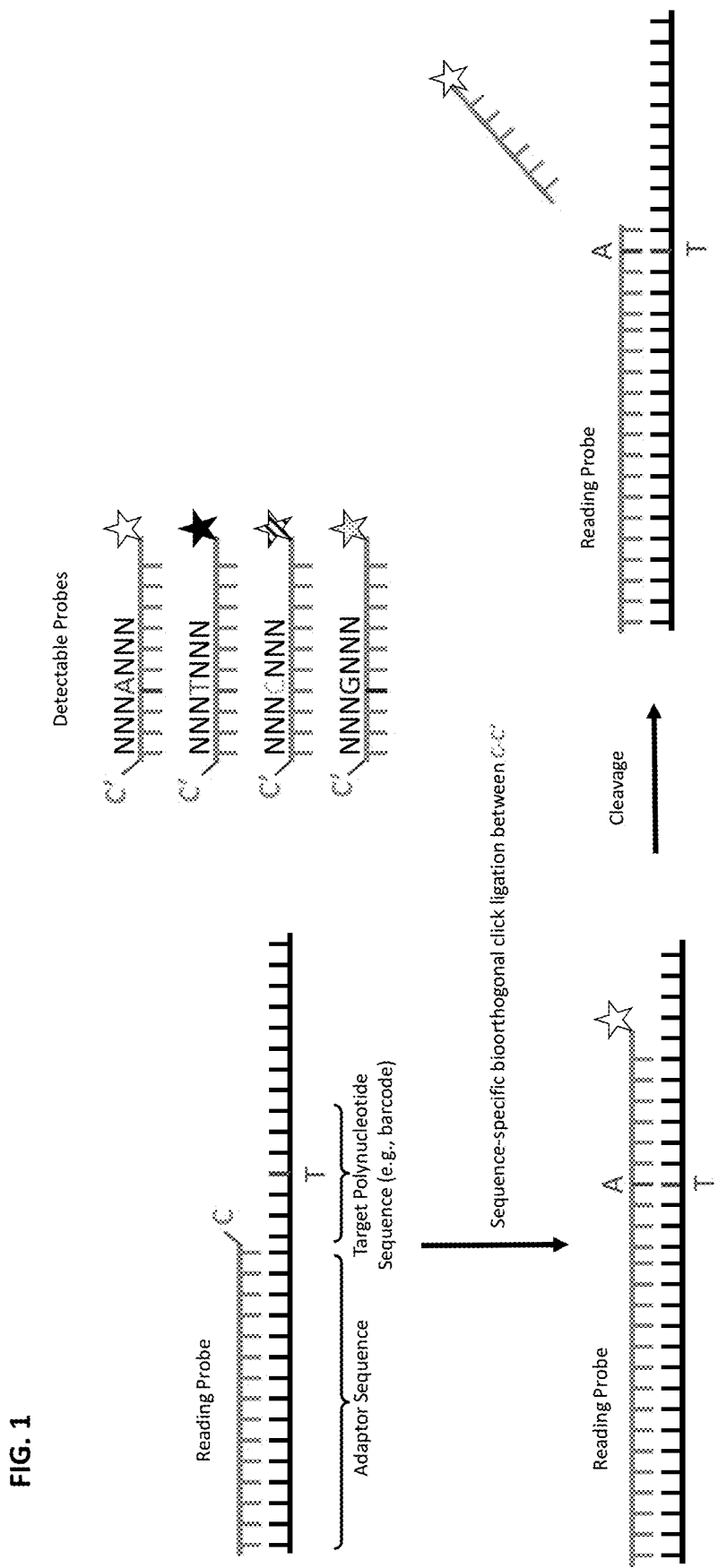
FIG. 1 shows sequencing of an unknown polynucleotide sequence (such as a barcode sequence) via the bioconjugation of a fluorescently labeled detectable probe to a probe (e.g., reading probe) hybridized to an adaptor sequence (e.g., a known constant region) of the polynucleotide.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

One significant bottle neck of in situ technologies with microscopy readout is incubation and imaging time. Sequencing approaches rely on enzymatic activities (often that of ligases) that require long incubation times (for example, four hours) to complete each readout cycle. To analyze 1,000 genes by in situ sequencing or other multiplexed approaches, acquisition times of 24 hours or greater may be required. When gene throughput increases to 10,000, traditional sequential hybridization-based approaches may require imaging times in the scale of days. For example, with traditional sequential hybridization approaches, a microscope can typically render only three to four channels at any given time, so many cycles are required to render many genes (for example, 81 cycles for 10,000 genes). There is thus a need to significantly decrease the acquisition time for in situ technologies. Click chemistry reactions are much faster than hybridization, which in turn is much faster than ligation. However, click chemistry reactions are not able to conjugate molecules in a template-specific way.

The compositions, systems, and methods provided herein overcome at least some of these limitations and provide an improved, faster way to perform in situ sequencing and analysis. To reduce incubation and acquisition time, click chemistry reactions that are intrinsically faster than hybridization or enzymatic reactions are used to conjugate fluorescent molecules to readout sequences in tissue of interest. To enable template specificity in click chemistry reactions, the methods use custom-designed readout sequences that enable the hybridization of complementary probes and the conjugation of detectable moieties (e.g., fluorescent molecules) onto these probes. Template specificity is also achieved through the use of multiple types of click chemistry reactions such that bonds are differentially catalyzed. In this manner, conjugation can be multiplexed and selective to particular complementary probes. Combinations of chemistries and orientations can also be used to increase multiplexing. In addition, all complementary probes (e.g., reading probes) can be hybridized simultaneously or in large pools. In this manner, the provided methods do not increase hybridization time, typically one of the longest step in in situ technologies.

Provided herein are methods of sequencing using click chemistry bioconjugation. In some embodiments, templates comprising target polynucleotide sequences on the same or different molecules are contacted with and hybridize to probes (e.g., reading probes) comprising click functional groups. In some embodiments, click functional groups vary across probes. In some embodiments, probes comprising fluorescent labels and a first set of click functional groups are contacted with and hybridize to complementary target polynucleotide sequences. In some embodiments, the probes comprise one or more interrogatory bases flanked by zero or more degenerate bases. In some embodiments, only a first set of probes with compatible click functional groups are conjugated via a click reaction, optionally a bio-orthogonal reaction. In some embodiments, the click reactions (e.g., click chemistry 1 through 4 shown in FIG. 2B) are mutually orthogonal in that components (e.g., functional groups) of a first reaction react together in high yield in the presence of components (e.g., functional groups) of a second reaction, without affecting the second reaction and/or being affected by components of the second reaction. In some embodiments, the reactions are bio-orthogonal in that the reaction occur in high yield and in the presence of one or more biomolecules, such as proteins and nucleic acids. For instance, the bio-orthogonal conjugation disclosed herein can proceed fast and reliably in chemically complex and demanding environments (e.g., in a tissue section), in the presence of a multitude of biofunctionalities without perturbing their native properties and/or activities.

In some embodiments, fluorescent signals from the conjugated fluorescent labels are detected and indicative of sequences of a first set of target polynucleotide sequences. In some embodiments, additional probes with different click functional groups and fluorescent labels are provided for different target polynucleotide sequences. Also provided herein are compositions comprising a hybridization mix of templates, probes with click functional groups, and probes with click functional groups and fluorescent labels.

Overall, the methods herein provide a sequencing technology, e.g., an in situ sequencing technology, with one or more or all of the following advantages: low non-specific reactivity; no reaction in solution, especially at low concentrations; rapid reaction upon hybridization with a template, especially at high effective concentration; single base pair discrimination; possible multiplexing with mutually orthogonal reactions; and removable fluorophores.

II. Samples, Analytes, and Target Sequences

A method disclosed herein may be used to process and/or analyze any analyte(s) of interest, for example, for detecting the analyte(s) in situ in a sample of interest. A target nucleic acid sequence for a probe (e.g., a reading probe) and detectable probes (e.g., fluorescently labeled probes) comprising a click functional group as disclosed herein may be or be comprised in an analyte (e.g., a nucleic acid analyte, such as genomic DNA, mRNA transcript, or cDNA, or a product thereof, e.g., an extension or amplification product, such as an RCA product) and/or may be or be comprised in a labelling agent for one or more analytes (e.g., a nucleic acid analyte or a non-nucleic acid analyte) in a sample or a product of the labelling agent. Exemplary analytes and labelling agents are described below.

A. Samples

A sample disclosed herein can be or derived from any biological sample. Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. In addition to the subjects described above, a biological sample can be obtained from a prokaryote such as a bacterium, an archaea, a virus, or a viroid. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface.

Cell-free biological samples can include extracellular polynucleotides. Extracellular polynucleotides can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

Biological samples can include analytes (e.g., protein, RNA, and/or DNA) embedded in a 3D matrix. In some embodiments, amplicons (e.g., rolling circle amplification products) derived from or associated with analytes (e.g., protein, RNA, and/or DNA) can be embedded in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

In some embodiments, a substrate herein can be any support that is insoluble in aqueous liquid and which allows for positioning of biological samples, analytes, features, and/or reagents (e.g., probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

(i) Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 µm thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 µm. Thicker sections can also be used if desired or convenient, e.g., at least 70, 80, 90, or 100 µm or more. Typically, the thickness of a tissue section is between 1-100 µm, 1-50 µm, 1-30 µm, 1-25 µm, 1-20 µm, 1-15 µm, 1-10 µm, 2-8 µm, 3-7 µm, or 4-6 µm, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

(ii) Freezing

In some embodiments, the biological sample (e.g., a tissue section as described above) can be prepared by deep freezing at a temperature suitable to maintain or preserve the integrity (e.g., the physical characteristics) of the tissue structure. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

(iii) Fixation and Postfixation

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

In some embodiments, the methods provided herein comprises one or more post-fixing (also referred to as postfixation) steps. In some embodiments, one or more post-fixing step is performed after contacting a sample with a polynucleotide disclosed herein, e.g., one or more probes such as a circular or padlock probe. In some embodiments, one or more post-fixing step is performed after a hybridization complex comprising a probe and a target is formed in a sample. In some embodiments, one or more post-fixing step is performed prior to a ligation reaction disclosed herein, such as the ligation to circularize a padlock probe.

In some embodiments, one or more post-fixing step is performed after contacting a sample with a binding or labelling agent (e.g., an antibody or antigen binding fragment thereof) for a non-nucleic acid analyte such as a protein analyte. The labelling agent can comprise a nucleic acid molecule (e.g., reporter oligonucleotide) comprising a sequence corresponding to the labelling agent and therefore corresponds to (e.g., uniquely identifies) the analyte. In some embodiments, the labelling agent can comprise a reporter oligonucleotide comprising one or more barcode sequences.

A post-fixing step may be performed using any suitable fixation reagent disclosed herein, for example, 3% (w/v) paraformaldehyde in DEPC-PBS.

(iv) Embedding

As an alternative to paraffin embedding described above, a biological sample can be embedded in any of a variety of other embedding materials to provide structural substrate to the sample prior to sectioning and other handling steps. In some cases, the embedding material can be removed e.g., prior to analysis of tissue sections obtained from the sample. Suitable embedding materials include, but are not limited to, waxes, resins (e.g., methacrylate resins), epoxies, and agar.

In some embodiments, the biological sample can be embedded in a matrix (e.g., a hydrogel matrix). Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other hydrogel-formation method known in the art.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 μm to about 2 mm.

Additional methods and aspects of hydrogel embedding of biological samples are described for example in Chen et al., *Science* 347(6221):543-548, 2015, the entire contents of which are incorporated herein by reference.

(v) Staining

To facilitate visualization, biological samples can be stained using a wide variety of stains and staining techniques. In some embodiments, for example, a sample can be stained using any number of stains, including but not limited to, acridine orange, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, propidium iodide, rhodamine, or safranine.

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Methods of destaining or discoloring a biological sample are known in the art, and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

(vi) Isometric Expansion

In some embodiments, a biological sample embedded in a matrix (e.g., a hydrogel) can be isometrically expanded. Isometric expansion methods that can be used include hydration, a preparative step in expansion microscopy, as described in Chen et al., *Science* 347(6221):543-548, 2015.

Isometric expansion can be performed by anchoring one or more components of a biological sample to a gel, followed by gel formation, proteolysis, and swelling. In some embodiments, analytes in the sample, products of the analytes, and/or probes associated with analytes in the sample can be anchored to the matrix (e.g., hydrogel). Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with probes disclosed herein.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, MA), Label-IT Amine (available from MirusBio, Madison, WI) and Label X (described for example in Chen et al., Nat. Methods 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(vii) Crosslinking and De-Crosslinking

In some embodiments, the biological sample is reversibly cross-linked prior to or during an in situ assay. In some aspects, the analytes, polynucleotides and/or amplification product (e.g., amplicon) of an analyte or a probe bound thereto can be anchored to a polymer matrix. For example, the polymer matrix can be a hydrogel. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix. In some embodiments, a modified probe comprising oligo dT may be used to bind to mRNA molecules of interest, followed by reversible crosslinking of the mRNA molecules.

In some embodiments, the biological sample is immobilized in a hydrogel via cross-linking of the polymer material that forms the hydrogel. Cross-linking can be performed chemically and/or photochemically, or alternatively by any other hydrogel-formation method known in the art. A hydrogel may include a macromolecular polymer gel including a network. Within the network, some polymer chains can optionally be cross-linked, although cross-linking does not always occur.

In some embodiments, a hydrogel can include hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after probes are provided to the sample. For example, hydrogel formation can be performed on the substrate already containing the probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, transposase, ligase, proteinase K, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labelling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

In some embodiments, a method disclosed herein comprises de-crosslinking the reversibly cross-linked biological sample. The de-crosslinking does not need to be complete. In some embodiments, only a portion of crosslinked molecules in the reversibly cross-linked biological sample are de-crosslinked and allowed to migrate.

(viii) Tissue Permeabilization and Treatment

In some embodiments, a biological sample can be permeabilized to facilitate transfer of analytes out of the sample, and/or to facilitate transfer of species (such as probes) into the sample. If a sample is not permeabilized sufficiently, the amount of analyte captured from the sample may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., Method Mol. Biol. 588:63-66, 2010, the entire contents of which are incorporated herein by reference. Any suitable method for sample permeabilization can generally be used in connection with the samples described herein.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. Non-chemical permeabilization methods are known in the art. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to opening up DNA in a cell for hybridization by a probe. For example, proteinase K treatment may be used to free up DNA with proteins bound thereto.

(ix) Selective Enrichment of RNA Species

In some embodiments, where RNA is the analyte, one or more RNA analyte species of interest can be selectively enriched. For example, one or more species of RNA of interest can be selected by addition of one or more oligonucleotides to the sample. In some embodiments, the additional oligonucleotide is a sequence used for priming a reaction by an enzyme (e.g., a polymerase). For example, one or more primer sequences with sequence complementarity to one or more RNAs of interest can be used to amplify the one or more RNAs of interest, thereby selectively enriching these RNAs.

In some embodiments, an oligonucleotide with sequence complementarity to the complementary strand of captured RNA (e.g., cDNA) can bind to the cDNA. For example, biotinylated oligonucleotides with sequence complementary to one or more cDNA of interest binds to the cDNA and can be selected using biotinylation-strepavidin affinity using any of a variety of methods known to the field (e.g., streptavidin beads).

Alternatively, one or more species of RNA can be down-selected (e.g., removed) using any of a variety of methods. For example, probes can be administered to a sample that selectively hybridize to ribosomal RNA (rRNA), thereby reducing the pool and concentration of rRNA in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, *BMC Genomics*, 15 401, (2014), the entire contents of which are incorporated herein by reference). Furthermore, hydroxyapatite chromatography can remove abundant species (e.g., rRNA) (see, e.g., Vandernoot, V. A., cDNA normalization by hydroxyapatite chromatography to enrich transcriptome diversity in RNA-seq applications, Biotechniques, 53(6) 373-80, (2012), the entire contents of which are incorporated herein by reference).

A biological sample may comprise one or a plurality of analytes of interest. Methods for performing multiplexed assays to analyze two or more different analytes in a single biological sample are provided.

B. Analytes

The methods and compositions disclosed herein can be used to detect and analyze a wide variety of different analytes. In some aspects, an analyte can include any biological substance, structure, moiety, or component to be analyzed. In some aspects, a target disclosed herein may similarly include any analyte of interest. In some examples, a target or analyte can be directly or indirectly detected.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis, and/or allow access of one or more reagents (e.g., probes for analyte detection) to the analytes in the cell or cell compartment or organelle.

The analyte may include any biomolecule or chemical compound, including a macromolecule such as a protein or peptide, a lipid or a nucleic acid molecule, or a small molecule, including organic or inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for a nucleic acid analyte) and may lead directly to the generation of a RCA template (e.g. a padlock or other circularizable probe). Alternatively, the specific binding partner may be coupled to a nucleic acid, which may be detected using an RCA strategy, e.g. in an assay which uses or generates a circular nucleic acid molecule which can be the RCA template.

Analytes of particular interest may include nucleic acid molecules, such as DNA (e.g. genomic DNA, mitochondrial DNA, plastid DNA, viral DNA, etc.) and RNA (e.g. mRNA, microRNA, rRNA, snRNA, viral RNA, etc.), and synthetic and/or modified nucleic acid molecules, (e.g. including nucleic acid domains comprising or consisting of synthetic or modified nucleotides such as LNA, PNA, morpholino, etc.), proteinaceous molecules such as peptides, polypeptides, proteins or prions or any molecule which includes a protein or polypeptide component, etc., or fragments thereof, or a lipid or carbohydrate molecule, or any molecule which comprise a lipid or carbohydrate component. The analyte may be a single molecule or a complex that contains two or more molecular subunits, e.g. including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA, e.g. interactions between proteins and nucleic acids, e.g. regulatory factors, such as transcription factors, and DNA or RNA.

(i) Endogenous Analytes

In some embodiments, an analyte herein is endogenous to a biological sample and can include nucleic acid analytes and non-nucleic acid analytes. Methods and compositions disclosed herein can be used to analyze nucleic acid analytes (e.g., using a nucleic acid probe or probe set that directly or indirectly hybridizes to a nucleic acid analyte) and/or non-nucleic acid analytes (e.g., using a labelling agent that comprises a reporter oligonucleotide and binds directly or indirectly to a non-nucleic acid analyte) in any suitable combination.

Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte is inside a cell or on a cell surface, such as a transmembrane analyte or one that is attached to the cell membrane. In some embodiments, the analyte can be an organelle (e.g., nuclei or mitochondria). In some embodiments, the analyte is an extracellular analyte, such as a secreted analyte. Exemplary analytes include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Examples of nucleic acid analytes include DNA analytes such as single-stranded DNA (ssDNA), double-stranded DNA (dsDNA), genomic DNA, methylated DNA, specific methylated DNA sequences, fragmented DNA, mitochondrial DNA, in situ synthesized PCR products, and RNA/DNA hybrids. The DNA analyte can be a transcript of another nucleic acid molecule (e.g., DNA or RNA such as mRNA) present in a tissue sample.

Examples of nucleic acid analytes also include RNA analytes such as various types of coding and non-coding RNA. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. The RNA analyte can be a transcript of another nucleic acid molecule (e.g., DNA or RNA such as viral RNA) present in a tissue sample. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaRNAs), and the long ncRNAs such as Xist and HOTAIR. The RNA can be small (e.g., less than 200 nucleic acid bases in length) or large (e.g., RNA greater than 200 nucleic acid bases in length). Examples of small RNAs include 5.8S ribosomal RNA (rRNA), 5S rRNA, tRNA, miRNA, siRNA, snoRNAs, piRNA, tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In some embodiments described herein, an analyte may be a denatured nucleic acid, wherein the resulting denatured nucleic acid is single-stranded. The nucleic acid may be denatured, for example, optionally using formamide, heat, or both formamide and heat. In some embodiments, the nucleic acid is not denatured for use in a method disclosed herein.

In certain embodiments, an analyte can be extracted from a live cell. Processing conditions can be adjusted to ensure that a biological sample remains live during analysis, and analytes are extracted from (or released from) live cells of the sample. Live cell-derived analytes can be obtained only once from the sample, or can be obtained at intervals from a sample that continues to remain in viable condition.

Methods and compositions disclosed herein can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

In any embodiment described herein, the analyte comprises a target sequence. In some embodiments, the target sequence may be endogenous to the sample, generated in the sample, added to the sample, or associated with an analyte in the sample. In some embodiments, the target sequence is a single-stranded target sequence (e.g., a sequence in a rolling circle amplification product). In some embodiments, the analytes comprise one or more single-stranded target sequences. In one aspect, a first single-stranded target sequence is not identical to a second single-stranded target sequence. In another aspect, a first single-stranded target sequence is identical to one or more second single-stranded target sequence. In some embodiments, the one or more second single-stranded target sequence is comprised in the same analyte (e.g., nucleic acid) as the first single-stranded target sequence. Alternatively, the one or more second single-stranded target sequence is comprised in a different analyte (e.g., nucleic acid) from the first single-stranded target sequence.

(ii) Labelling Agents

In some embodiments, provided herein are methods and compositions for analyzing endogenous analytes (e.g., RNA, ssDNA, and cell surface or intracellular proteins and/or metabolites) in a sample using one or more labelling agents. In some embodiments, an analyte labelling agent may include an agent that interacts with an analyte (e.g., an endogenous analyte in a sample). In some embodiments, the labelling agents can comprise a reporter oligonucleotide that is indicative of the analyte or portion thereof interacting with the labelling agent. For example, the reporter oligonucleotide may comprise a barcode sequence that permits identification of the labelling agent. In some cases, the sample contacted by the labelling agent can be further contacted with a probe (e.g., a single-stranded probe sequence), that hybridizes to a reporter oligonucleotide of the labelling agent, in order to identify the analyte associated with the labelling agent. In some embodiments, the analyte labelling agent comprises an analyte binding moiety and a labelling agent barcode domain comprising one or more barcode sequences, e.g., a barcode sequence that corresponds to the analyte binding moiety and/or the analyte. An analyte binding moiety barcode includes to a barcode that is associated with or otherwise identifies the analyte binding moiety. In some embodiments, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein.

In some embodiments, the method comprises one or more post-fixing (also referred to as post-fixation) steps after contacting the sample with one or more labelling agents.

In the methods and systems described herein, one or more labelling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

In some embodiments, an analyte binding moiety may include any molecule or moiety capable of binding to an analyte (e.g., a biological analyte, e.g., a macromolecular constituent). A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In some embodiments, an analyte binding moiety includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte labelling agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte labelling agents are the same. In some embodiments in which the plurality of analytes includes a single species of analyte, the analyte binding moieties of the plurality of analyte labelling agents are the different (e.g., members of the plurality of analyte labelling agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide.

In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing, such as an adaptor sequence, a unique molecular identifier (UMI) sequence, a sequencer specific flow cell attachment sequence (such as an P5, P7, or partial P5 or P7 sequence), a primer or primer binding sequence, a sequencing primer or primer biding sequence (such as an R1, R2, or partial R1 or R2 sequence).

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to a first oligonucleotide that is complementary (e.g., hybridizes) to a sequence of the reporter oligonucleotide.

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (i.e., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte labelling agent comprising an analyte binding moiety that binds to the cell surface protein and an analyte binding moiety barcode that identifies that analyte binding moiety. Results of protein analysis in a sample (e.g., a tissue sample or a cell) can be associated with DNA and/or RNA analysis in the sample.

(iii) Products of Endogenous Analyte and/or Labelling Agent

In some embodiments, provided herein are methods and compositions for analyzing one or more products of an endogenous analyte and/or a labelling agent in a biological sample. In some embodiments, an endogenous analyte (e.g., a viral or cellular DNA or RNA) or a product (e.g., a hybridization product, a ligation product, an extension product (e.g., by a DNA or RNA polymerase), a replication product, a transcription/reverse transcription product, and/or an amplification product such as a rolling circle amplification (RCA) product) thereof is analyzed. In some embodiments, a labelling agent that directly or indirectly binds to an analyte in the biological sample is analyzed. In some embodiments, a product (e.g., a hybridization product, a ligation product, an extension product (e.g., by a DNA or RNA polymerase), a replication product, a transcription/reverse transcription product, and/or an amplification product such as a rolling circle amplification (RCA) product) of a labelling agent that directly or indirectly binds to an analyte in the biological sample is analyzed.

III. Methods for Analysis Using Click Chemistry Bioconjugation

Provided herein are compositions, systems, and methods for identifying a nucleic acid sequence of each of one or more target polynucleotides. In some embodiments, the nucleic acid sequence varies across the one or more target polynucleotides. In some embodiments, the nucleic acid sequence comprises a DNA sequence of a gene. In some embodiments, the nucleic acid sequence comprises an RNA sequence of a gene. In some embodiments, the nucleic acid sequence is a barcode sequence. In some embodiments, the barcode sequence uniquely identifies another nucleic acid sequence, such as an RNA molecule (e.g., mRNA). In some embodiments, the barcode sequence comprises two or more sub-barcode sequences, e.g., dinucleotide sequences which can be detected in sequential detectable probe hybridization and ligation cycles in a sequencing-by-ligation approach disclosed herein.

In some embodiments, the methods provide for in situ sequencing of a sample. In some embodiments, the sample is a non-homogenized tissue sample. In some embodiments, the sample is an intact tissue sample. In some embodiments, the sample is fixed. In some embodiments, the target nucleic acid is in a cell in the sample. In some embodiments, the cell is permeabilized. In some embodiments, the transcriptome of a single cell or a cell population is sequenced.

A. Target Nucleic Acids and Amplification Thereof

A target sequence (e.g., a target polynucleotide) for a probe disclosed herein may be comprised in any analyte disclose herein, including an endogenous analyte (e.g., a viral or cellular nucleic acid), a labelling agent, or a product of an endogenous analyte and/or a labelling agent.

In some embodiments, each of the one or more target polynucleotides has a length of between at or about 5 and at or about 100 nucleotides, inclusive. In some embodiments, each of the one or more target polynucleotides has a length of between at or about 5 and at or about 75 nucleotides, inclusive. In some embodiments, each of the one or more target polynucleotides has a length of between at or about 5 and at or about 50 nucleotides, inclusive. In some embodiments, each of the one or more target polynucleotides has a length of between at or about 5 and at or about 25 nucleotides, inclusive. In some embodiments, each of the one or more target polynucleotides has a length of between at or about 5 and at or about 10 nucleotides, inclusive. In some embodiments, each of the one or more target polynucleotides has a length of between at or about 10 and at or about 100 nucleotides, inclusive. In some embodiments, each of the one or more target polynucleotides has a length of between at or about 10 and at or about 75 nucleotides, inclusive. In some embodiments, each of the one or more target polynucleotides has a length of between at or about 10 and at or about 50 nucleotides, inclusive. In some embodiments, each of the one or more target polynucleotides has a length of between at or about 10 and at or about 25 nucleotides, inclusive. In some embodiments, each of the one or more target polynucleotides has a length of between at or about 25 and at or about 100 nucleotides, inclusive. In some embodiments, each of the one or more target polynucleotides has a length of between at or about 25 and at or about 75 nucleotides, inclusive. In some embodiments, each of the one or more target polynucleotides has a length of between at or about 25 and at or about 50 nucleotides, inclusive. In some embodiments, each of the one or more target polynucleotides has a length of between at or about 50 and at or about 100 nucleotides, inclusive. In some embodiments, each of the one or more target polynucleotides has a length of between at or about 50 and at or about 75 nucleotides, inclusive. In some embodiments, each of the one or more target polynucleotides has a length of between at or about 75 and at or about 100 nucleotides, inclusive.

In some embodiments, the one or more target polynucleotides are in different target nucleic acid molecules. In some embodiments, the one or more target polynucleotides are in the same target nucleic acid molecule. In some embodiments, the target nucleic acid is a DNA molecule. In some embodiments, the target nucleic acid is an RNA molecule, for instance a messenger RNA molecule. In some embodiments, a DNA template of an RNA target nucleic acid is produced, and the one or more target polynucleotides are in the DNA template.

In some embodiments, one or more polynucleotides of interest are amplified using rolling circle amplification (RCA) using, e.g., a circular or circularizable construct hybridized to the polynucleotides of interest to generate the target nucleic acid (e.g., comprising a sequence of the polynucleotide(s) of interest or one or more barcode sequences associated with the polynucleotide(s) of interest). In some embodiments, the RCA comprises a linear RCA. In some embodiments, the RCA comprises a branched RCA. In some embodiments, the RCA comprises a dendritic RCA. In some embodiments, the RCA comprises any combination of the foregoing.

Various probes and probe sets can be hybridized to a complementary strand (e.g., an endogenous analyte and/or a labelling agent) to form the circular construct, and each probe may comprise one or more barcode sequences, as described. In some embodiments, the circular construct is formed using ligation. In some embodiments, the circular construct is formed using template primer extension followed by ligation. In some embodiments, the circular construct is formed by providing an insert between ends to be ligated. In some embodiments, the circular construct is formed using a combination of any of the foregoing. In some embodiments, the ligation is a DNA-DNA templated ligation. In some embodiments, the ligation is an RNA-RNA templated ligation. In some embodiments, the ligation is a RNA-DNA templated ligation. In some embodiments, a splint is provided as a template for ligation.

In some embodiments, the circular construct is directly hybridized to the target nucleic acid. In some embodiments, the circular construct is formed from a padlock probe. In some embodiments, the circular construct is formed from a probe or probe set, a gapped padlock probe, a SNAIL (Splint Nucleotide Assisted Intramolecular Ligation) probe set, a PLAYR (Proximity Ligation Assay for RNA) probe set, a PLISH (Proximity Ligation in situ Hybridization) probe set, and RNA-templated ligation probes. For example, various probe or probe sets are capable of DNA-templated ligation, such as from a cDNA molecule. See, e.g., U.S. Pat. No. 8,551,710, which is hereby incorporated by reference in its entirety. In some embodiments, provided herein is a probe or probe set capable of RNA-templated ligation. See, e.g., U.S. Pat. Pub. 2020/0224244 which is hereby incorporated by reference in its entirety. In some embodiments, the circular construct is directly hybridized to the target nucleic acid. In some embodiments, the circular construct is formed from a padlock probe. In some embodiments, the circular construct is formed from a probe or probe set capable of RNA-templated ligation. In some embodiments, the circular construct is formed from a specific amplification of nucleic acids via intramolecular ligation (SNAIL) probe set. See, e.g., U.S. Pat. Pub. 20190055594, which is hereby incorporated by reference in its entirety. In some embodiments, the circular construct is formed from a probe capable of proximity ligation, for instance a proximity ligation assay for RNA (e.g., PLAYR) probe set. In some embodiments, the circular construct is formed from a probe set comprising any combination of the foregoing. See, e.g., U.S. Pat. Pub. 20160108458, which is hereby incorporated by reference in its entirety. In some embodiments, the circular construct is indirectly hybridized to the target nucleic acid. In some embodiments, the circular construct is formed from a probe set capable of proximity ligation, for instance a proximity ligation in situ hybridization (PLISH) probe set. See, e.g., U.S. Pat. Pub. 2020/0224243 which is hereby incorporated by reference in its entirety. The specific probe or probe set design can vary. In some embodiments, the circular construct is formed from a probe set comprising any combination of the foregoing.

In some embodiments, the methods of the invention include the step of performing rolling circle amplification in the presence of a target nucleic acid of interest.

The nature of the ligation reaction depends on the structural components of the polynucleotides used to form the padlock probe. In some embodiments, the ligation involves chemical ligation. In some embodiments, the ligation involves template dependent ligation. In some embodiments, the ligation involves template independent ligation. In some embodiments, the ligation involves enzymatic ligation.

In one embodiment, the polynucleotides comprise complementary docking regions that self-assemble the two or more polynucleotides into a padlock probe that is either ready for ligation because no gaps exist between the docking regions, or is ready for a fill-in process, which will then permit the ligation of the polynucleotides to form the padlock probe. In another embodiment, the docking regions are complementary to a splint primer. In one embodiment, the splint primer is complementary to one pair of docking regions of two polynucleotides. In another embodiment, the splint primer is complementary to two pairs of docking regions. In one aspect of this embodiment, the splint primer has two regions of complementarity to the docking regions of the polynucleotides that form the padlock probe. Typically, a splint probe of this embodiment will comprise a first docking region complementary sequence, a spacer, and a second docking region complementary sequence.

In some embodiments, the enzymatic ligation involves use of a ligase. In some aspects, the ligase used herein comprises an enzyme that is commonly used to join polynucleotides together or to join the ends of a single polynucleotide. In some embodiments, ligation of the polynucleotides is achieved by adding ligase to the hybridization complex to generate a closed nucleic acid circle. An RNA ligase, a DNA ligase, or another variety of ligase can be used to ligate two nucleotide sequences together. In some embodiments, the adding ligase includes adding DNA ligase. The term "ligase" as used herein refers to an enzyme that is commonly used to join polynucleotides together or to join the ends of a single polynucleotide. Ligases include ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases include bacterial ligases such as E. coli DNA ligase, Tth DNA ligase, Thermococcus sp. (strain 9° N) DNA ligase (9° N™ DNA ligase, New England Biolabs), Taq DNA ligase, Ampligase® thermostable DNA ligase (Epicentre® Technologies Corp., part of Illumina®, Madison, Wis.) and phage ligases such as T3 DNA ligase, T4 DNA ligase and T7 DNA ligase and mutants thereof. In some embodiments, the ligase is a T4 RNA ligase. In some embodiments, the ligase is a splintR ligase. In some embodiments, the ligase is a single stranded DNA ligase. In some embodiments, the ligase is a T4 DNA ligase. In some embodiments, the ligase is a ligase that has an DNA-splinted DNA ligase activity. In some embodiments, the ligase is a ligase that has an RNA-splinted DNA ligase activity.

In some embodiments, the ligation herein is a direct ligation. In some embodiments, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, i.e., separated by one or more intervening nucleotides or "gaps". In some embodiments, said ends are not ligated directly to each other, but instead occurs either via the intermediacy of one or more intervening (so-called "gap" or "gap-filling" (oligo) nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo)nucleotide(s) which are complementary to a splint, padlock probe, or target nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide. In some cases, ligation involves ligating the ends of the probe to at least one gap (oligo)nucleotide, such that the gap (oligo)nucleotide becomes incorporated into the resulting polynucleotide. In some embodiments, the ligation herein is preceded by gap filling. In other embodiments, the ligation herein does not require gap filling.

In some embodiments, ligation of the polynucleotides produces polynucleotides with melting temperature higher than that of unligated polynucleotides. Thus, in some aspects, ligation stabilizes the hybridization complex containing the ligated polynucleotides prior to subsequent steps, comprising amplification and detection.

In some aspects, a high fidelity ligase, such as a thermostable DNA ligase (e.g., a Taq DNA ligase), is used. Thermostable DNA ligases are active at elevated temperatures, allowing further discrimination by incubating the ligation at a temperature near the melting temperature (Tm) of the DNA strands. This selectively reduces the concentration of annealed mismatched substrates (expected to have a slightly lower $T_m$ around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

Other types of ligation are also contemplated for use with the disclosed methods. For example, the ligation reaction can be selected from the group consisting of enzymatic ligation, chemical ligation (e.g., click chemistry ligation), and template dependent ligation, or any combination thereof. The nature of the ligation reaction will determine the temperate at which the reaction is performed. In some embodiments, the ligation reaction is performed at a temperature lower than the temperature at which the hybridization complex is formed. In some embodiments, the temperature at which the ligation reaction is performed is between about 10° C. and about 30° C., e.g., about 16° C.

Following formation of the circular probe, an amplification primer is added. The amplification primer is complementary to the target nucleic acid and the circular probe. In some instances, there is a washing step to remove any unbound probes, primers. In some embodiments, the wash is a stringency wash. Washing steps can be performed at any point during the process to remove non-specifically bound probes, probes that have ligated, etc.

In some instances, upon addition of a DNA polymerase in the presence of appropriate dNTP precursors and other cofactors, the amplification primer is elongated by replication of multiple copies of the template. This amplification product can be readily detected by binding to a detectable probe to one or more barcode sequences.

Amplification is next performed. In some embodiments, a product of an endogenous analyte and/or a labelling agent is an amplification product of one or more polynucleotides, for instance, a circular probe or circularizable probe or probe set.

In some embodiments, the amplifying is achieved by performing rolling circle amplification (RCA) to generate the concatemer. In other embodiments, a primer that hybridizes to the circular probe or circularized probe is added and used as such for amplification. In some embodiments, the RCA comprises a linear RCA, a branched RCA, a dendritic RCA, or any combination thereof. In some aspects, during the amplification step, modified nucleotides can be added to the reaction to incorporate the modified nucleotides in the amplification product for additional anchoring of the concatemer.

In some embodiments, the amplification is performed at a temperature between or between about 20° C. and about 60° C. In some embodiments, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some embodiments, upon addition of a DNA polymerase in the presence of appropriate dNTP precursors and other cofactors, a primer is elongated to produce multiple copies of the circular template. The amplification step can utilize isothermal amplification or non-isothermal amplification. In some embodiments, after the formation of the hybridization complex and any subsequent circularization (such as ligation of, e.g., a padlock probe) the circular probe is rolling-circle amplified to generate a DNA concatemer (i.e., amplicon) containing multiple copies of the circular. Techniques for rolling circle amplification (RCA) are known in the art such as linear RCA, a branched RCA, a dendritic RCA, or any combination thereof. (See, e.g., Baner et al, Nucleic Acids Research, 26:5073-5078, 1998; Lizardi et al, Nature Genetics 19:226, 1998; Schweitzer et al. Proc. Natl Acad. Sci. USA 97:101 13-1 19, 2000; Faruqi et al, BMC Genomics 2:4, 2000; Nallur et al, Nucl. Acids Res. 29:e1 18, 2001; Dean et al. Genome Res. 1 1:1095-1099, 2001; Schweitzer et al, Nature Biotech. 20:359-365, 2002; U.S. Pat. Nos. 6,054,274, 6,291,187, 6,323,009, 6,344,329 and 6,368,801). Exemplary polymerases for use in RCA comprise DNA polymerase such phi29 (φ29) polymerase, Klenow fragment, *Bacillus stearothermophilus* DNA polymerase (BST), T4 DNA polymerase, T7 DNA polymerase, or DNA polymerase I. In some aspects, DNA polymerases that have been engineered or mutated to have desirable characteristics can be employed. In some embodiments, the polymerase is phi29 DNA polymerase.

In some embodiments, the RCA template may comprise the target analyte, or a part thereof, where the target analyte is a nucleic acid, or it may be provided or generated as a proxy, or a marker, for the analyte. As noted above, many assays are known for the detection of numerous different analytes, which use a RCA-based detection system, e.g., where the signal is provided by generating a RCA product (RCP) from a circular RCA template which is provided or generated in the assay, and the RCP is detected to detect the analyte. The RCP may thus be regarded as a reporter which is detected to detect the target analyte. However, the RCA template may also be regarded as a reporter for the target analyte; the RCP is generated based on the RCA template, and comprises complementary copies of the RCA template. The RCA template determines the signal which is detected, and is thus indicative of the target analyte. As will be described in more detail below, the RCA template may be a probe, or a part or component of a probe, or may be generated from a probe, or it may be a component of a detection assay (i.e. a reagent in a detection assay), which is used as a reporter for the assay, or a part of a reporter, or signal-generation system. The RCA template used to generate the RCP may thus be a circular (e.g. circularized) reporter nucleic acid molecule, namely from any RCA-based detection assay which uses or generates a circular nucleic acid molecule as a reporter for the assay. Since the RCA template generates the RCP reporter, it may be viewed as part of the reporter system for the assay.

Following amplification, the sequence of the amplicon or a portion thereof, is determined, for example by sequencing, or imaging the amplicon. The sequencing can comprise sequencing by hybridization, sequencing by ligation, and/or fluorescent in situ sequencing, and/or wherein the in situ hybridization comprises sequential fluorescent in situ hybridization.

In particular embodiments, the sequence of the amplicon or a portion thereof, is determined, for example by sequencing using click chemistry bioconjugation of the reading probes and detectable probes disclosed herein. In some embodiments, two or more non-contiguous sequences of the amplicon (e.g., RCP) is detected by sequencing using click chemistry bioconjugation of the reading probes and detectable probes.

B. Reading Probe Design

In some embodiments, each of the one or more target polynucleotides or polynucleotide sequences to be sequenced is adjacent to an adaptor region (e.g., a constant region). In some embodiments, the adaptor regions have the same nucleic acid sequence (e.g., a common adaptor sequence). In some embodiments, the adaptor regions have different nucleic acid sequences. In some embodiments, the nucleic acid sequences of the adaptor regions are known. In some embodiments, the nucleic acid sequences of the adaptor regions have been custom designed.

In some embodiments, each polynucleotide sequence to be analyzed comprises a common adaptor sequence. In some embodiments, the polynucleotide sequences to be analyzed comprise two or more common adaptor sequences. In some embodiments, a subset of the polynucleotide sequences to be analyzed comprise a common adaptor sequence.

In some embodiments, a plurality of target polynucleotides comprise a common adaptor sequence. In some embodiments, a plurality of target polynucleotides comprise two or more common adaptor sequences. In some embodiments, a subset of the plurality of target polynucleotides comprise a common adaptor sequence.

In some embodiments, each of the adaptor regions has a length of between at or about 5 and at or about 100 nucleotides, inclusive. In some embodiments, each of the adaptor regions has a length of between at or about 5 and at or about 75 nucleotides, inclusive. In some embodiments, each of the adaptor regions has a length of between at or about 5 and at or about 50 nucleotides, inclusive. In some embodiments, each of the adaptor regions has a length of between at or about 5 and at or about 25 nucleotides, inclusive. In some embodiments, each of the adaptor regions has a length of between at or about 5 and at or about 10 nucleotides, inclusive. In some embodiments, each of the adaptor regions has a length of between at or about 10 and at or about 100 nucleotides, inclusive. In some embodiments, each of the adaptor regions has a length of between at or about 10 and at or about 75 nucleotides, inclusive. In some embodiments, each of the adaptor regions has a length of between at or about 10 and at or about 50 nucleotides, inclusive. In some embodiments, each of the adaptor regions has a length of between at or about 10 and at or about 25 nucleotides, inclusive. In some embodiments, each of the adaptor regions has a length of between at or about 25 and at or about 100 nucleotides, inclusive. In some embodiments, each of the adaptor regions has a length of between at or about 25 and at or about 75 nucleotides, inclusive. In some embodiments, each of the adaptor regions has a length of between at or about 25 and at or about 50 nucleotides, inclusive. In some embodiments, each of the adaptor regions has a length of between at or about 50 and at or about 100 nucleotides, inclusive. In some embodiments, each of the adaptor regions has a length of between at or about 50 and at or about 75 nucleotides, inclusive. In some embodiments, each of the adaptor regions has a length of between at or about 75 and at or about 100 nucleotides, inclusive. In some embodiments, each of the adaptor regions has a length of less than 5, less than 10, less than 15, less than 20, less than 25, less than 30, less than 35, less than 40, less than 45, less than 50, less than 55, less than 60, less than 65, less than 70, less than 75, less than 80, less than 85, less than 90, less than 95, or less than 100 nucleotides.

In some embodiments, each of the adaptor regions is contacted with a reading probe. In some embodiments, an adaptor region is contacted and hybridized with a reading probe. In some embodiments, an adaptor region is contacted with reading probes sequentially in cycles. In some embodiments, the reading probes have the same nucleic acid sequence. In some embodiments, the reading probes have different nucleic acid sequences. In some embodiments, the nucleic acid sequences of the reading probes are known. In some embodiments, the nucleic acid sequences of the reading probes have been custom designed.

In some embodiments, each of the reading probes has a length of between at or about 5 and at or about 100 nucleotides, inclusive. In some embodiments, each of the reading probes has a length of between at or about 5 and at or about 75 nucleotides, inclusive. In some embodiments, each of the reading probes has a length of between at or about 5 and at or about 50 nucleotides, inclusive. In some embodiments, each of the reading probes has a length of between at or about 5 and at or about 25 nucleotides, inclusive. In some embodiments, each of the reading probes has a length of between at or about 5 and at or about 10 nucleotides, inclusive. In some embodiments, each of the reading probes has a length of between at or about 10 and at or about 100 nucleotides, inclusive. In some embodiments, each of the reading probes has a length of between at or about 10 and at or about 75 nucleotides, inclusive. In some embodiments, each of the reading probes has a length of between at or about 10 and at or about 50 nucleotides, inclusive. In some embodiments, each of the reading probes has a length of between at or about 10 and at or about 25 nucleotides, inclusive. In some embodiments, each of the reading probes has a length of between at or about 25 and at or about 100 nucleotides, inclusive. In some embodiments, each of the reading probes has a length of between at or about 25 and at or about 75 nucleotides, inclusive. In some embodiments, each of the reading probes has a length of between at or about 25 and at or about 50 nucleotides, inclusive. In some embodiments, each of the reading probes has a length of between at or about 50 and at or about 100 nucleotides, inclusive. In some embodiments, each of the reading probes has a length of between at or about 50 and at or about 75 nucleotides, inclusive. In some embodiments, each of the reading probes has a length of between at or about 75 and at or about 100 nucleotides, inclusive.

C. Detectable Probe Design

In some embodiments, a method disclosed herein comprises determining one or more target polynucleotide sequences. In some embodiments, a method disclosed herein comprises determining the sequence of all or a portion of an amplification product. In some embodiments, the analyzing comprises detecting a sequence present in the amplification product. In some aspects, the analysis involves determining the sequence of a portion of the amplification product. In some aspects, the analysis involves determining the sequence of two or more portions of the amplification product, wherein each of the portions may be separate from each other. In some aspects, the analysis involves contacting the target nucleic acid, amplification product or biological sample containing the target nucleic acid or amplification product, with a detectable probe. In some embodiments, the provided methods involve determining a sequence present in an amplification product, wherein the sequence is indicative of the presence and/or the amount of a target nucleic acid or a sequence thereof. In some aspects, the amplification product is formed using a circular or circularized polynucleotide (e.g., a padlock probe) as a template and a polynucleotide as a primer. In some aspects, the amplification product includes a barcode sequence, which is also amplified during the amplification step. In some aspects, an amplified sequence, such as the amplified barcode sequence present in the polynucleotide (e.g., a padlock probe) can be analyzed and/or detected. In some aspects, the sequence of the barcode is determined. In some aspects, the analysis of the barcode sequence involves sequencing. In some embodiments, a barcode sequence comprises two or more sub-barcode sequences. In some aspects, the barcode sequence comprises a non-contiguous sequence that comprises two or more sub-barcode sequences. In some cases, two or more sub-barcode sequences of a barcode region is determined, e.g., in sequencing-by-click-ligation cycles and/or rounds disclosed herein.

In some embodiments, the analysis and/or determination of sequence of the polynucleotide (e.g., a padlock probe) is performed after circularization or the ligation of the polynucleotide (e.g., a padlock probe), amplification of the polynucleotide (e.g., a padlock probe), and/or contacting the target nucleic acid or a biological sample containing the target nucleic acid with one or more polynucleotide(s) that form a probe set to generate a circular probe. In some aspects, the analysis and/or sequence determination also include one or more of: obtaining images or detection of signal from the detectable probe and/or data analysis.

In some aspects, the analysis of the sequence comprises determining the sequence of all or a portion of the amplification product. In some embodiments, the determining the sequence comprises sequencing all or a portion of the amplification product, such as one or more barcode sequence(s) present in the amplified product. In some embodiments, the sequencing can include sequencing by hybridization, sequencing by ligation, and/or fluorescent in situ sequencing.

In some aspects, the analysis of the sequence comprises in situ hybridization to all or a portion of the amplification product. In some aspects, analyzing the sequence comprises hybridizing to the amplification product a detection oligonucleotide labeled with a fluorophore, an isotope, a mass tag, or a combination thereof. In some embodiments, the detecting comprises in situ hybridization to one or more barcode sequence(s). In some embodiments, the in situ hybridization comprises sequential fluorescent in situ hybridization.

In some embodiments, the analyzing the sequence comprises imaging the amplification product. In some cases, analysis is performed on one or more images captured, and may comprise processing the image(s) and/or quantifying signals observed. In some embodiments, images of signals from different fluorescent channels and/or detectable probe hybridization and ligation cycles can be compared and analyzed. In some embodiments, images of signals (or absence thereof) at a particular location in a sample from different fluorescent channels and/or sequential detectable probe hybridization and ligation cycles can be aligned to analyze an analyte at the location. For instance, a particular location in a sample can be tracked and signal spots from sequential sequencing-by-ligation cycles can be analyzed to detect a target polynucleotide sequence (e.g., a barcode sequence or subsequence thereof) in a nucleic acid at the location. The analysis may comprise processing information of one or more cell types, one or more types of analytes, a number or level of analyte, and/or a number or level of cells detected in a particular region of the sample. In some embodiments, the analysis comprises detecting a sequence e.g., a barcode sequence present in an amplification product at a location in the sample. In some embodiments, the analysis includes quantification of puncta (e.g., if amplification products are detected). In some cases, the analysis includes determining whether particular cells and/or signals are present that correlate with one or more analytes from a particular panel. In some embodiments, the obtained information may be compared to a positive and negative control, or to a threshold of a feature to determine if the sample exhibits a certain feature or phenotype. In some cases, the information may comprise signals from a cell, a region, and/or comprise readouts from multiple detectable labels. In some case, the analysis further includes displaying the information from the analysis or detection step. In some embodiments, software may be used to automate the processing, analysis, and/or display of data.

In some embodiments, the target nucleic acid is an mRNA in a tissue sample, and the analyzing the sequence is performed when the target nucleic acid and/or the amplification product is in situ in the tissue sample.

In some embodiments, the detectable probe comprises an interrogatory region complementary to a sequence of interest (e.g., target sequence) in the target polynucleotide sequence. In some aspect, the sequence of interest in the target polynucleotide sequence comprises a barcode sequence or portion thereof (e.g., a dinucleotide sequence). In some aspects, one or more of the target sequences includes one or more barcode(s), e.g., at least two, three, four, five, six, seven, eight, nine, ten, or more barcodes. Barcodes can spatially-resolve molecular components found in biological samples, for example, within a cell or a tissue sample. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI"). In some aspects, a barcode comprises about 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In some embodiments, a barcode includes two or more sub-barcodes that together function as a single barcode. For example, a polynucleotide barcode can include two or more polynucleotide sequences (e.g., sub-barcodes) that are separated by one or more non-barcode sequences. In some aspects, a sub-barcode comprises about 2, 3, 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In some embodiments, the one or more barcode(s) can also provide a platform for targeting functionalities, such as oligonucleotides, oligonucleotide-antibody conjugates, oligonucleotide-streptavidin conjugates, modified oligonucleotides, affinity purification, detectable moieties, enzymes, enzymes for detection assays or other functionalities, and/or for detection and identification of the polynucleotide.

In some embodiments, barcode sequences can be analyzed using a method described herein in combination with one or more other methods or techniques, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), hybridization-based in situ sequencing (HybISS), targeted in situ sequencing, fluorescent in situ sequencing (FISSEQ), sequencing by synthesis (SBS), sequencing by ligation (SBL) using a ligase, sequencing by hybridization (SBH), or spatially-resolved transcript amplicon readout mapping (STARmap).

In some embodiments, in a barcode sequencing method, barcode sequences are detected for identification of other molecules including nucleic acid molecules (DNA or RNA) longer than the barcode sequences themselves, as opposed to direct sequencing of the longer nucleic acid molecules. In some embodiments, a N-mer barcode sequence comprises $4^N$ complexity given a sequencing read of N bases, and a much shorter sequencing read may be required for molecular identification compared to non-barcode sequencing methods such as direct sequencing. For example, 1024 molecular species may be identified using a 5-nucleotide barcode sequence ($4^5$=1024), whereas 8 nucleotide barcodes can be used to identify up to 65,536 molecular species, a number greater than the total number of distinct genes in the human genome. In some embodiments, the barcode sequences contained in the probes or RCPs are detected, rather than endogenous sequences, which can be an efficient read-out in terms of information per cycle of sequencing. Because the barcode sequences are pre-determined, they can also be designed to feature error detection and correction mechanisms, see, e.g., U.S. Pat. Pub. 20190055594 and WO2019199579A1, which are hereby incorporated by reference in their entirety.

In some embodiments, a label or detectable label can be a directly or indirectly detectable moiety that is associated with (e.g., conjugated to) a molecule to be detected, e.g., a detectable probe, including, but not limited to, fluorophores, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like.

In some embodiments, a fluorophore can include a substance or a portion thereof that is capable of exhibiting fluorescence in the detectable range. Particular examples of labels that may be used in accordance with the provided embodiments include, but are not limited to phycoerythrin, Alexa dyes, fluorescein, YPet, CyPet, Cascade blue, allophycocyanin, Cy3, Cy5, Cy7, rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, Renilla luciferase, NADPH, beta-galactosidase, horseradish peroxidase, glucose oxidase, alkaline phosphatase, chloramphenical acetyl transferase, and urease.

In some embodiments, the one or more target polynucleotides within the barcode region of unknown sequence are contacted with detectable probes (probes connected to cleavable detectable labels, e.g., detectable probes). In some embodiments, the detectable probes are two or more nucleotides in length. In some embodiments, the detectable probes are or are about two nucleotides in length. In some embodiments, the detectable probes are or are about three nucleotides in length. In some embodiments, the detectable probes are or are about four nucleotides in length. In some embodiments, the detectable probes are or are about five nucleotides in length. In some embodiments, the detectable probes are or are about five nucleotides in length. In some embodiments, the detectable probes are or are about six nucleotides in length. In some embodiments, the detectable probes are or are about seven nucleotides in length. In some embodiments, the detectable probes are or are about eight nucleotides in length. In some embodiments, the detectable probes are or are about nine nucleotides in length. In some embodiments, the detectable probes are or are about 10 nucleotides in length. In some embodiments, the detectable probes are or are about 12 nucleotides in length. In some embodiments, the detectable probes are or are about 14 nucleotides in length. In some embodiments, the detectable probes are or are about 16 nucleotides in length. In some embodiments, the detectable probes are or are about 18 nucleotides in length. In some embodiments, the detectable probes are or are about 20 nucleotides in length. In some embodiments, the detectable probes are or are about 22 nucleotides in length. In some embodiments, the detectable probes are or are about 24 nucleotides in length. In some embodiments, the detectable probes are or are about 26 nucleotides in length. In some embodiments, the detectable probes are or are about 28 nucleotides in length. In some embodiments, the detectable probes are or are about 30 nucleotides in length. In some embodiments, the detectable probes are less than 5, less than 10, less than 15, less than 20, less than 25, or less than 30 nucleotides in length. In some embodiments, for example when the target nucleotide comprises one or more barcode sequences, the use of an 8-nt barcode would enable sequencing of the entire transcriptome. In some embodiments, the use of an 8-nt barcode would enable sequencing of 65,536 genes.

The detectable probes described herein each generally include (1) at least one base pair that is known prior to contacting the reading probe, and (2) a label (e.g., a detectable label) that corresponds to the identity (e.g., A, G, C, or T) of the at least one base pair having a known sequence. For example, the when a detectable probe is complementary to the sequence of the barcode the detectable probe will hybridize (e.g., Watson-Crick base pairing) with the barcode and the label (e.g., any of the exemplary labels described herein) will be detectable upon interrogation.

In some embodiments, the detectable probes include a known nucleotide sequence located in at least one location within the detectable probe (e.g., the location with the known nucleotide is the "3' sequence position"). For example, the detectable probe can include a sequence where it is known that an A, G, C, or T is located at the first position in the 3' to 5' orientation sequencing probed. The first position in the 3' to 5' sequence orientation of the detectable probe can be an A. The first position in the 3' to 5' sequence orientation of the detectable probe can be a G. The first position in the 3' to 5' sequence orientation of the detectable probe can be a C. The first position in the 3' to 5' sequence orientation of the detectable probe can be a T. In cases where the first position of the detectable probe includes a known sequence, the remaining nucleotides include a degenerate sequence (e.g., universal bases).

In some embodiments, the detectable probe can include a sequence where it is known that an A, G, C or T is located at the second position in the 3' to 5' orientation of the detectable probe (e.g., the second position is the "3' sequence position"). For example, the second position in the 3' to 5' sequence orientation of the detectable probe can be an A. The second position in the 3' to 5' sequence orientation of the detectable probe can be a G. The second position in the 3' to 5' sequence orientation of the detectable probe can be a C. The second position in the 3' to 5' sequence orientation of the detectable probe can be a T. In cases where, the second position of the detectable probe includes a known sequence, the remaining nucleotides include a degenerate sequence (e.g., universal bases).

In some embodiments, the detectable probe can include a sequence where it is known that an A, G, C, or T is located at the first position in the 5' to 3' orientation of the detectable probe (e.g., the first position is the "5' sequence position"). The first position in the 5' to 3' sequence orientation of the detectable probe can be an A. The first position in the 5' to 3' sequence orientation of the detectable probe can be a G. The first position in the 5' to 3' sequence orientation of the detectable probe can be a C. The first position in the 5' to 3' sequence orientation of the detectable probe can be a T. In cases where the first position of the detectable probe includes a known sequence, the remaining nucleotides include a degenerate sequence (e.g., universal bases).

In some embodiments, the detectable probe can include a sequence where it is known that an A, G, C or T is located at the second position in the 5' to 3' orientation of the detectable probe (e.g., the second position is the "5' sequence position"). For example, the second position in the 5' to 3' sequence orientation of the detectable probe can be an A. The second position in the 5' to 3' sequence orientation of the detectable probe can be a G. The second position in the 5' to 3' sequence orientation of the detectable probe can be a C. The second position in the 5' to 3' sequence orientation of the detectable probe can be a T. In cases where, the second position of the detectable probe includes a known sequence, the remaining nucleotides include a degenerate sequence (e.g., universal bases). In some embodiments, a plurality of detectable probes are of formula $N_xB_yN_z$, wherein N is a degenerate base and B is an interrogatory base, x, y, and z are integers independent of each other, x is 0 or greater, y is 1, and z is 0 or greater.

In some embodiments, where a detectable probe includes a first known nucleotide at a first position (e.g., the first nucleotide at the 3' end or first nucleotide at the 5' end) and a second known nucleotide at a second position (e.g., the second nucleotide from the 3' end or second nucleotide at the 5' end), there are 16 possible dinucleotide combinations. For example, the 16 possible dinucleotide combinations include: TA, CG, GC, TA, AC, AA, GA, CA, CC, TC, GT, GG, AG, TG, TT, and CT.

In some embodiments, a plurality of detectable probes are of formula $N_xB_yN_z$, wherein N is a degenerate base and B is an interrogatory base, x, y, and z are integers independent of each other, x is 0 or greater, y is 2, and z is 0 or greater. In some embodiments, each of the plurality of detectable probes comprises: (i) a click functional group, (ii) interrogatory region $B_y$, and (iii) a detectable label corresponding to one or more different interrogatory regions in the plurality of detectable probes. In some embodiments, the detectable probes are dinucleotides including one or more or all of AA, AT, AC, AG, TA, TT, TC, TG, CA, CT, CC, CG, GA, GT, GC, and GG. For example, as shown in FIGS. 4A-4E, click chemistry bioconjugation of fluorescently labeled dinucleotide probes to reading probe hybridized to adaptor sequences may be used in an in situ sequencing reaction. In some embodiments, after each cycle of detectable probe hybridization, the fluorescently labeled dinucleotide probe can be "unclicked", e.g., for regenerate a click functional group for a subsequent cycle of detectable probe hybridization and ligation using an orthogonal click chemistry. In some embodiments, after each cycle of detectable probe hybridization, the fluorescent label on the dinucleotide probe can be removed before a subsequent cycle of detectable probe hybridization. Sequencing can be repeated with detectable probes comprising orthogonal click groups to detect different barcode sequences without stripping the probes (e.g., reading probes) for each detectable probe hybridization and ligation cycle. After each sequencing round (which may comprise multiple detectable probe hybridization and ligation cycles), the probes can be unhybridized and new reading probes with base shift (e.g., −1, +1, or +2) can be hybridized all at one for a subsequent sequencing round. Multiple detectable probe hybridization and ligation cycles can be performed in the subsequent sequencing round, for instance, essentially as described in FIGS. 3A-3B or FIGS. 4A-4E. A combination of ligase-catalyzed reaction and click chemistry reaction may be used in the same sequencing round (e.g., enzymatic ligation in one detectable probe hybridization and ligation cycle and click chemistry ligation in another cycle) and/or in different sequencing rounds (e.g., multiple detectable probe hybridization and ligation cycles using enzymatic ligation in one sequencing round and multiple detectable probe hybridization and ligation cycles using click chemistry ligation in another sequencing round).

In some embodiments, the detectable probe can include a sequence where it is known that an A, G, C, or T is present at any of the positions in a 3' to 5' orientation (e.g., any of the positions with the known nucleotide is the "3' sequence position"). In some embodiments, the detectable probe can include a sequence where it is known that an A, G, C, or T is present at any of the positions in a 5' to 3' orientation.

In some embodiments, the nucleotides included in a detectable probe and/or an anchor can be non-natural nucleotides, modified nucleotides (e.g., 5' Methyl group, 2' Fluoro) or any of a variety of different nucleotides that can facilitate the sequencing methods described above. Additional examples of such nucleotides have been described previously.

In some embodiments, the detectable probes have sequences with formula $N_xB_yN_z$, wherein N is an unknown degenerate base; B is a known interrogatory base; and x, y, and z are integers independent of each other, wherein x and/or z equal zero or greater and y equals one or greater. In some embodiments, x and/or z equals 0. In some embodiments, x and/or z equals 1. In some embodiments, x and/or z equals 2. In some embodiments, x and/or z equals 4. In some embodiments, x and/or z equals 6. In some embodiments, x and/or z equals 8. In some embodiments, x and/or z equals 10. In some embodiments, x and/or z equals 12. In some embodiments, x and/or z equals 14. In some embodiments, x and/or z equals 16. In some embodiments, x and/or z equals 18. In some embodiments, x and/or z equals 20. In some embodiments, y equals 1. In some embodiments, y equals 2. In some embodiments, y equals 3. In some embodiments, y equals 4. In some embodiments, y equals 5. In some embodiments, y equals 6. In some embodiments, y equals 7. In some embodiments, y equals 8. In some embodiments, y equals 9. In some embodiments, y equals 10. In some embodiments, y equals 12. In some embodiments, y equals 14. In some embodiments, y equals 16. In some embodiments, y equals 18. In some embodiments, y equals 20. The barcode region of unknown sequence may be contacted with detectable probes, wherein each detectable probe comprises a known interrogatory base B, and unknown degenerates bases N. In some embodiments, the interrogatory base corresponds to the detection signal of the probe upon hybridization with the barcode region (e.g., the color of the fluorescent detectable probe). In some embodiments, the detectable probe includes universal bases. As used herein, a "universal base" refers to a nucleobase analog that can hybridize non-selectively to each of the native bases (e.g., A, C, G, or T). (See Berger et al., *Nucleic Acid Res.*, 28(15): 2911-2914 (2000), the entire contents of which are incorporated herein by reference.

A detectable probe that includes a sequence of 3'-ANNNNNNN-5', where A is a known nucleotide at a first position (e.g., the 3' sequence position) and N represents a universal base or degenerate base located at positions two through eight, will hybridize to a complement sequence only when a T is at the first position on the 5' end (e.g., 5'-TNNNNNNN-3'. The non-selective nature of the universal bases allows ligation where there is complementarity between the known one or more nucleotides and the complementary strand (e.g., barcode sequence). In some embodiments, where there are there are two known nucleotides in the sequence, ligation occurs between the detectable probe and the complementary sequence when there is complementarity between the two known nucleotides and the two corresponding nucleotides in the complementary sequence. In some embodiments, all of the N bases are universal bases. In some embodiments, all of the N bases are degenerate bases. In some embodiments, the N bases can be a mix of one or more degenerate nucleotides and one or more universal nucleotides. The number of N bases included in a detectable probe can vary, e.g., from one to 10 nucleotides, 2 to 8 nucleotides, 2 to 6 nucleotides, or 2 to 4 nucleotides.

In some embodiments, each of the detectable probes are connected to a click functional group. In some embodiments, each of the detectable probes are connected to the same click functional group. In some embodiments, some of the detectable probes are connected to different click functional groups. In some embodiments, each of the detectable probes are connected to different click functional groups. Various click functional groups are described in Section III.E ("Click Chemistry Bioconjugation"). In some embodiments, the detectable probe click functional groups are complementary (e.g., react selectively with) the click functional groups of particular click functional groups connected to the primer (e.g., the reading probe).

D. Detectable Labels

In some aspects, a detectable probe further comprises a detectable label. Methods for binding and identifying a target nucleic acid that uses various probes or oligonucleotides have been described in, e.g., US2003/0013091, US2007/0166708, US2010/0015607, US2010/0261026, US2010/0262374, US2010/0112710, US2010/0047924, and US2014/0371088, each of which is incorporated herein by reference in its entirety. Detectably-labeled probes can be useful for detecting multiple target nucleic acids and be detected in one or more hybridization cycles (e.g., sequential hybridization in a FISH-type assay, sequencing by hybridization).

In some aspects, the provided methods comprise imaging the detectable probe, for example, via ligating of a detectable probe comprising a detectable label and detecting the detectable label. In some embodiments, the detectable probe comprises a detectable label that can be measured and quantitated. The terms "label" and "detectable label" comprise a directly or indirectly detectable moiety that is associated with (e.g., conjugated to) a molecule to be detected, e.g., a detectable probe, comprising, but not limited to, fluorophores, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like.

In some embodiments, each detectable probe is connected to a detectable label. In some embodiments, the detectable label is a fluorophore. The term "fluorophore" comprises a substance or a portion thereof that is capable of exhibiting fluorescence in the detectable range. Particular examples of labels that may be used in accordance with the provided embodiments comprise, but are not limited to phycoerythrin, Alexa dyes, fluorescein, YPet, CyPet, Cascade blue, allophycocyanin, Cy3, Cy5, Cy7, rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, *Renilla* luciferase, NADPH, beta-galactosidase, horseradish peroxidase, glucose oxidase, alkaline phosphatase, chloramphenical acetyl transferase, and urease.

Fluorescence detection in tissue samples can often be hindered by the presence of strong background fluorescence. "Autofluorescence" is the general term used to distinguish background fluorescence (that can arise from a variety of sources, including aldehyde fixation, extracellular matrix components, red blood cells, lipofuscin, and the like) from the desired immunofluorescence from the fluorescently labeled antibodies or probes. Tissue autofluorescence can lead to difficulties in distinguishing the signals due to fluorescent antibodies or probes from the general background. In some embodiments, a method disclosed herein utilizes one or more agents to reduce tissue autofluorescence, for example, Autofluorescence Eliminator (Sigma/EMD Millipore), TrueBlack Lipofuscin Autofluorescence Quencher (Biotium), MaxBlock Autofluorescence Reducing Reagent Kit (MaxVision Biosciences), and/or a very intense black dye (e.g., Sudan Black, or comparable dark chromophore).

Examples of detectable labels comprise but are not limited to various radioactive moieties, enzymes, prosthetic groups, fluorescent markers, luminescent markers, bioluminescent markers, metal particles, protein-protein binding pairs and protein-antibody binding pairs. Examples of fluorescent proteins comprise, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride and phycoerythrin.

Examples of bioluminescent markers comprise, but are not limited to, luciferase (e.g., bacterial, firefly and click beetle), luciferin, aequorin and the like. Examples of enzyme systems having visually detectable signals comprise, but are not limited to, galactosidases, glucorimidases, phosphatases, peroxidases and cholinesterases. Identifiable markers also comprise radioactive compounds such as $^{125}$I, $^{35}$S, $^{14}$C, or $^{3}$H. Identifiable markers are commercially available from a variety of sources.

Examples of fluorescent labels and nucleotides and/or polynucleotides conjugated to such fluorescent labels comprise those described in, for example, Hoagland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991). In some embodiments, exemplary techniques and methods methodologies applicable to the provided embodiments comprise those described in, for example, U.S. Pat. Nos. 4,757,141, 5,151,507 and 5,091,519. In some embodiments, one or more fluorescent dyes are used as labels for labeled target sequences, for example, as described in U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthine dyes); and U.S. Pat. No. 5,688,648 (energy transfer dyes). Labelling can also be carried out with quantum dots, as described in U.S. Pat. Nos. 6,322,901, 6,576,291, 6,423,551, 6,251,303, 6,319,426, 6,426,513, 6,444,143, 5,990,479, 6,207,392, US 2002/0045045 and US 2003/0017264. As used herein, the term "fluorescent label" comprises a signaling moiety that conveys information through the fluorescent absorption and/or emission properties of one or more molecules. Exemplary fluorescent properties comprise fluorescence intensity, fluorescence lifetime, emission spectrum characteristics and energy transfer.

Examples of commercially available fluorescent nucleotide analogues readily incorporated into nucleotide and/or polynucleotide sequences comprise, but are not limited to, Cy3-dCTP, Cy3-dUTP, Cy5-dCTP, Cy5-dUTP (Amersham Biosciences, Piscataway, N.J.), fluorescein-!2-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHOD AMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHOD AMINE GREEN™-5-UTP, ALEXA FLUOR™ 488-5-UTP, and ALEXA FLUOR™ 546-14-UTP (Molecular Probes, Inc. Eugene, Oreg.). Methods are known for custom synthesis of nucleotides having other fluorophores (See, Henegariu et al. (2000) Nature Biotechnol. 18:345).

Other fluorophores available for post-synthetic attachment comprise, but are not limited to, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, Texas Red (available from Molecular Probes, Inc., Eugene, Oreg.), Cy2, Cy3.5, Cy5.5, and Cy7 (Amersham Biosciences, Piscataway, N.J.). FRET tandem fluorophores may also be used, comprising, but not limited to, PerCP-Cy5.5, PE-Cy5, PE-Cy5.5, PE-Cy7, PE-Texas Red, APC-Cy7, PE-Alexa dyes (610, 647, 680), and APC-Alexa dyes.

In some cases, metallic silver or gold particles may be used to enhance signal from fluorescently labeled nucleotide and/or polynucleotide sequences (Lakowicz et al. (2003) Bio Techniques 34:62).

Biotin, or a derivative thereof, may also be used as a label on a nucleotide and/or a polynucleotide sequence, and subsequently bound by a detectably labeled avidin/streptavidin derivative (e.g., phycoerythrin-conjugated streptavidin), or a detectably labeled anti-biotin antibody. Digoxigenin may be incorporated as a label and subsequently bound by a detectably labeled anti-digoxigenin antibody (e.g., fluoresceinated anti-digoxigenin). An aminoallyl-dUTP residue may be incorporated into a polynucleotide sequence and subsequently coupled to an N-hydroxy succinimide (NHS) derivatized fluorescent dye. In general, any member of a conjugate pair may be incorporated into a detection polynucleotide provided that a detectably labeled conjugate partner can be bound to permit detection. As used herein, the term antibody refers to an antibody molecule of any class, or any sub-fragment thereof, such as an Fab.

Other suitable labels for a polynucleotide sequence may comprise fluorescein (FAM), digoxigenin, dinitrophenol (DNP), dansyl, biotin, bromodeoxyuridine (BrdU), hexahistidine (6×His), and phosphor-amino acids (e.g., P-tyr, P-ser, P-thr). In some embodiments the following hapten/antibody pairs are used for detection, in which each of the antibodies is derivatized with a detectable label: biotin/a-biotin, digoxigenin/a-digoxigenin, dinitrophenol (DNP)/a-DNP, 5-Carboxyfluorescein (FAM)/a-FAM.

In some embodiments, the detectable label is on the 5' end of the detectable probes. In some embodiments, detectable labels differ across detectable probes. In some embodiments, the detectable label is indicative of subsequence B of its detectable probe. In some embodiments, the detectable label (e.g., fluorophore) is installed via amine-reactive crosslinker chemistry. In some embodiments, the detectable label is installed via N-Hydroxysuccinimide (NHS) chemistry.

In some embodiments, detectable labels are connected to detectable probes via a cleavable linker to form the detectable probes. In some embodiments, the cleavable linker comprises a photocleavable linker. Photocleavable linkers are known in the art (see, e.g., Seo et al. (2005), PNAS 102(17): 5926-5931, incorporated by reference herein in its entirety). In some embodiments, the photocleavable linker comprises a nitrobenzyl group. For instance, a photocleavable nitrobenzyl linker can be cleaved using laser irradiation (355 nm, 10 seconds, 1.5 $Wcm^{-2}$).

In some embodiments, the cleavable linker comprises a Pd-cleavable linker. Pd-cleavable linkers are known in the art (see, e.g., Ju et al. (2006), PNAS 103(52): 19635-19640, incorporated by reference herein in its entirety). In some embodiments, the Pd-cleavable linker comprises an allyl group. For instance, a Pd-cleavable allyl linker can be cleaved using incubation with a $Na_2PdCl_4/P(PhSO_3Na)_3$ mixture (30 seconds at 70° C.).

In some embodiments, the cleavable linker comprises a phosphine-cleavable linker. Phosphine-cleavable linkers are known in the art (see, e.g., Guo et al. (2008), PNAS 105(27): 9145-9150, incorporated by reference herein in its entirety). In some embodiments, the phosphine-cleavable linker comprises an azide group. For instance, a phosphine-cleavable azide linker can be cleaved using incubation with a Tris(2-carboxyethyl) phosphine (TCEP) mixture (15 minutes at 65° C.).

In some embodiments, the cleavable linker comprises a disulfide bond. For instance, the disulfide can be cleaved using incubation with a reducing agent, such as beta-mercaptoethanol, TCEP, or dithiothreitol (DTT).

In some embodiments, the sequencing procedure includes a removing step where the detectable probe is cleaved. Cleavage can result in the release of the portion of the detectable probe that does not contain complementarity with the barcode (e.g., the sequence of the detectable probe that includes universal bases). In some embodiments, complementarity between the detectable probe and the barcode occur either at the first one or two nucleotides at the 3' end of the detectable probe or at the first one or two nucleotides at the 5' end of the sequencing probe. For example, when the sequence of interest is downstream (3') of the constant sequence on the barcode and an anchor is hybridized to the constant sequence, the reading probe can provide a click functional group as a substrate for a ligation reaction and the detectable probes can provide a corresponding click functional group. In such circumstances, the detectable probe will include nucleotides with known sequences at the 3' end of the sequencing probe.

In some embodiments, when a detectable probe contains one or two nucleotides at the 3' end that are complementary to the first region of interest, the detectable probe can be bioconjugated to the 5' end of the reading probe. In this circumstance, cleavage of the detectable probe will result in the release (e.g., removal) of the nucleotides at the 5' positions of the sequencing probe. The cleaved detectable probe can now serve as a substrate in a new ligation reaction, if following the cleavage step, the detectable probe retains a free 5' phosphate.

E. Click Chemistry Bioconjugation

Figure 2A:
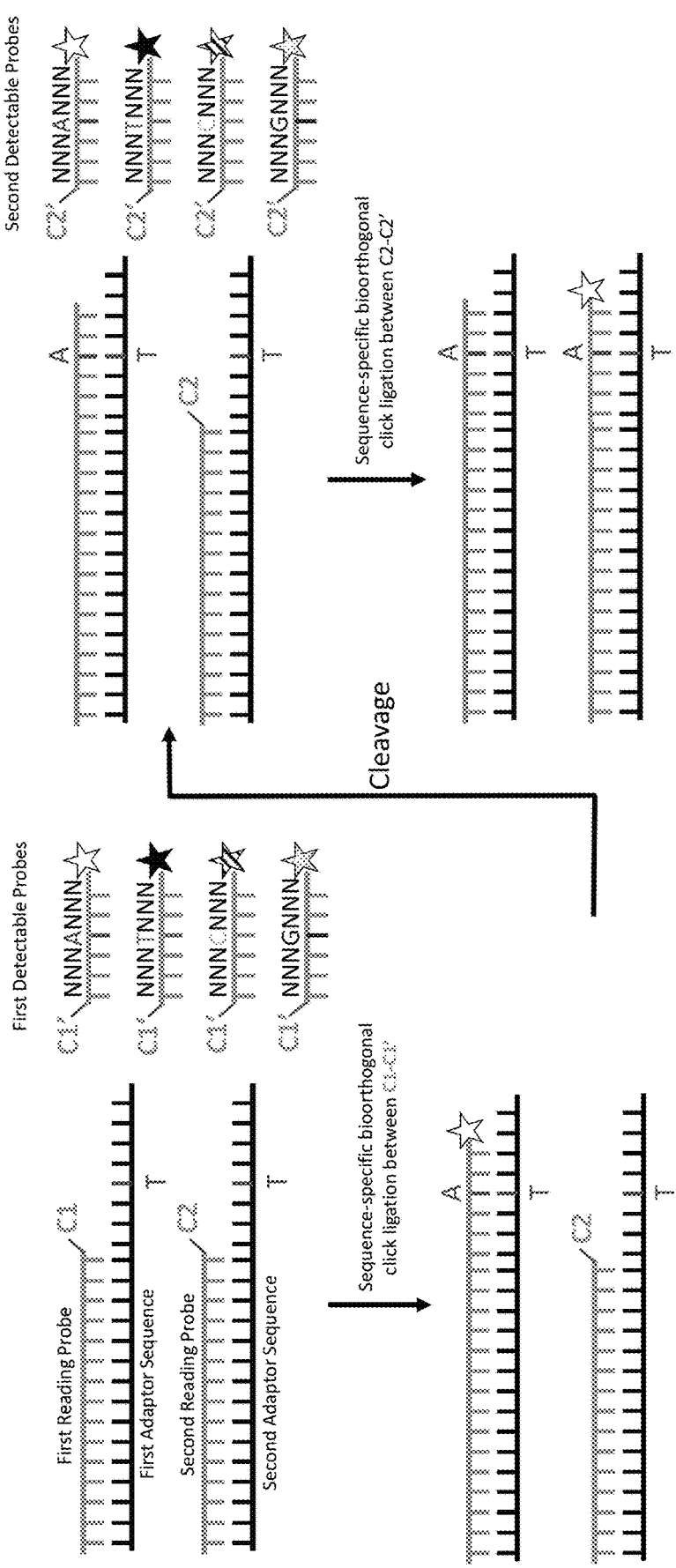
FIG. 2A shows sequencing of two unknown polynucleotide sequences (such as barcode sequences) via the bioconjugation of fluorescently labeled detectable probes to probes (e.g., reading probes) hybridized to adaptor sequences (e.g., known constant regions) of the polynucleotides. The adaptor sequences of the two polynucleotides can be the same or different. Bioconjugation of the detectable probes occurs via separate, orthogonal click reactions using different click functional groups.

In some embodiments, identifying the nucleic acid sequences of the one or more target polynucleotides comprises contacting (1) the adjacent adaptor regions with reading probes each connected to a reading probe click functional group with (2) the one or more target polynucleotides with probes each connected to a detectable probe click functional group. In some embodiments, the reading probe click functional group is on the 5' end of the reading probe. In some embodiments, the detectable probe click functional group is on the 3' end of the reading probe. In some embodiments, the reading probe click functional group is on the 5' end of the reading probe. In some embodiments, the detectable probe click functional group is on the 3' end of the detectable probe. As shown in FIG. 2A, the detectable probe click functional group C1' may react with the reading probe click functional group C1 but does not react with the reading probe click functional group C2 under the same or similar conditions.

In some embodiments, detectable probe click functional group and the reading probe click functional group are a 3'-azido and a 5'-alkynyl, respectively. In some embodiments, the detectable probe click functional group and the reading probe click functional group are a 3'-alkynyl and a 5'-azido, respectively. In some embodiments, the detectable probe click functional group and the reading probe click functional group are a 3'-azido and a 5'-cyclooctynyl, respectively. In some embodiments, the detectable probe click functional group and the reading probe click functional group are a 3'-cyclooctynyl and a 5'-azido, respectively. In some embodiments, the detectable probe click functional group and the reading probe click functional group are a 3'-tetrazine and a 5'-dienophile, respectively. In some embodiments, the detectable probe click functional group and the reading probe click functional group are a 3'-dienophile and a 5'-tetrazine, respectively. In some embodiments, the detectable probe click functional group and the reading probe click functional group are a 3'-thiol and a 5'-alkynyl, respectively. In some embodiments, the detectable probe click functional group and the reading probe click functional group are a 3'-alkynyl and a 5'-thiol, respectively. In some embodiments, the detectable probe click functional group and the reading probe click functional group are a 3'-cyano and a 5'-1,2-amino thiol, respectively. In some embodiments, the detectable probe click functional group and the reading probe click functional group are a 3'-1,2-amino thiol and a 5'-cyano, respectively. In some embodiments, the detectable probe click functional group and the reading probe click functional group are a 3'-nitrone and a 5'-cyclooctynyl, respectively. In some embodiments, the detectable probe click functional group and the reading probe click functional group are a 3'-cyclooctynyl and a 5'-nitrone, respectively.

In some embodiments, the reading probes and detectable probes are bioconjugated via their click functional groups using an enzyme-free click reaction (that is, without use of a polymerase or a ligase for conjugation). In some embodiments, the click reaction is biorthogonal. Any suitable click chemistry is contemplated for use with the compositions, systems, and methods described herein, for example see, e.g., Gartner and Liu (2001), Journal of the American Chemical Society 123(28): 6961-6963; Seckute et al. (2013), Nucleic Acids Research 41(15): e148; and Patterson et al. (2014), ACS Chem. Biol. 9(3): 592-605, all of which are incorporated by reference herein in their entirety. In some instances the click functional groups described herein comprise at one μM concentration per click functional group, a click reaction with a $k_2$ rate ($M^6s^{-1}$) and associated half-life of $10^5$ and 10 seconds, $10^4$ and 1.7 minutes, $10^3$ and 17 minutes, $10^2$ and 2.8 hours, 10 and 1.2 days, 1 and 12 days, $10^{-1}$ and four months, or $10^{-2}$ and three years.

In some embodiments, the click reaction is a template-independent reaction. Template-independent click reactions are known (see, e.g., Xiong and Seela (2011), J. Org. Chem. 76(14): 5584-5597, incorporated by reference herein in its entirety). In some embodiments, the click reaction is a nucleophilic addition reaction. In some embodiments, the click reaction is a cyclopropane-tetrazine reaction. In some embodiments, the click reaction is a strain-promoted azide-alkyne cycloaddition (SPAAC) reaction. In some embodiments, the click reaction is an alkyne hydrothiolation reaction. In some embodiments, the click reaction is an alkene hydrothiolation reaction. In some embodiments, the click reaction is a strain-promoted alkyne-nitrone cycloaddition (SPANC) reaction. In some embodiments, the click reaction is an inverse electron-demand Diels-Alder (IED-DA) reaction. In some embodiments, the click reaction is a cyanobenzothiazole condensation reaction. In some embodiments, the click reaction is an aldehyde/ketone condensation reaction. In some embodiments, the click reaction is a Cu(I)-catalyzed azide-alkyne cycloaddition (CuAAC) reaction.

In some embodiments, the click reaction is a template-dependent reaction or template-directed reaction. In some embodiments, the template-dependent reaction is sensitive to base pair mismatches such that reaction rate is significantly higher for matched vs. unmatched templates. In some embodiments, the click reaction is a nucleophilic addition template-dependent reaction. In some embodiments, the click reaction is a cyclopropane-tetrazine template-dependent reaction.

In some embodiments, the sample is washed after the click reaction in order to remove unhybridized and/or unconjugated detectable probes, after which the sample is imaged to detect the conjugated detectable label. In some embodiments, the detectable label is cleaved after imaging.

In some embodiments, reading probes and detectable probes (e.g., multiple reading probe and detectable probe pairs) are bioconjugated using the same click reaction. In some embodiments, reading probes and detectable probes are bioconjugated using the same click reaction, and the adaptor regions have different nucleic acids. In some embodiments, click functional groups differ across reading probes and detectable probes such that different click reactions are necessary to conjugate all reading probes and detectable probes. In some embodiments, the different click reactions are mutually orthogonal such that subsets of reading probes and detectable probes are selectively bioconjugated.

For example, in some embodiments of multiplexing click chemistry bioconjugation, the reading probe click functional group C1 reacts with a specific detectable probe click functional group C1', and additional reading probe click functional groups, such as C2, C3, and C4, etc. react with other specific detectable probe click functional groups, such as CT, C3', and C4' etc., which are complementary with the particular click function groups of the reading probe. In some embodiments, template specificity is achieved through the use of multiple types of click chemistry reactions such that bonds are differentially catalyzed. For example, the click chemistry reaction of C1 with C1' is differentially catalyzed compared with the click chemistry reaction of C2 with C2'. In some embodiments, the multiple types of click chemistry reactions allows for the bioconjugation to be multiplexed and selective to particular complementary probe sets. In some embodiments, the multiple detectable probes (e.g., probes comprising detectable labels and click functional groups Cn') are be hybridized to the barcode regions sequentially. In some embodiments, the multiple detectable probes (e.g., probes comprising detectable labels and click functional groups Cn') are be hybridized to the barcode regions simultaneously or in large pools. In this manner, the provided methods do not increase hybridization time, typically one of the longest step in in situ technologies.

In some embodiments, a first set of detectable probes is provided and a first type of click reaction is performed, after which the sample is washed, imaged, and treated to remove, quench, or cleave the detectable label. In some embodiments, a second set of detectable probes is then provided in order to perform a second type of click reaction, after which the sample is again washed, imaged, and treated to remove, quench, or cleave the detectable label. In some embodiments, this process is repeated using additional detectable probes and types of click reactions. In some aspects, reading probes used for multiple click reactions are hybridized in one step and remains hybridized through two or more types of click reactions. In some aspects, between the first and second type of click reaction, an additional round of hybridizing reading probes is not performed. In some embodiments, two hours of acquisition is needed for the sequencing of 1000 genes. In some embodiments, and to further contribute to providing template specificity, the sample is imaged multiple times, and the average readout of the distribution of images is used.

F. In Situ Sequencing

In some embodiments, provided herein are methods including an in situ sequencing reaction. In some embodiments of any of the methods for decoding a barcode described herein, the method includes an in situ sequencing reaction. In some embodiments, the reaction includes contacting the sample with a plurality of reading probes that hybridize to a plurality of adaptor regions. In some examples, the reaction includes contacting the sample with a plurality of detectable probes, wherein each detectable probe comprises an interrogatory region and a detectable label (e.g., a cleavable detectable label), and is configured to hybridize to the nucleic acid adjacent to an end of the reading probe; bioconjugating a detectable probe complementary to the barcode region to the end of the reading probe (e.g., primer) using click chemistry to generate a ligation product; and detecting a signal associated with the detectable label of the ligation product.

Figure 6:
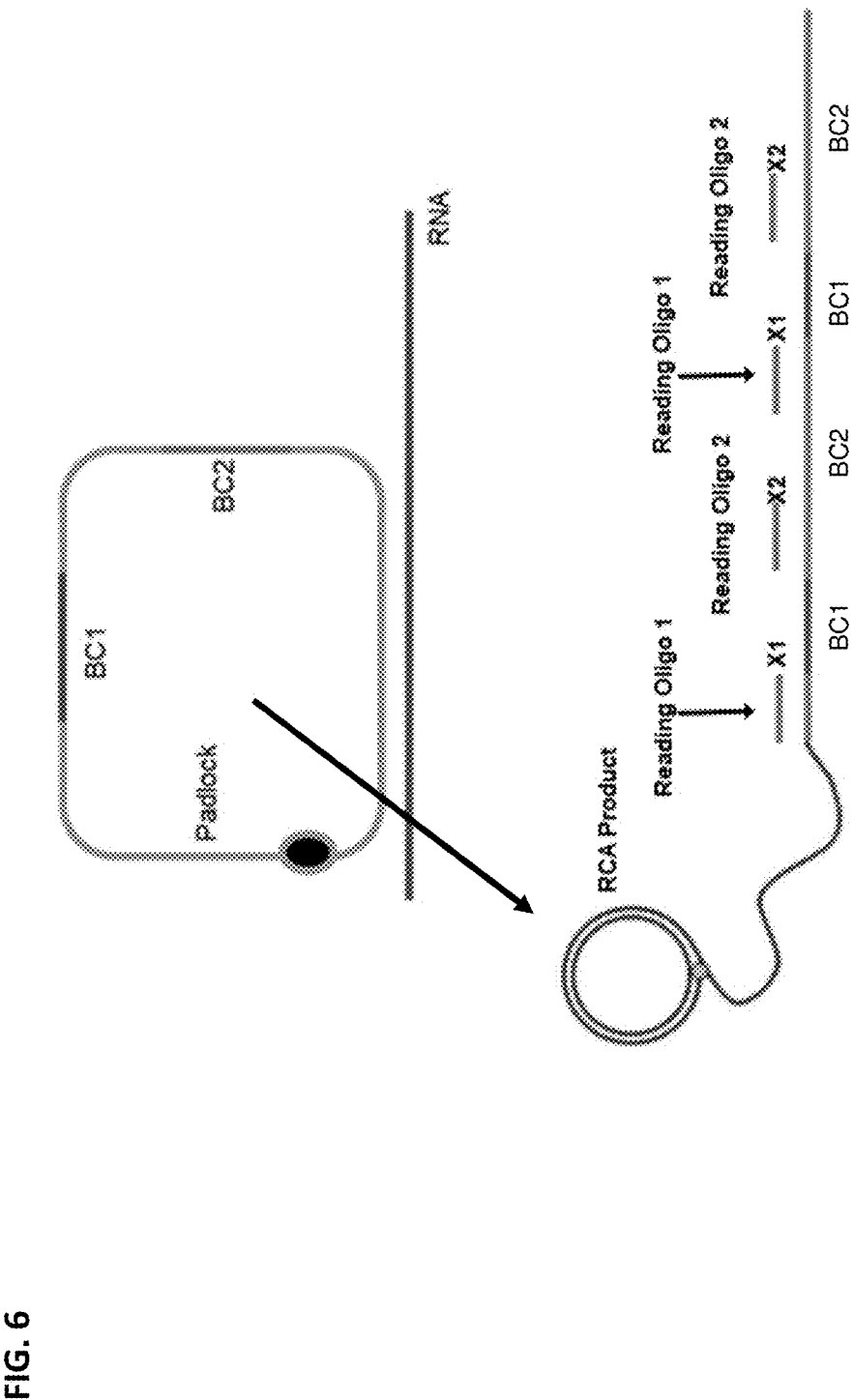
FIG. 6 shows an example of sequencing barcode sequences. An RCA product is generated from a padlock probe hybridized to an RNA target and comprising barcode sequences BC1 and BC2. The padlock may comprise additional barcode sequences that are not shown. The RCA product contains multiple copies of sequences that are complementary to the barcode sequences on the padlock. Reading probes (e.g., Reading Oligo 1 and Reading Oligo 2) may be hybridized to the RCA product all at once, and for each sequence to be analyzed (e.g., complementary sequences to BC1 and BC2 shown in the figure), the reading probes comprise a click functional group X1 or X2 capable of different click reactions.

In some embodiments, an RCA product is generated from a padlock probe hybridized to an RNA target and comprises barcode sequences BC1 and BC2 (FIG. 6). In some embodiments, an RCA product is generated from a padlock probe hybridized to an RNA target and comprises sub-barcode sequences that together forms a barcode associated with the target. The padlock may comprise additional barcode sequences. The RCA product contains multiple copies of sequences that are complementary to the barcode sequences on the padlock. Reading probes (e.g., Reading Oligo 1 and Reading Oligo 2) may be hybridized to the RCA product all at once, and for each sequence to be analyzed (e.g., complementary sequences to BC1 and BC2), the reading probes comprise a click functional group X1 or X2 capable of different click reactions (FIG. 6).

The in situ sequencing protocols are similar in nature to sequencing-by-ligation protocols and other sequencing methods, which have been described, for example, in U.S. Pat. Nos. 5,599,675, 5,750,341, 6,172,218, 6,306,597, 6,969,488, 7,906,285, and 9,404,155; WO2020/056381; and Shendure et al. *Science* (2005), 309: 1728-1732, the contents of which are herein incorporated by reference in their entirety. In some embodiments, sequencing can be performed using single molecule sequencing by ligation. Such techniques utilize a ligase such as DNA ligase or RNA ligase to incorporate oligonucleotides and identify the incorporation of such oligonucleotides. The oligonucleotides typically have different labels that are correlated with the identity of a particular nucleotide in a sequence to which the oligonucleotides hybridize.

In traditional sequencing-by-ligation (SBL), for example, three mismatched interrogating (or "sequencing", e.g., detection) probes and one correctly matched interrogating probe (e.g., detectable probe) compete for the same ligation site. The difference in their Tm is generally ~1-2° C., enabling them to equilibrate freely depending on the reaction temperature. The three mismatched interrogating probes and one correctly matched interrogating probe can have different Tm temperatures based on the presence or absence of a matching nucleotide. The level of detectable probe hybridization is a function of probe Tm, which is a function of their length; while the slight difference in the probe melting temperature can be used to discriminate alleles (i.e., allele-specific PCR, allele-specific FISH), the fraction of correctly hybridized probes vary dramatically even with small changes in the reaction temperature. However, in some examples the slight difference in the hybridization rate is insufficient to discriminate individual bases with high specificity. Without being bound by theory, the use of click chemistry can increase the specificity of the method because the reaction only occurs if the click functional groups are compatible between the reading probe and the detectable probe. This dramatically improves the specificity of allele discrimination. Numerous variations of sequencing-by-ligation using click chemistry are possible and are used in a method disclosed herein.

Sequencing by ligation can proceed in either direction (either 5'-3' or 3'-5') depending on which end of the detectable probes are blocked by the label. In some embodiments, the 3'-5' direction (which is the opposite direction to polymerase based sequencing methods) is more efficient for doing multiple cycles of ligation.

Figure 2B:
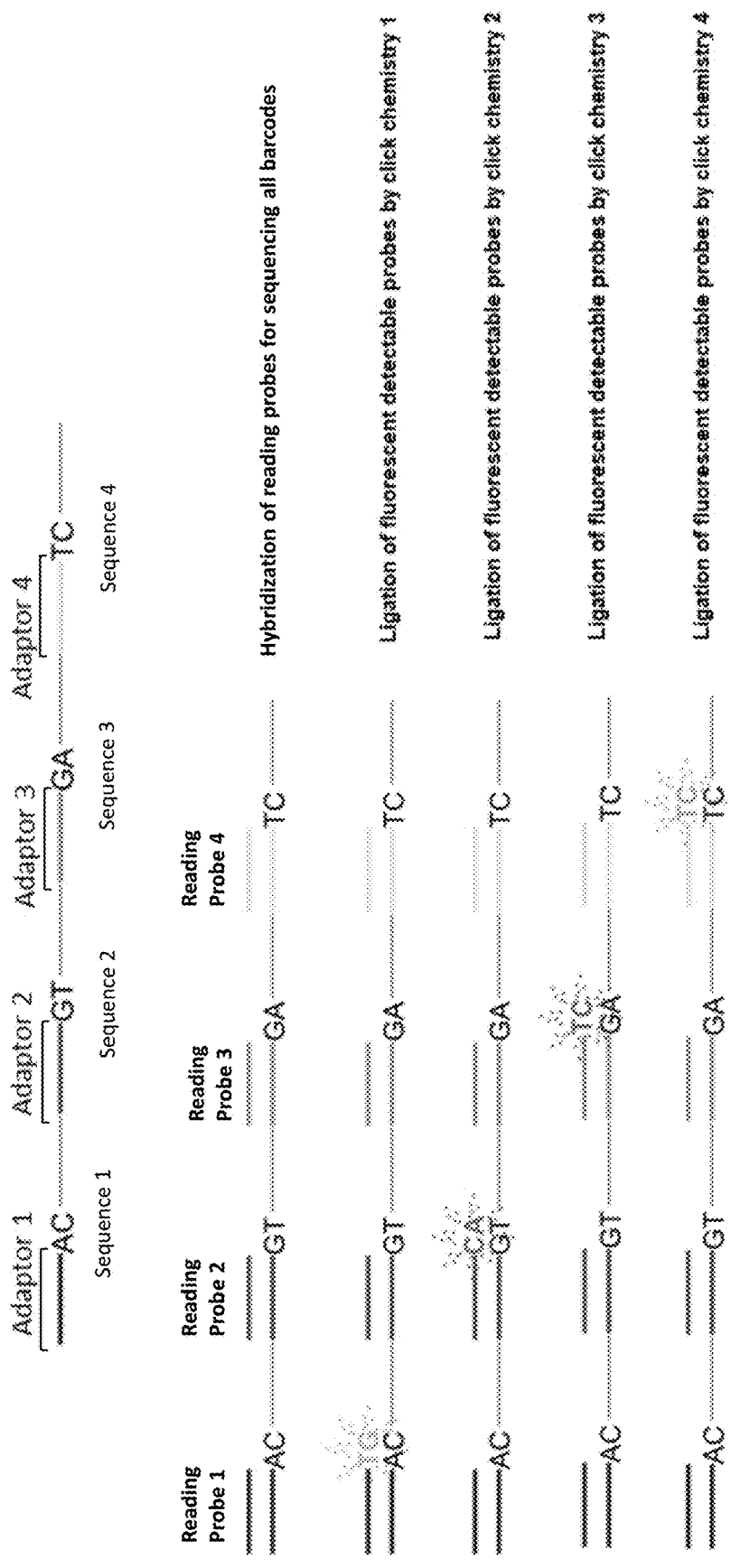
FIG. 2B shows sequencing of four sequences (e.g., barcode or sub-barcode sequences) within one or more target molecules. Although the four sequences and four adaptor sequences are shown as a linear sequence, each adaptor sequence/sequence pair can be on the same molecule (linear or circular) or on different molecules (linear or circular), and when any two or more of the pairs are on the same molecule, they can be immediately adjacent to one another or spaced apart. Sequencing occurs via the bioconjugation of fluorescently labeled probes (e.g., that interrogate dinucleotides) in separate, orthogonal click reactions using different click functional groups. In some examples, each of the four reading probes comprises a click functional group capable of different click reactions, e.g., click reactions that are orthogonal to each other.
Figure 3A:
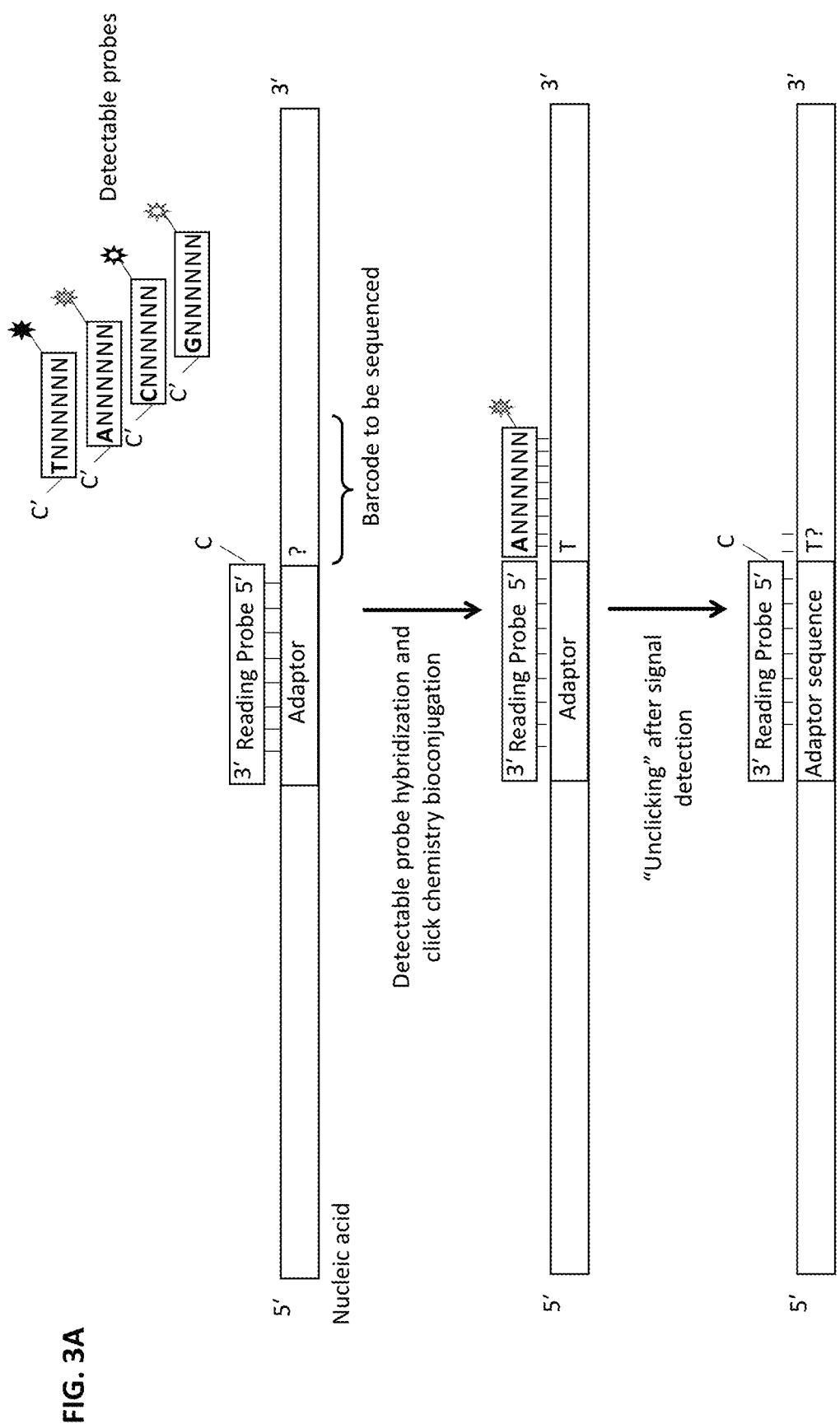
FIGS. 3A-3B show an exemplary in situ sequencing reaction using click chemistry bioconjugation, wherein the position of the interrogatory nucleotide or sequence (e.g., a single interrogatory nucleotide as shown) is shifted in each cycle of detectable probe hybridization, thereby determining a sequence of the unknown barcode region. After each cycle of detectable probe hybridization, the bioconjugated detectable probe can be "unclicked" from the probe while leaving the probe (e.g., reading probe) hybridized to the nucleic acid in the sample.
Figure 3B:
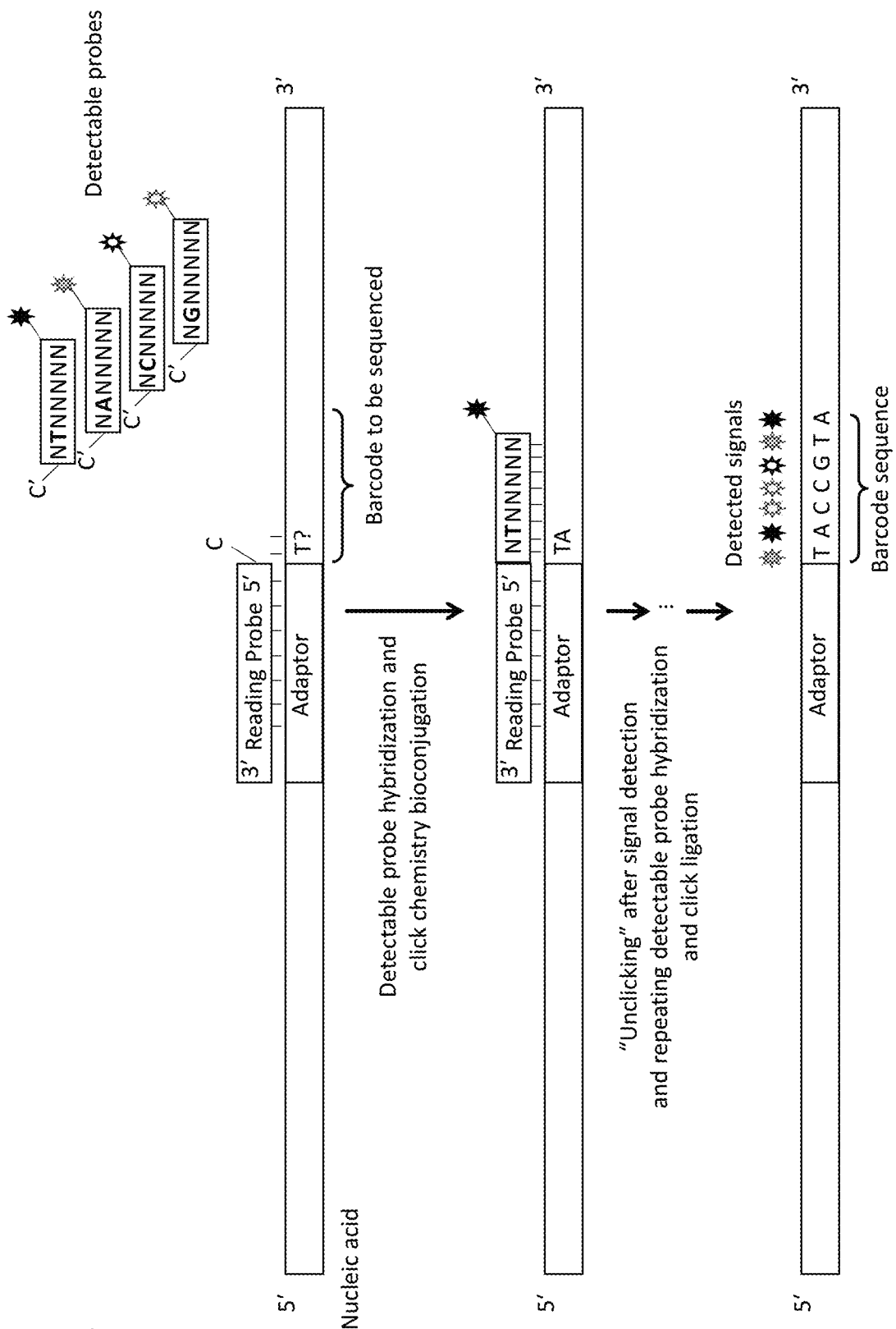
Figure 4A:
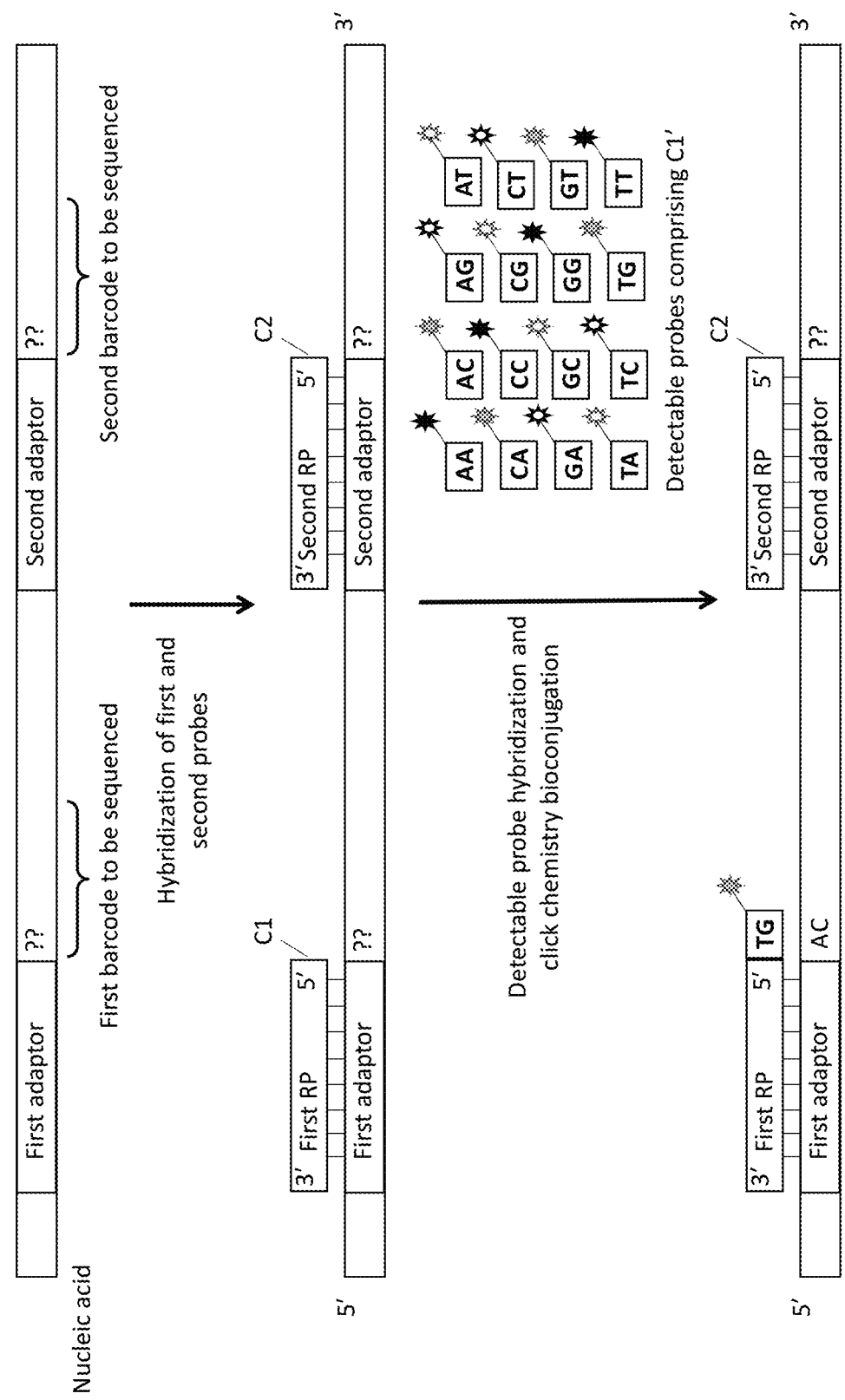
FIGS. 4A-4E show an exemplary in situ sequencing reaction using click chemistry bioconjugation of fluorescently labeled dinucleotide probes (detectable probes) to probes (e.g., reading probe, "RP") hybridized to adaptor sequences. After each cycle of detectable probe hybridization, the fluorescently labeled dinucleotide probe can be "unclicked", or the fluorescent label can be removed, before a subsequent cycle of detectable probe hybridization and ligation using an orthogonal click chemistry. Sequencing can be repeated with detectable probes comprising orthogonal click groups to detect different barcode sequences without stripping the probes (e.g., reading probes) for each detectable probe hybridization and ligation cycle. After each sequencing round (which may comprise multiple detectable probe hybridization and ligation cycles), the reading probes can be unhybridized and new reading probes with base shift (e.g., −1, +1, or +2) can be hybridized all at one for a subsequent sequencing round.
Figure 4B:
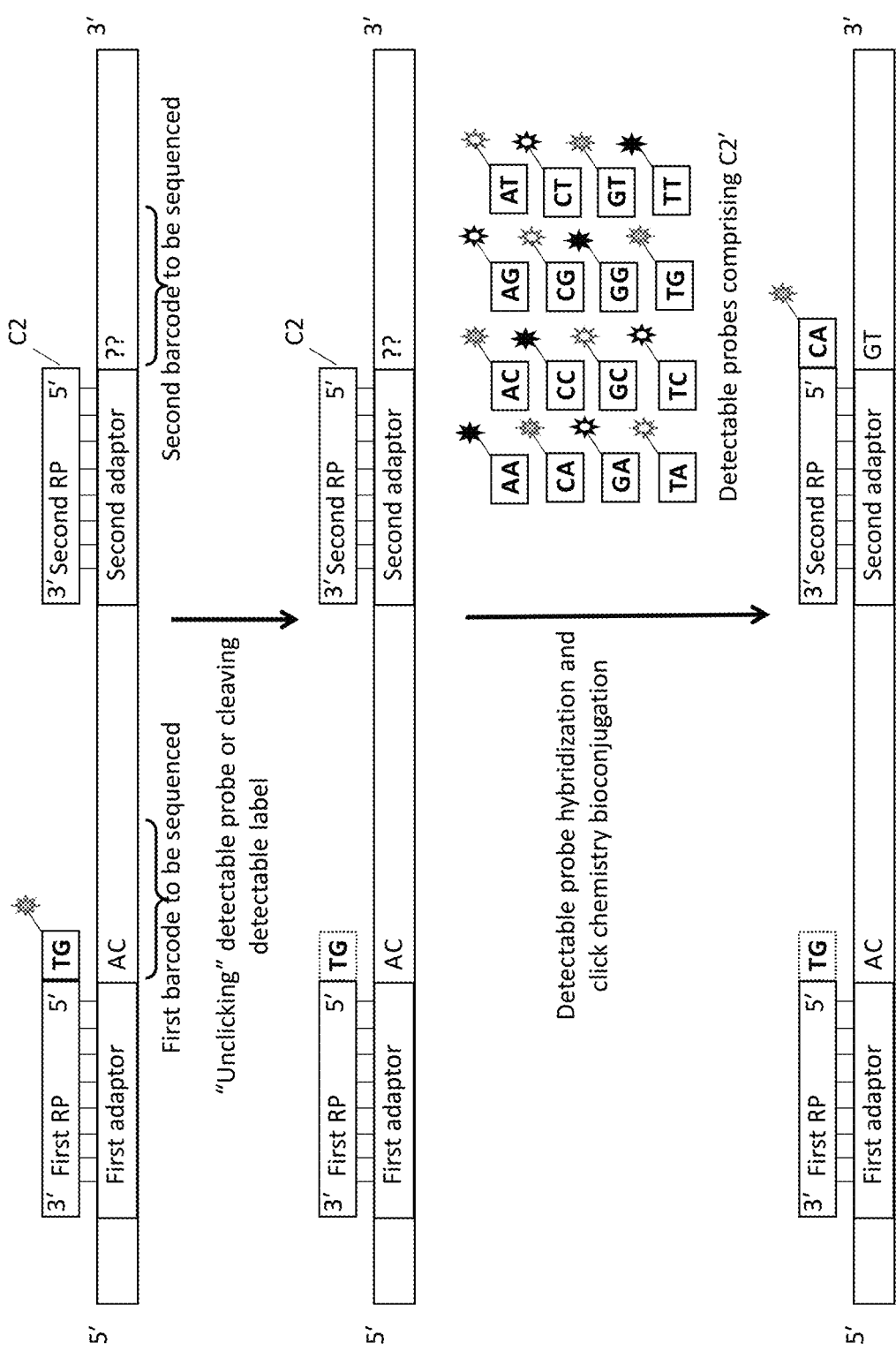
Figure 4C:
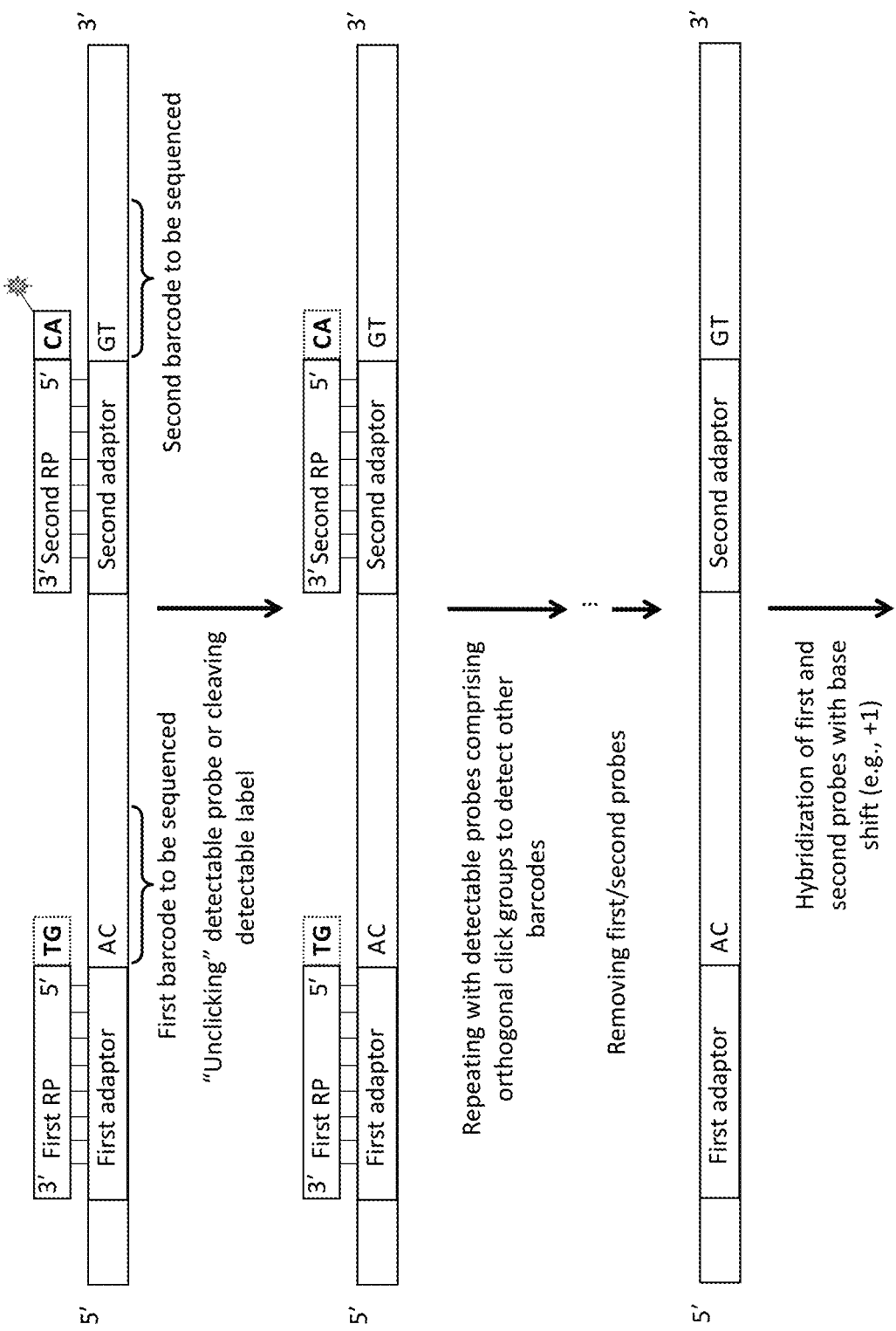
Figure 4D:
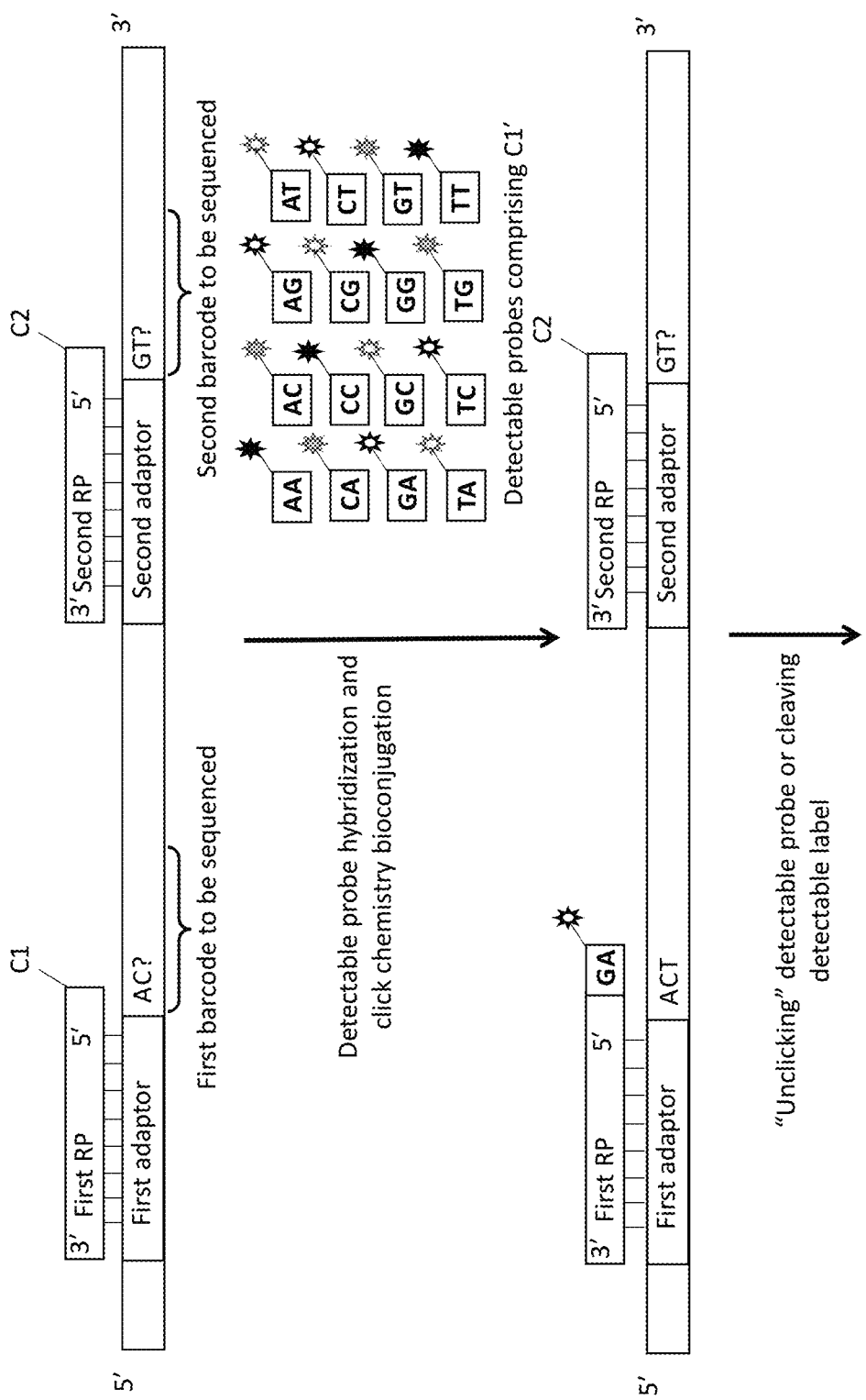
Figure 4E:
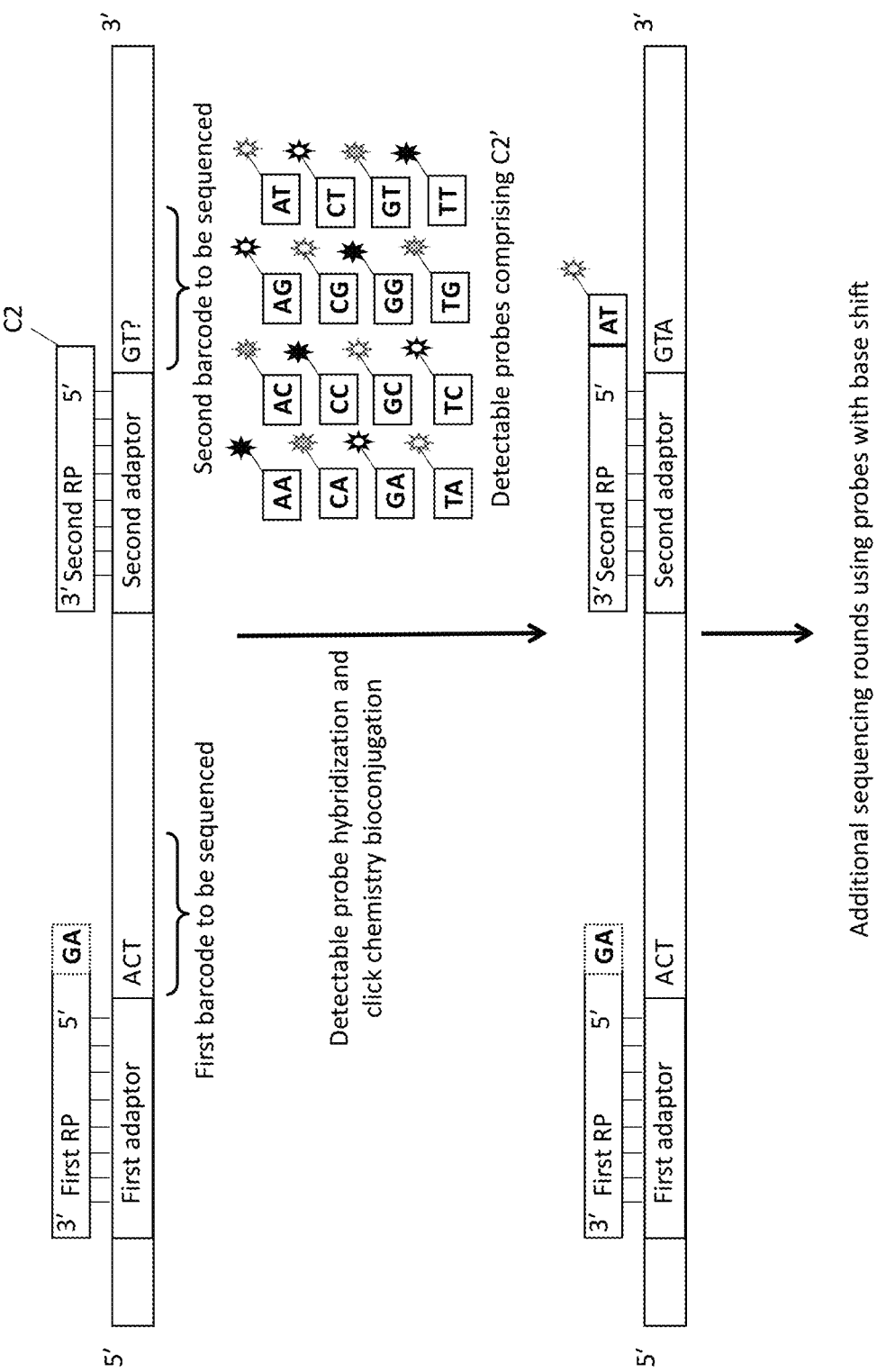
Figure 5:
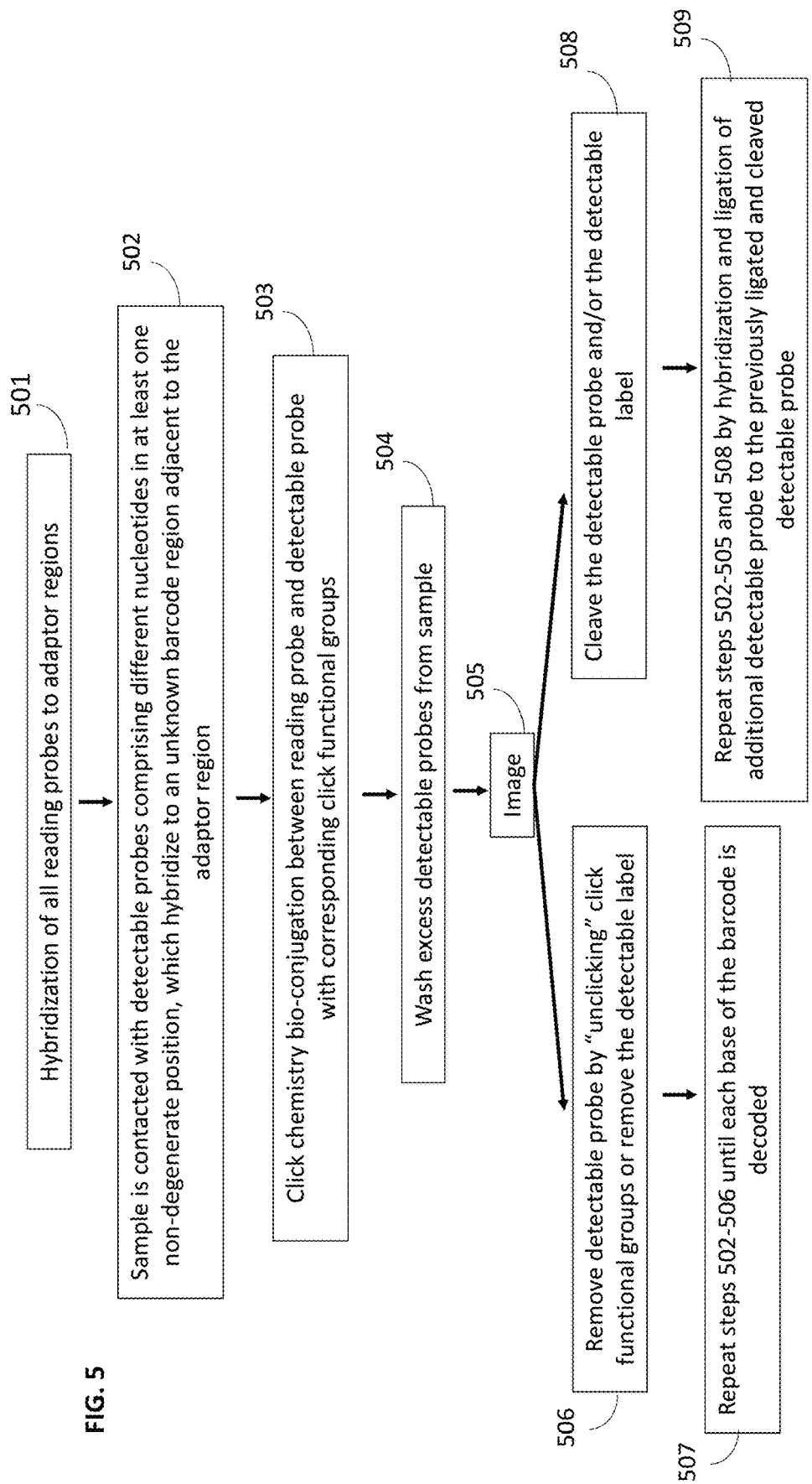
FIG. 5 shows an exemplary flowchart of in situ sequencing-by-ligation using click chemistry bioconjugation disclosed herein.

As described in FIG. 5, a method described herein comprises contacting a reading probe with a composition that includes multiple different detectable probes. In 501, a sample is contacted with a composition of reading probes in situ that hybridize with the adaptor regions (e.g., adaptor sequences) of a template. In some embodiments, the reading probes have a known sequence and hybridize with a complementary adaptor sequence in the template. In some embodiments, the reading probes comprise a click functional group, such as any of the click functional groups described herein. In some embodiments, the sample is contacted with a plurality of reading probes at the same time, and each reading probe is hybridized to its complementary adaptor region in the sample. The complementary adaptor region can be a universal adaptor region, or a common adaptor region for two or more different target polynucleotide sequences (e.g., barcode or sub-barcode sequences to be determined). The sample is then contacted with detectable probes in 502. The detectable probes may be of the same length or of different length. In some embodiments, the detectable probes comprise a series of universal bases or degenerate base, but also comprise different nucleotides at at least one non-degenerate position. The detectable probes further comprise a click functional group and a detectable label, such as a fluorophore. In some embodiments, upon contact with the sample, a detectable probe hybridizes with an unknown barcode region that is adjacent to the adaptor region. In some embodiments, a click chemistry bioconjugation reaction occurs between the click functional group of the hybridized detectable probe and the click functional group of the hybridized reading probe in 503. In some embodiments, unbound detectable probes (e.g., probes comprising non-degenerate nucleotide(s) not complementary to a sequence to be detected in the unknown barcode region) are washed from the sample in 504, and the detectable probe that remains hybridizes to the unknown barcode region is ligated and the ligated product comprising the detectable label is imaged in 505. In some examples, after imaging, the detectable probes are removed from the sample by "unclicking" the detectable probe from the reading probe in 506. In some embodiments, the reading probe remains hybridized to the adaptor region while the detectable probe is removed. In some embodiments, through the "unclicking" reaction, the click functional group is regenerated. For instance, reversible click reactions may be used in the disclosure herein. See, e.g., Bio et al., "Click and photo-unclick chemistry of aminoacrylate for visible light-triggered drug release," *Chem. Commun.*, 2012, 48, 6517-6519. In some embodiments, the reading probe is removed from the adaptor region and a new reading probe (e.g., another molecule of the same reading probe) can be provided and hybridized to the adaptor region for a subsequent reaction (e.g., a new round). As shown in step 507, steps 502-506 may be repeated until the entire sequence of the unknown barcode region is decoded, for example as illustrated in FIGS. 3A-3B. In some embodiments, the reading probe is removed from the adaptor region and a new reading probe (e.g., a different reading probe with base shift) can be provided and hybridized to the adaptor region for a subsequent reaction (e.g., a new round). In some embodiments, steps 502-506 may be repeated with different types of click reaction until the multiple sequences (e.g., sub-barcode) is decoded, for example as illustrated in FIG. 2B. Alternatively, the cleavable detectable label can be cleaved from the detectable probe following imaging in 508. Hybridization and ligation of additional detectable probes to the previously ligated and cleaved detectable probes may be used to sequence the barcode in 509, using (i) any click chemistry disclosed herein (e.g., between a click functional group on a cleaved ligation product and a click functional group on a fluorescently labeled detectable probe) and/or (ii) enzymatic ligation between a 5' phosphate (e.g., on a cleaved ligation product) and a 3' hydroxyl (e.g., on a fluorescently labeled detectable probe). In some embodiments, enzymatic ligation (e.g., using a ligase) of detectable probes and the click chemistry ligation disclosed herein can be combined in any suitable combination. In some embodiments, a 5' phosphate can be provided on a first detectable probe that has been ligated to a reading probe via click chemistry ligation. In some embodiments, a second detectable probe can be ligated to the first detectable probe by a ligase, e.g., via a ligation reaction between the 5' phosphate of the first detectable probe and the 3' hydroxyl of the second detection probe. In some embodiments, the second detectable probe may comprise a click functional group, such that the second detectable probe can be conjugated to a click functional group on a third detectable probe. Hybridization of detectable probes and ligation (via enzymatic ligation and/or click chemistry ligation) to reading probes (or ligation products thereof) can be repeated in one or more cycles to determine a sequence of the unknown barcode region.

FIGS. 3A-3B are a schematic diagram that shows one example of a sequencing procedure that can be used to determine the sequence of a barcode region. The position of the interrogatory nucleotide or sequence (e.g., a single interrogatory nucleotide as shown in the illustrations) is shifted in each cycle of detectable probe hybridization, thereby determining a sequence of the barcode region. FIG. 3A shows a sample contacted with a reading probe, comprising a click functional group C, that is complementary to and hybridizes with an adaptor region. The adaptor region is adjacent to an unknown barcode region. Following the hybridization of the reading probe, the sample is contacted with a composition of detectable probes comprising a click functional group C'. In some embodiments, the detectable probes are of the same length, but include different nucleotides in at least one non-degenerate position in each sequence, as previously described. In some embodiments, the composition includes multiple detectable probes, each having a different nucleotide in the first 3' sequence position of the detectable probe, and degenerate bases in the remaining positions. In some embodiments, the position within the nucleotide sequence that includes a known nucleotide and not a degenerate base can be referred to as the "3' sequence position." In some embodiments, the 3' sequence position is the first nucleotide at the 3' end of the detectable probe. In some embodiments, the 3' sequence position is the second nucleotide from the 3' end of the detectable probe. In some embodiments, the 3' sequence position includes the first two nucleotides adjacent from the 3' end of the detectable probe. In some embodiments, the 3' sequence position is at position 3, 4, 5, 6, 7, 8, 9, or 10 from the 3' end of the detectable probe (e.g., sequencing probe). For example, when the 3' sequence position is at position 3 from the 3' end of a sequencing probe, the detectable probe can have a sequence including, without limitation, 3'-NNXNNNNN-5', where X is the non-degenerate base (e.g., A, G, C, T or U) and where N represents the degenerate bases (e.g., universal bases).

In some embodiments, the detectable probe that is complementary to the barcode region at the non-degenerate position is bioconjugated to the reading probe via a reaction between click functional group C of the reading probe and click functional group C' of the detectable probe, and hybridizes to the barcode region. The non-hybridized detectable probes are removed (e.g., removed using a washing step). In some embodiments, an image of the detectable label of the hybridized detectable probe is obtained. Non-limiting examples of the detectable label include an optical label, a radioactive label, a fluorescent label, an enzymatic label, a chemiluminescent label, a bioluminescent label, a dye, or any of the other optical labels described herein. The image of the detectable label provides a spatial location of the first label in the image relative to other reading probes in the sample. In some embodiments, because the first detectable label (e.g., any of the exemplary labels described herein) corresponds to the location of the reading probe and the feature to which it is attached, the feature is then associated with a location in the sample. In some embodiments, the feature location corresponds to the label location in the sample, as determined from the image.

In some embodiments, as shown in FIG. 3A, the detectable probe is "unclicked" from the reading probe and removed from the sample. In some embodiments, the reading probe remains hybridized with the adaptor region although the detectable probe is removed. This allows for the cycle to be repeated (e.g., contacting the sample with a composition of detectable probes with click functional groups, bioconjugation of the detectable probes with the reading probes and hybridization of the detectable probes with the unknown barcode sequence, and imaging), see, e.g., FIG. 3B, until all or a portion of the barcode has been decoded. In some embodiments, only a portion of the barcode is determined. For example, to uniquely distinguish among the barcodes of the reading probes in the sample, it may be sufficient to determine only a portion of the complete sequence of each barcode. Accordingly, the sequencing process can be terminated when a sufficient portion of each barcode has been sequenced to unambiguously distinguish the barcodes from one another.

In some embodiments, after each detectable probe has been hybridized and the sequence of a portion of the barcode determined, the cleavable detectable label of the hybridized detectable probe can be removed via cleavage. In some embodiments, cleavage of the detectable level of the detectable probe comprises cleavage of a portion of the probe hybridized to the barcode which a portion of the detectable probe remains bioconjugated with the reading probe. In some embodiments, a detectable probe (e.g., any of the exemplary detectable probes described herein) includes a nuclease recognition site. In some embodiments, the detectable probe comprises a cleavable detectable label, and a cleavage agent can be used to cleave at least the detectable label from the end of the detectable probe, thereby generating a 5' phosphate. Optionally, a kinase adds a phosphate group to the cleaved first detectable probe if the nuclease reaction removes the free 5' phosphate necessary for ligation of the additional detectable probe.

In some embodiments, a successive detectable probe can be ligated to the remaining portion of the detectable probe, and can hybridize to the barcode to extend the sequencing procedure. The additional detectable probe hybridizes to the next unpaired nucleotide of the region of interest based on complementarity of the 3' nucleotide of the additional detectable probe to the next unpaired nucleotide sequence of the barcode region. An image is obtained of the optical label associated with the additional detectable probe while the additional detectable probe is hybridized to the barcode region. One nucleotide of the barcode region is determined by identifying the complement of the known nucleotide at the 3' sequence position of the additional detectable probe. In some embodiments, hybridization, ligation, detection, and cleavage of the cleavable detectable label is repeated to determine a sequence of the barcode region.

IV. Detection and Sequencing Analysis

In some aspects, the methods described herein further comprise detecting the cleavable detectable label and analysis the target sequence in situ. In some embodiments, detecting involves using detection methods such as flow cytometry; sequencing; probe binding and electrochemical detection; pH alteration; catalysis induced by enzymes bound to DNA tags; quantum entanglement; Raman spectroscopy; terahertz wave technology; and/or scanning electron microscopy. In some aspects, the flow cytometry is mass cytometry or fluorescence-activated flow cytometry. In some aspects, the detecting comprises performing microscopy, scanning mass spectrometry or other imaging techniques described herein. In such aspects, the detecting comprises determining a signal, e.g., a fluorescent signal.

In some aspects, the detection (comprising imaging) is carried out using any of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detectable probe. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" comprises any microscope that uses fluorescence to generate an image, whether it is a more simple set up like an epifluorescence microscope, or a more complicated design such as a confocal microscope, which uses optical sectioning to get better resolution of the fluorescent image.

In some embodiments, confocal microscopy is used for detection and imaging of the detectable probe. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required. As only one point in the sample is illuminated at a time, 2D or 3D imaging requires scanning over a regular raster (i.e., a rectangular pattern of parallel scanning lines)

in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECSTM), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

In some embodiments, sequencing can be performed in situ. In situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (i.e., nucleotide sequence) of the incorporated nucleotides or labeled primer extension products can be determined, and consequently, the nucleotide sequence of the corresponding template nucleic acid. Aspects of in situ sequencing are described, for example, in Mitra et al., (2003) *Anal. Biochem.* 320, 55-65, and Lee et al., (2014) *Science,* 343(6177), 1360-1363, US 2016/0024555, US 2019/0194709, and in U.S. Pat. Nos. 10,138,509, 10,494, 662 and 10,179,932. Exemplary techniques for in situ sequencing comprise, but are not limited to, STARmap (described for example in Wang et al., (2018) *Science,* 361(6499) 5691), MERFISH (described for example in Moffitt, (2016) *Methods in Enzymology,* 572, 1-49), hybridization-based in situ sequencing (HybISS) (described for example in Gyllborg et al., Nucleic Acids Res (2020) 48(19):e112, and FISSEQ (described for example in US 2019/0032121).

In some aspects, the analysis and/or sequence determination can be carried out at room temperature for best preservation of tissue morphology with low background noise and error reduction. In some embodiments, the analysis and/or sequence determination comprises eliminating error accumulation as sequencing proceeds.

In some embodiments, the analysis and/or sequence determination involves washing to remove unbound polynucleotides, thereafter revealing a fluorescent product for imaging.

V. Compositions, Kits, and Systems

In some embodiments, provided herein are compositions comprising a hybridization mix of templates, reading probes with click functional groups, and detectable probes with click functional groups and fluorescent labels. In some embodiments, disclosed herein is a composition that comprises a complex containing a first nucleic acid sequence, a second nucleic acid sequence, a first reading probe comprising click functional group C1, and a second reading probe comprising click functional group C2, e.g., any of the templates (e.g., nucleic acid comprising a target polynucleotide sequence) and primers (e.g., probes hybridizing to adaptor sequences) described in Section III. In some embodiments, the templates comprise a target nucleic acid or an amplification product thereof (e.g., a RCA amplification product thereof). In some embodiments, the reading probes are any of the reading probes described herein, comprising any of the click functional groups described herein. In some embodiments, the complex further comprises a detectable probe (e.g., a detectable probe comprising a detectable label and a click functional group), e.g., as described in Section III.D. In some embodiments, the detectable probe comprises a click functional group C1' that is capable of reacting with the click functional group C1 of the first reading probe, in order to create a ligated probe complex. In some embodiments, the hybridization mix comprises up to four templates, four reading probes comprising click functional groups C1, C2, C3, and C4, and four detectable probes comprising fluorescent labels and click functional groups C1', C2', C3' and C4'.

Also provided are kits, for example, comprising one or more polynucleotides of the polynucleotide probe set and reagents for performing the methods provided herein, for example, reagents required for one or more steps including hybridization, ligation, amplification, detection, sequencing, sample preparation, embedding and/or anchoring as described herein. The various components of the kit may be present in separate containers or certain compatible components may be precombined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for embedding the biological sample. In some embodiments, the kits contain reagents, such as enzymes and buffers for ligation and/or amplification, such as ligases and/or polymerases. In some aspects, the kit can also include any of the reagents described herein, e.g., wash buffer, and ligation buffer. In some embodiments, the kits contain reagents for detection and/or sequencing, such as barcode detectable probes or detectable labels. In some embodiments, the kits optionally contain other components, for example: nucleic acid primers, enzymes and reagents, buffers, nucleotides, modified nucleotides, reagents for additional assays.

VI. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the term "target nucleic acid" is any polynucleotide nucleic acid molecule (e.g., DNA molecule; RNA molecule, modified nucleic acid, etc.) for assessment in accordance with the provided embodiments, such as a polynucleotide present in a cell. In some embodiments, the target nucleic acid is a coding RNA (e.g., mRNA). The target may, In some embodiments, be a single RNA molecule. In other embodiments, the target may be at least one RNA molecule, e.g., a group of 2, 3, 4, 5, 6 or more RNA molecules. These RNA molecules may differ in molecule type, and/or may differ in sequence. In some embodiments, the target nucleic acid is, for example, a non-coding RNA (e.g., tRNA, rRNA, microRNA (miRNA), mature miRNA or immature miRNA). In some embodiments, the target nucleic acid is a splice variant of an RNA molecule (e.g., mRNA, pre-mRNA, etc.) in the context of a cell. A suitable target nucleic acid can therefore be an unspliced RNA (e.g., pre-mRNA, mRNA), a partially spliced RNA, or a fully spliced RNA, etc. Target nucleic acids of interest may be variably expressed, i.e., have a differing abundance, within a cell population, wherein the methods of the invention allow profiling and comparison of the expression levels of nucleic acids, including but not limited to, RNA transcripts, in individual cells. A target nucleic acid can also be a DNA molecule, e.g., a denatured genomic, viral, plasmid, etc. For example, the methods can be used to detect copy number variants, e.g., in a cancer cell population in which a target nucleic acid is present at different abundance in the genome of cells in the population; a virus-infected cells to determine the virus load and kinetics, and the like.

The terms "polynucleotide," "polynucleotide," and "nucleic acid molecule", used interchangeably herein, refer to polymeric forms of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer including purine and pyrimidine bases or other natural, chemically or biochemically modified, non-natural, or derivatized nucleotide bases. The backbone of the polynucleotide can include sugars and phosphate groups (as may typically be found in RNA or DNA), or modified or substituted sugar or phosphate groups.

"Hybridization" as used herein may refer to the process in which two single-stranded polynucleotides bind non-covalently to form a stable double-stranded polynucleotide. In one aspect, the resulting double-stranded polynucleotide can be a "hybrid" or "duplex." "Hybridization conditions" typically include salt concentrations of approximately less than 1 M, often less than about 500 mM and may be less than about 200 mM. A "hybridization buffer" includes a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are often performed under stringent conditions, i.e., conditions under which a sequence will hybridize to its target sequence but will not hybridize to other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. The melting temperature $T_m$ can be the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation, $T_m=81.5+0.41$ (% G+C), when a nucleic acid is in aqueous solution at 1 M NaCl (see e.g., Anderson and Young, Quantitative Filter Hybridization, in *Nucleic Acid Hybridization* (1985)). Other references (e.g., Allawi and SantaLucia, Jr., *Biochemistry*, 36:10581-94 (1997)) include alternative methods of computation which take structural and environmental, as well as sequence characteristics into account for the calculation of $T_m$.

In general, the stability of a hybrid is a function of the ion concentration and temperature. Typically, a hybridization reaction is performed under conditions of lower stringency, followed by washes of varying, but higher, stringency. Exemplary stringent conditions include a salt concentration of at least 0.01 M to no more than 1 M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of approximately 30° C. are suitable for allele-specific hybridizations, though a suitable temperature depends on the length and/or GC content of the region hybridized. In one aspect, "stringency of hybridization" in determining percentage mismatch can be as follows: 1) high stringency: 0.1×SSPE, 0.1% SDS, 65° C.; 2) medium stringency: 0.2×SSPE, 0.1% SDS, 50° C. (also referred to as moderate stringency); and 3) low stringency: 1.0×SSPE, 0.1% SDS, 50° C. It is understood that equivalent stringencies may be achieved using alternative buffers, salts and temperatures. For example, moderately stringent hybridization can refer to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions can be conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1%

SDS at 65° C. Low stringency hybridization can refer to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See M. Kanehisa, Nucleic Acids Res. 12:203 (1984).

A "primer" used herein can be an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

"Ligation" may refer to the formation of a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide.

"Multiplexing" or "multiplex assay" herein may refer to an assay or other analytical method in which the presence and/or amount of multiple targets, e.g., multiple nucleic acid target sequences, can be assayed simultaneously by using more than one capture probe conjugate, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

The term "about" as used herein refers to the usual error range for the respective value readily known to the skilled person in this technical field. Reference to "about" a value or parameter herein includes (and describes) embodiments that are directed to that value or parameter per se.

As used herein, the singular forms "a," "an," and "the" include plural referents unless the context clearly dictates otherwise. For example, "a" or "an" means "at least one" or "one or more."

The term "each," when used in reference to a collection of items, is intended to identify an individual item in the collection but does not necessarily refer to every item in the collection, unless expressly stated otherwise, or unless the context of the usage clearly indicates otherwise.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

EXAMPLES

The following examples are included for illustrative purposes only and are not intended to limit the scope of the invention.

Example 1: Sequencing Using Chemical Bioconjugation

This example demonstrates a bio-orthogonal chemical ligation (e.g., click-chemistry) to direct in situ sequencing.

A single-stranded polynucleotide template with a known constant region (e.g., adaptor region for reading probe hybridization) and an adjacent barcode region of unknown sequence is contacted with a single-stranded reading probe complementary to the constant region (FIG. 1). The reading probe has a click functional group C, e.g., attached to its 5' or 3' end. After reading probe hybridization (about 20 minutes), detectable probes of random sequence (about seven nucleotides (nt) in length) comprising a random sequence and an interrogating base (e.g., A, T, C, G in the fourth position in FIG. 1) are added. Each detectable probe has a click functional group C' attached to its 3' or 5' end and a fluorophore, e.g., attached to its 5' or 3' end. Click functional group C can undergo a click reaction with click functional group C1. The color of the fluorophore corresponds to the fourth base of the detectable probe (e.g., the known, interrogatory base). The detection porbe comprises a detectable label, such as a fluorophore, that may be used for downstream imaging analyses. For example, a known fluorophore is associated with the interrogating base (e.g., A=red, T=green, C=yellow, G=blue) such that the fluorescent signal identifies the interrogated base.

The detectable probe with sequence complementary to the polynucleotide template's barcode sequence then hybridizes to the barcode sequence of the template, bringing the click functional groups of the reading probe and the hybridized detectable probe into close proximity. A click reaction is then performed to conjugate the reading probe to the hybridized detectable probe (about five minutes), and any unhybridized or unconjugated detectable probes are washed away (about one minute). The polynucleotide is then imaged (about five minutes), with the color of the detectable signal indicative of the fourth base in the barcode sequence. After imaging, the conjugated detectable probe is optionally chemically cleaved to remove the fluorophore (about five minutes). The hybridization, detection, and removal of additional detectable probes (e.g., interrogating a different base). This cycle (including optional cleavage and stripping) may be repeated any suitable number of times to interrogate and sequence additional bases at one or more other positions to determine the barcode sequence of the polynucleotide is sequenced to identify the target polynucleotide.

Example 2: Sequencing Using Chemical Bioconjugation and Multiplexing

This example demonstrates the multiplexing of a bio-orthogonal chemical ligation (e.g., click-chemistry) to direct in situ sequencing.

Two single-stranded polynucleotide templates, each with a known constant region and an adjacent barcode region of unknown sequence, are contacted with single-stranded reading probes complementary to the constant regions. Then, detectable probes comprising a random sequence and an interrogating base are added. The reading probe complementary to the first polynucleotide template has click functional group C1 attached to its 5' end, and the reading probe complementary to the second polynucleotide template has click functional group C2 attached to its 5' end.

After reading probe hybridization (about 20 minutes), detectable probes of random sequence (about seven nucleotides in length comprising a random sequence and an interrogating base (e.g., A, T, C, or G) are added. Each detectable probe has a click functional group C1' attached to its 3' end and a fluorophore attached to its 5' end. Click functional group C1' can undergo a click reaction only with click functional group C1. Therefore, bioconjugation of the detectable probes to the reading probes occurs via separate, bio-orthogonal click reactions using different click functional groups. The color of the fluorophore corresponds to the fourth base from the 3' end of the detectable probe. For example, a known fluorophore is associated with the interrogating base (e.g., A=red, T=green, C=yellow, G=blue) such that the fluorescent signal identifies the interrogated base. After hybridization, a click reaction is performed to conjugate the detectable probe to the first polynucleotide template's reading probe (about five minutes), and any unhybridized or unconjugated detectable probes are washed away (about one minute). The polynucleotides are then imaged (about five minutes), with the color of the detectable signal indicative of the fourth base in the first polynucleotide template's barcode sequence. After imaging, the conjugated detectable probe is optionally chemically cleaved to remove the fluorophore (about five minutes). The detectable probe may be "unclicked" from the reading probe and removed from the sample, while the reading probe remains hybridized with the adaptor region.

This process is repeated using additional detectable probes with click functional group C2'. Click functional group C2' can undergo a click reaction only with click functional group C2. Reading probe hybridization may but does not need to be repeated. The click chemistry bioconjugation described in this example may be used in a multiplexed in situ assay.

Example 3: Sequencing Using Chemical Bioconjugation and Dinucleotides

This example demonstrates the reaction of dinucleotides comprises click functional groups with reading probes comprising corresponding click functional groups, to direct in situ sequencing.

Four single-stranded polynucleotide templates, each with a known constant region and an adjacent barcode region of unknown sequence, are contacted with single-stranded reading probes complementary to the constant regions (e.g., adaptor sequence) (FIGS. 3A-3B). The target sequence of the polynucleotide templates can be barcode sequences in an RCA product generated from, e.g., a circularized SNAIL probe. Each reading probe has a click functional group attached to it, e.g., at its 5' or 3' end, and the click functional groups may differ across reading probes for different barcodes to be sequenced.

After reading probe hybridization about (20 minutes), 16 unique fluorescent dinucleotides are added. Each dinucleotide has a click functional group attached to its 3' end in order to direct the click chemistry reaction; this click functional group can undergo a click reaction only with the click functional group of the first DNA template's reading probe. The color of the fluorophore is indicative of the dinucleotide sequence. After hybridization, a click reaction is performed to conjugate the dinucleotide to the first polynucleotide template's reading probe (about five minutes), and any unhybridized or unconjugated dinucleotides are washed away (about one minute). The polynucleotide molecules are then imaged (about five minutes), with the color of the detectable signal indicative of the first two bases of the first polynucleotide template's barcode sequence. After imaging, the conjugated dinucleotide is chemically cleaved to remove fluorescent signal (about five minutes). This process is repeated for the remaining polynucleotide templates and click functional groups. Reading probe hybridization does not need to be repeated.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method for analyzing a sample, comprising:
   (a) contacting the sample with a first probe and a second probe, wherein:
   the sample comprises a first nucleic acid sequence and a second nucleic acid sequence, wherein the first nucleic acid sequence comprises a first adaptor sequence and a first target polynucleotide sequence adjacent to the first adaptor sequence, and the second nucleic acid sequence comprises a second adaptor sequence and a second target polynucleotide sequence adjacent to the second adaptor sequence, and
   the first probe comprises click functional group C1 and hybridizes to the first adaptor sequence, and the second probe comprises click functional group C2 and hybridizes to the second adaptor sequence;

(b) contacting the sample with a first detectable probe, wherein the first detectable probe comprises click functional group C1' and hybridizes to the first target polynucleotide sequence, thereby juxtaposing C1 and C1';

(c) reacting C1 with C1' in a click reaction, thereby ligating the first probe to the first detectable probe to form a first ligated product hybridized to the first nucleic acid sequence, wherein the click reaction between C1 and C1' is orthogonal to a click reaction involving C2; and (d) detecting a first signal associated with the first ligated product, wherein the first signal is indicative of a sequence of interest in the first target polynucleotide sequence.

2. The method of claim 1, further comprising:

(b') contacting the sample with a second detectable probe, wherein the second detectable probe comprises click functional group C2' and hybridizes to the second target polynucleotide sequence, thereby juxtaposing C2 and C2'.

3. The method of claim 2, further comprising:

(c') reacting C2 with C2' in a click reaction, thereby ligating the second probe to the second detectable probe to form a second ligated product hybridized to the second nucleic acid sequence, wherein the click reaction between C1 and C1' is orthogonal to the click reaction between C2 and C2'.

4. The method of claim 3, further comprising:

(d') detecting a second signal associated with the second ligated product, wherein the second signal is indicative of a sequence of interest in the second target polynucleotide sequence.

5. The method of claim 4, wherein the first detectable probe comprises an interrogatory region complementary to the sequence of interest in the first target polynucleotide sequence, and/or the second detectable probe comprises an interrogatory region complementary to the sequence of interest in the second target polynucleotide sequence.

6. The method of claim 5, wherein the first detectable probe is among a plurality of first detectable probes contacted with the sample in step (b), wherein:

the plurality of first detectable probes are of formula $N_xB_yN_z$, wherein N is a degenerate base and B is an interrogatory base, x, y, and z are integers independent of each other, wherein x is 0 or greater, y is 1 or greater, and z is 0 or greater, and each of the plurality of first detectable probes: (i) comprises click functional group C1' and a different interrogatory region, and (ii) is labeled with a detectable label corresponding to one or more of the different interrogatory regions.

7. The method of claim 6, further comprising, prior to the reacting step (c), a step of removing first detectable probes comprising interrogatory regions that are not complementary to the sequence of interest in the first target polynucleotide sequence, while the first detectable probe remains hybridized to the first target polynucleotide sequence.

8. The method of claim 5, wherein the second detectable probe is among a plurality of second detectable probes contacted with the sample in step (b'), wherein:

the plurality of second detectable probes are of formula $N_aB_bN_c$, wherein N is a degenerate base and B is an interrogatory base, a, b, and c are integers independent of each other, wherein a is 0 or greater, b is 1 or greater, and c is 0 or greater, and each of the plurality of second detectable probes: (i) comprises click functional group C2' and a different interrogatory region, and (ii) is labeled with a detectable label corresponding to one or more of the different interrogatory regions.

9. The method of claim 8, further comprising, prior to the reacting step (c'), a step of removing second detectable probes comprising interrogatory regions that are not complementary to the sequence of interest in the second target polynucleotide sequence, while the second detectable probe remains hybridized to the second target polynucleotide sequence.

10. The method of claim 5, wherein the sequence of interest in the first target polynucleotide sequence is a single nucleotide or dinucleotide sequence.

11. The method of claim 5, wherein the sequence of interest in the second target polynucleotide sequence is a single nucleotide or dinucleotide sequence.

12. The method of claim 4, further comprising, after the detecting in step (d) or (d'):

(i) a step of cleaving the first or second detectable probe, respectively; and/or (ii) a step of unhybridizing the first or second ligated product or a portion thereof from the first or second nucleic acid sequence, respectively.

13. The method of claim 3, wherein the click reaction between C1 and C1' and the click reaction between C2 and C2' are independently selected from the group consisting of a nucleophilic addition reaction, a cyclopropane-tetrazine reaction, a strain-promoted azide-alkyne cycloaddition (SPAAC) reaction, an alkyne hydrothiolation reaction, an alkene hydrothiolation reaction, a strain-promoted alkyne-nitrone cycloaddition (SPANC) reaction, an inverse electron-demand Diels-Alder (IED-DA) reaction, a cyanobenzothiazole condensation reaction, an aldehyde/ketone condensation reaction, and Cu(I)-catalyzed azide-alkyne cycloaddition (CuAAC) reaction, and/or wherein the click reaction between C1 and C1' and/or the click reaction between C2 and C2' are independently selected from the group consisting of a template-dependent reaction and a template-independent reaction.

14. The method of claim 3, wherein:

(i) the click functional group C1 is on the 5' of the first probe and the click functional group C1' is on the 3' of the first detectable probe, or the click functional group C1 is on the 3' of the first probe and the click functional group C1' is on the 5' of the first detectable probe; and/or (ii) the click functional group C2 is on the 5' of the second probe and the click functional group C2' is on the 3' of the second detectable probe, or the click functional group C2 is on the 3' of the second probe and the click functional group C2' is on the 5' of the second detectable probe.

15. The method of claim 3, wherein C1/C1' and/or C2/C2' are independently selected from the group consisting of:

(i) 3'-azido/5'-alkynyl;
(ii) 3'-alkynyl/5'-azido;
(iii) 3'-azido/5'-cyclooctynyl;
(iv) 3'-cyclooctynyl/5'-azido;
(v) 3'-tetrazine/5'-dienophile;
(vi) 3'-dienophile/5'-tetrazine;
(vii) 3'-thiol/5'-alkynyl;

(viii) 3'-alkynyl/5'-thiol;
(ix) 3'-cyano/5'-1,2-amino thiol;
(x) 3'-1,2-amino thiol/5'-cyano;
(xi) 3'-nitrone/5'-cyclooctynyl; and
(xii) 3'-cyclooctynyl/5'-nitrone.

16. The method of claim 3, wherein the first probe and the second probe are hybridized to the first and second nucleic acid sequences, respectively, prior to contacting the sample with the first and second detectable probes.

17. The method of claim 2, wherein the first detectable probe and/or the second detectable probe comprise a fluorescent label or an overhang that hybridizes to a fluorescently labeled probe.

18. The method of claim 1, wherein the first probe and/or the second probe remain hybridized to the first and second adaptor sequences, respectively, during one or more additional cycles of contacting the sample with additional detectable probes, additional click reactions, and additional signal detections.

19. The method of claim 1, wherein the first target polynucleotide sequence and the second target polynucleotide sequence are barcode sequences or sub-barcode sequences corresponding to an analyte.

20. The method of claim 1, wherein the first nucleic acid sequence and the second nucleic acid sequence are sequences of one or more rolling circle amplification (RCA) products generated in situ in the sample.

21. A method for analyzing a sample, comprising:
(a) contacting the sample with a first probe and a second probe, wherein:
the sample comprises a first nucleic acid sequence and a second nucleic acid sequence, wherein the first nucleic acid sequence comprises a first adaptor sequence and a first target polynucleotide sequence adjacent to the first adaptor sequence, and the second nucleic acid sequence comprises a second adaptor sequence and a second target polynucleotide sequence adjacent to the second adaptor sequence, and
the first probe comprises click functional group C1 and hybridizes to the first adaptor sequence, and the second probe comprises click functional group C2 and hybridizes to the second adaptor sequence;
(b) contacting the sample with a plurality of first detectable probes of formula $N_xB_yN_z$,
wherein N is a degenerate base and B is an interrogatory base, x, y, and z are integers independent of each other, x is 0 or greater, y is 1 or 2, and z is 0 or greater,
wherein each of the plurality of first detectable probes comprises: (i) click functional group C1', (ii) interrogatory region $B_y$, and (iii) a detectable label corresponding to one or more different interrogatory regions in the plurality of first detectable probes, and
wherein the first detectable probe comprising the interrogatory region complementary to a corresponding sequence of interest in the first target polynucleotide sequence hybridizes to the first nucleic acid sequence, thereby juxtaposing C1 of the first probe and C1' of the first detectable probe;
(c) reacting C1 with C1' in a click reaction, thereby ligating the first probe to the first detectable probe to form a first ligated product hybridized to the first nucleic acid sequence;
(d) detecting a signal associated with the first ligated product, wherein the signal is indicative of the sequence of interest in the first target polynucleotide sequence;
(e) contacting the sample with a plurality of second detectable probes of formula $N_aB_bN_c$,
wherein N is a degenerate base and B is an interrogatory base, a, b, and c are integers independent of each other, a is 0 or greater, b is 1 or 2, and c is 0 or greater,
wherein each of the plurality of second detectable probes comprises: (i) click functional group C2', (ii) interrogatory region $B_b$, and (iii) a detectable label corresponding to one or more different interrogatory regions in the plurality of second detectable probes, and
wherein the second detectable probe comprising the interrogatory region complementary to a corresponding sequence of interest in the second target polynucleotide sequence hybridizes to the second nucleic acid sequence, thereby juxtaposing C2 of the second probe and C2' of the second detectable probe;
(f) reacting C2 with C2' in a click reaction, thereby ligating the second probe to the second detectable probe to form a second ligated product hybridized to the second nucleic acid sequence, wherein the click reaction between C1 and C1' is orthogonal to the click reaction between C2 and C2'; and
(g) detecting a signal associated with the second ligated product, wherein the signal is indicative of the sequence of interest in the second target polynucleotide sequence.

22. The method of claim 21, wherein the second probe remains hybridized to the second adaptor sequence in steps (b) through (g).

* * * * *